United States Patent [19]
Cook et al.

[11] Patent Number: 5,811,534
[45] Date of Patent: Sep. 22, 1998

[54] SUBSTITUTED PURINES AND OLIGONUCLEOTIDE CROSS-LINKING

[75] Inventors: Phillip Dan Cook; Muthiah Manoharan, both of Carlsbad; Kanda S. Ramasamy, Laguna Hills, all of Calif.

[73] Assignee: ISIS Pharmaceuticals, Inc., Carlsbad, Calif.

[21] Appl. No.: 948,151

[22] Filed: Oct. 9, 1997

Related U.S. Application Data

[63] Continuation of Ser. No. 189,792, Feb. 1, 1994, Pat. No. 5,681,941.

[51] Int. Cl.$^6$ .............................. C07H 21/00; C07H 19/16
[52] U.S. Cl. ...................... 536/23.1; 536/22.1; 536/25.3; 536/25.34; 536/26.26; 536/26.7; 544/264
[58] Field of Search .................................. 536/22.1, 23.1, 536/25.3, 25.34, 26.26, 26.7; 544/264

[56] References Cited

U.S. PATENT DOCUMENTS

| | | | |
|---|---|---|---|
| 3,666,856 | 5/1972 | Elion et al. | 424/180 |
| 3,758,684 | 9/1973 | Elion et al. | 424/180 |
| 3,919,193 | 11/1975 | Mian et al. | 260/211.5 R |
| 4,048,307 | 9/1977 | Yokota et al. | 424/180 |
| 4,081,534 | 3/1978 | Elion et al. | 424/180 |
| 4,123,610 | 10/1978 | Summerton et al. | 536/25.3 |
| 4,230,698 | 10/1980 | Bobek et al. . | |
| 4,321,366 | 3/1982 | Bobek et al. | 536/55 |
| 4,369,181 | 1/1983 | Miller et al. . | |
| 4,381,344 | 4/1983 | Rideout et al. . | |
| 4,481,197 | 11/1984 | Rideout et al. . | |
| 4,751,221 | 6/1988 | Watanabe et al. . | |
| 4,751,292 | 6/1988 | Fox . | |
| 4,751,293 | 6/1988 | Kataoka et al. . | |
| 4,755,594 | 7/1988 | Bridges et al. . | |
| 5,378,825 | 1/1995 | Cook et al. . | |
| 5,459,255 | 10/1995 | Cook et al. . | |
| 5,681,941 | 10/1997 | Cook et al. . | |

FOREIGN PATENT DOCUMENTS

| | | |
|---|---|---|
| WO 91/10671 | 7/1991 | WIPO . |
| WO 91/14436 | 10/1991 | WIPO . |

OTHER PUBLICATIONS

Atherton et al., "The Fluorenylmethoxycarbonyl Amino Protecting Group", *The Peptides*, Gross and Meienhofer (eds.), Academic Press, New York, 1987, 9, 1–38.

Beaucage et al., "Deoxynucleoside Phosphoramidites –A New Class of Key Intermediates for Deoxypolynucleotide Synthesis", *Tetra Lett.*, 1981, 22(20), 1859–1862.

Beaucage, S.L. et al., "Advances in the Synthesis of Oligonucleotides by the Phosphoramidite Approach", *Tetrahedron*, 1992, 48, 2223–2311.

Blackburn & Gait (eds.), *Nucleic Acids in Chemistry and Biology*, Oxford University Press, New York, 1991.

Caruthers, "Synthesis of Oligonucleotides and Oligonucleotide Analogues", J.S. Cohen (ed.), CRC Press, Inc., Boca Raton, Florida, 1989, 7–24.

Casale et al., "Synthesis and Properties of an Oligodeoxynucleotide Containing a Polycyclic Aromatic Hydrocarbon Site Specifically Bound to the $N^2$ Amino Group of a 2'–Deoxyguanosine Residue",*J. Am. Chem. Soc.*, 1990, 112, 5264–5271.

Christalli, G. et al., "Synthesis of 2–Azido–(R) – $N^6$–p–Hydroxyphenylisopropyladenosine (R–Ahpia) as Potential Photoaffinity Probe for $A_1$ Adenosine Receptors", *Nucleosides & Nucleotides*, 1986, 5, 213–222.

Cohen (ed.), Oligonucleotides: *Antisense Inhibitors of Gene Express*, CRC Press, Inc., Boca Raton, FL, 1989.

Cook, P.D., "Medicinal Chemistry Strategies for Antisense Research, in Antisense Research & Applications", Crooke et al. (ed.), CRC Press, Inc., Boca Raton, FL, 1993.

Cook, "Medicinal chemistry of antisense oligonucleotides–future opportunities", *Anti–Cancer Drug Design*, 1991, 6, 585–607.

Dagle et al., "Pathways of Degradation and Mechanism of Action of Antisense Oligonucleotides in *Xenopus laevis* Embryos", *Antisense Res. Develop.*, 1991, 1, 11–20.

Dreyer et al., "Sequence–specific cleavage of single–stranded DNA: Oligonucleotide–EDTA.Fe(II)", *Proc. Natl. Acad. Sci.*, 1985, 82, 968–972.

Ferentz et al., "Disulfide Cross–Linked Oligonucleotides", *J. Am. Chem. Soc.*, 1991, 113, 4000–4002.

Ferentz, A.E. et al., "Aminolysis of 2'–Deoxyinosine Aryl Ethers: Nucleoside Model Studies for the Synthesis of Functionally Tethered Oligonucleotides", *Nucleosides and Nucleotides*, 1992, 11, 1749–1763.

Gaffney, B.L. et al., "Synthesis of O–6–Alkylated Deoxyguanosine Nucleosides", *Tetra. Lett.*, 1982, 23, 2253–2256.

Gao et al., "6–O–(Pentafluorophenyl)–2'–deoxyguanosine: A Versatile Synthon for Nucleoside and Oligonucleotide Synthesis", *J. Org. Chem.*, 1992, 57(25), 6954–6959.

Gmeiner, W.J. et al., "Development of an Efficient Oligonucleotide Derivatization Protocol", *Bioorg. Med. Chem. Lett.*, 1991, 1, 487–490.

(List continued on next page.)

*Primary Examiner*—James O. Wilson
*Attorney, Agent, or Firm*—Woodcock Washburn Kurtz Mackiewicz & Norris, LLP

[57] ABSTRACT

This invention is directed to novel purine-based compounds for inclusion into oligonucleotides. The compounds of the invention, when incorporated into oligonucleotides are especially useful as "antisense" agents—agents that are capable of specific hybridization with a nucleotide sequence of an RNA. The compounds of the invention may also be used for cross-linking oligonucleotides. Oligonucleotides are used for a variety of therapeutic and diagnostic purposes, such as treating diseases, regulating gene expression in experimental systems, assaying for RNA and for RNA products through the employment of antisense interactions with such RNA, diagnosing diseases, modulating the production of proteins, and cleaving RNA in site specific fashions. The compounds of the invention include novel heterocyclic bases, nucleosides, and nucleotides. When incorporated into oligonucleotides, the compounds of the invention can be useful for modulating the activity of RNA.

83 Claims, No Drawings

OTHER PUBLICATIONS

Greene and Wuts, Protection Groups in Organic Synthesis, 2d edition, John Wiley & Sons, New York, 1991.

Grineva et al., "Complementary Addressed Modification of rRNA with p–(Chloroethylmethylamino)Benzylidene Hexanucleotides", *FEBS Letters*, 1973, 32(2), 351–355.

Haralambidis et al., "Preparation of base–modified nucleosides suitable for non–radioactive label attachment and their incorporation into synthetic oligodeoxyribonucleotides", *Nucl. Acids Res.*, 1987, 15(12), 4856–4876.

Harris et al., "New Strategy for the Synthesis of Oligonucleotides Bearing Adducts at Exocyclic Amino Sites of Purine Nucleosided", *J. Am. Chem. Soc.*, 1991,113, 4328–4329.

Hayakawa, H. et al., "A Lithiation Approach to Cordycepin Analogues Variously Substituted at the C–8 Position", *J. Het. Chem.*, 1989, 26, 189–192.

Hayakawa, H. et al., "Direct C–8 Lithiation of Naturally––Occurring Purine Nucleosides. A Simple Method for the Synthesis of 8–Carbon–Substituted Purine Nucleosides", *Chem. Pharm. Bull.*, 1987, 35, 72–79.

Hirota, K. et al., "Convenient Method for the synthesis of C–Alkylated Purine Nucleosides: Palladium–Catalyzed Cross–Coupling Reaction of Halogenopurine Nucleosides with Trialkylaluminums", *J. Org. Chem.*, 1992, 57, 5268–5270.

Horn et al., "Controlled Chemical Cleavage of Synthetic DNA at Specific Site", *Nucleosides & Nucleotides*, 1991, 10(1–3), 299–302.

Inoue et al., "Synthesis and hybridization studies on two complementary nona(2'–O–methyl)ribonucleotides", *Nucl. Acids Res.*, 1987, 15(15), 6131–6148.

Iyer et al., "Abasic oligodeoxyribonucleoside phosphorothioates: synthesis and evaluation as anti–HIV–1 agents", *Nucl. Acids Res.*, 1990, 18(10), 2855–2859.

Iyer et al., "3H–1,2–Benzodithiole–3–one 1,1–Dioxide as an Improved Sulfurizing Reagent in the Solid–Phase Synthesis of Oligodeoxyribonucleoside Phosphorothioates", *J. Am. Chem. Soc.*, 1990, 112, 1253–1254.

Johnson et al., "Site–Specific Adduct Formation in Oligomeric DNA Using a New Protecting Group", *J. Am. Chem. Soc.*, 1992, 114, 4923–4924.

Kawasaki et al., "Uniformly Modified 2'–Deoxy–2'–fluoro Phosphorothioate Oligonucleotides as Nuclease–Resistant Antisense Compounds with High Affinity and Specificity for RNA Targets", *J. Med. Chem.*, 1993, 36(7), 831–841.

Kim, S.J. et al., "A Postoligomerization Synthesis of Oligodeoxynucleotides Containing Polycyclic Aromatic Hydrocarbon Adducts at the $N^6$ Position of Deoxyadenosine", *J. Am. Chem. Soc.*, 1992, 114, 5480–5481.

Lee et al., "Syntheses of Polycyclic Aromatic Hydrocarbon–Nucleoside and Oligonucleotide Adducts Specifically Alkylated on the Amino Functions of Deoxyguanosine and Deoxyadenosine", *Tetra. Lett.*, 1990, 31, 6773–6776.

Lesnik et al., "Oligodeoxynucleotides Containing 2'–O–Modified Adenosine: Synthesis and Effects on Stability of DNA:RNA Duplexes", *Biochem.*, 1993, 32, 7832–7838.

Lindahl et al., "DNA N–Glycosidases", *J. Biol. Chem.*, 1977, 252(10), 3286–3294.

Matsuda, A. et al., "Nucleosides & Nuceotides. 103. 2–Alkynyladenosienes:A Novel Class of Antihypertensive Effects", *J. Med. Chem.*, 1992, 35, 241–252.

Matteucci et al., "Synthesis and Crosslinking Properties of a Deoxyoligonucleotide Containing $N^6,N^6$–Ethanodeoxyadenosine", *Tetra. Lett.*, 1987, 28(22), 2469–2472.

Meyer et al., "Efficient, Specific Cross–Linking and Cleavage of DNA by Stable, Synthetic Complementary Oligonucleotides", *J. Am. Chem. Soc.*, 1989, 8517–8519.

Miller et al., "A new approach to chemotherapy based on molecular biology and nucleic acid chemistry: Matagen (masking tape for gene expression)", *Anti–Cancer Drug Design*, 1987, 2, 117–128.

Mirabelli et al., "In vitro and in vivo pharmacologic activities of antisense oligonucleotides", *Anti–Cancer Design*, 1991, 6, 647–661.

Motawia et al., "A New Route to 2',3'–Dideoxycytidine", *Liebigs Ann. Chem.*, 1990, 599–602.

Nair, V. et al., "High Selectivity of Novel Isoguanosine Analogues For the Adenosine $A_1$ Receptor", *Bioorganic & Med. Chem. Lett.* 1991, 1, 481–486.

Peoc'h et al., "Efficient Chemical Synthesis of Oligodeoxynucleotides Containing a True Abasic Site", *Tetra. Lett.*, 1987, 32(2), 207–210.

Pieles et al., "Preparation of a novel psoralen containing deoxyadenosine building block for the facile solid phase synthesis of psoralen–modified oligonucleotides for a sequence specific crosslink to a given target sequence", *Nucl. Acids Res.*, 1989, 17(22), 8967–8978.

Roduit et al., "Synthesis of Oligodeoxyribonucleotides Containing an Aliphatic Amino Linker Arm at Selected Adenine Bases and Derivatization with Biotin", *Nucleotides & Nucleosides*, 1987, 6(1&2), 349–352.

Sagi, G. et al., "Synthesis and Antiviral Activities of 8–Alkynyl–, 8–Alkenyl–, and 8–Alkyl–2'–deoxyadenoside Analogues", *J. Med. Chem.*, 1994, 37, 1307–1311.

Singh et al., "Oligonucleotides, part 5+: synthesis and fluorescence studies of DNA oligomers d(AT)5 containing adenines covalently linked at C–8 with dansyl fluorophore", *Nucl. Acids Res.*, 1990, 18(11), 3339–3345.

Srivastava, P.C. et al., *Synthesis and Properties of Purine Nucleosides and Nucleotides*, Townsend, L.G., Ed.; *Nucleosides and Nucleotides*, Chapter 2: Plenum Press: New York, N.Y., 1988.

Stein et al., "Physicochemical Properties of Phosphorothioate Oligodeoxynucleotides", *Nucl. Acids Res.*, 1988, 16(8), 3209–3221.

Steinbrecher, T., "Activation of the C2 Position of Purine by the Trifluoromethanesulfonate Group: Synthesis of $N^2$–Alkylated Deoxyguanosines", *Agnew. Chem. Int.*, Ed. Engl., 1993, 32, 404–406.

Summerton, "Sequence–Specific Crosslinking Agents for Nucleic Acids: Design and Functional Group Testing", *J. Theor. Biol.*, 1979, 78 61–75.

Summerton et al., "Sequence–specific Crosslinking Agents for Nucleic Acids", *J. Mol. Biol.*, 1978, 122, 145–162.

Telser et al., "Synthesis and Characterization of DNA Oligomers and Duplexes Containing Covalently Attached Molecular Labels: Comparison of Biotin, Fluorescein, and Pyrene Labels by Thermodynamic and Optical Spectroscopic Measurements", *J. Am. Chem. Soc.*, 1989, 111, 6966–6976.

Uhlmann et al., "Antisense Oligonculeotides: A New Therapeutic Principle", *Am. Chem. Rev.*, 1990, 90(4), 543–584.

Veber et al., "Isonicotinyloxycarbonyl, a Novel Amino Protecting Group for Peptide Synthesis", *J. Org. Chem.*, 1977, 42(20), 3286–3288.

Walder et al., "Role of Rnase H in hybrid–arrested translation by antisense oligonucleotides", *Proc. Natl. Acad. Sci.*, 1988, 85, 5011–5015.

Webb et al., "Hybridization Triggered Cross–Linking of Deoxyoligonucleotides", *Nucl. Acids Res.*, 1986, 14(19), 7661–7674.

Zajc, B. et al., "Epoxide and Diol Epoxide Adducts of Polycyclic Aromatic Hydrocarbons at the Exocyclic Amino Group of Deoxyguanozine", *Tetra. Lett.*, 1992, 33, 3409–3412.

SUBSTITUTED PURINES AND OLIGONUCLEOTIDE CROSS-LINKING

RELATED APPLICATIONS

This is a continuation of application Ser. No. 08/189,792, filed Feb. 1, 1994, the disclosure of which is herein incorporated by reference.

This application is a continuation-in-part of PCT Patent Application No. PCT\US91\00243, filed Jan. 11, 1991, which is a continuation-in-part of U.S. patent Ser. No. 463,358 filed Jan. 11, 1990 and U.S. patent application Ser. No. 566,977 filed Aug. 13, 1990.

FIELD OF THE INVENTION

This invention relates to novel substituted purine compounds that may be incorporated into oligonucleotides and may serve as cross-linkers for complementary oligonucleotides and oligonucleotide analogs. Oligonucleotides and their analogs are used for a variety of therapeutic and diagnostic purposes, such as treating diseases, regulating gene expression in experimental systems, assaying for RNA and for RNA products through the employment of antisense interactions with such RNA, diagnosing diseases, modulating the production of proteins, and cleaving RNA in site specific fashions. The compounds of the invention include novel heterocyclic bases, nucleosides, and nucleotides. When incorporated into oligonucleotides, the compounds of the invention are useful, inter alia, for modulating RNA activity. The compounds are also useful as research reagents.

BACKGROUND OF THE INVENTION

It is well known that most of the bodily states in mammals, including most disease states, are affected by proteins. Such proteins, either acting directly or through their enzymatic functions, contribute in major proportion to many diseases in animals and man. Classical therapeutics has focused on interactions with such proteins in efforts to moderate their disease causing or disease potentiating functions. Recently, attempts have been made to moderate the production of such proteins by interactions with molecules that direct their synthesis, such as intracellular RNA. By interfering with the production of proteins, it has been hoped to achieve therapeutic results with maximum effect and minimal side effects. It is the general object of such therapeutic approaches to interfere with or otherwise modulate expression of genes which are responsible for the formation of undesired protein.

One method for inhibiting specific gene expression is by the use of oligonucleotides or modified oligonucleotides as "antisense" agents. As so used, oligonucleotides or modified oligonucleotides are selected to be complimentary to a specific, target, messenger RNA (mRNA) sequence. Hybridization is the sequence specific hydrogen bonding of oligonucleotides or oligonucleotide analogs to Watson-Crick base pairs of RNA or single-stranded DNA. Such base pairs are said to be complementary to one another. Antisense methodology is often directed to the complementary hybridization of relatively short oligonucleotides or modified oligonucleotides to single-stranded mRNA or single-stranded DNA such that the normal, essential functions of these intracellular nucleic acids are disrupted.

The use of oligonucleotides, modified oligonucleotides and oligonucleotide analogs as antisense agents for therapeutic and diagnostic use is actively being pursued by many commercial and academic groups. While the initial suggested mode of activity of antisense agents was via hybridization arrest, several additional mechanisms or terminating antisense events have also been studied in relation to antisense use in therapeutics. In addition to hybridization arrest these include cleavage of hybridized RNA by the cellular enzyme ribonuclease H (RNase H), RNA catalytic or chemical cleaving and cross-linking. Various reviews in the scientific literature summarize these studies. See, for example, *Oligonucleotides: Antisense Inhibitors of Gene Expression*, CRC Press, Inc., Boca Raton, Fla. (Cohen ed., 1989); Cook, P. D. *Anti-Cancer Drug Design* 1991, 6,585; Cook, P. D. *Medicinal Chemistry Strategies for Antisense Research, in Antisense Research & Applications*, Crooke, et al., CRC Press, Inc.; Boca Raton, Fla., 1993; Uhlmann, et al., *A. Chem. Rev.* 1990, 90, 543; Walder, et al., *Proc. Natl. Acad. Sci., USA,* 1988, 85, 5011; and Dagle, et al., *Antisense Research & Development*, 1991, 1, 11.

Hybridization arrest denotes the terminating event in which the oligonucleotide inhibitor binds to the target nucleic acid and thus prevents, by simple steric hindrance, the binding of essential proteins, most often ribosomes, to the nucleic acid. Methyl phosphonate oligonucleotides, such as those of Miller, et al., *Anti-Cancer Drug Design,* 1987, 2, 117–128, and α-anomer oligonucleotides are two extensively studied antisense agents that are thought to disrupt nucleic acid function by hybridization arrest.

In the RNase H terminating event, activation of RNase H by a heteroduplex formed between a DNA type oligonucleotide or oligonucleotide analog and the targeted RNA results in cleavage of target RNA by the enzyme, thus destroying the normal function of the RNA. To date, the RNAse H enzyme has been found to be activated only by either natural phosphodiester DNA oligonucleotides or phosphorothioate DNA oligonucleotides. Walder, supra and Stein, et al., *Nucleic Acids Research,* 1988, 16, 3209–3221 describe the role that RNase H plays in the antisense approach.

Oligonucleotides or modified oligonucleotides acting as chemical or catalytic RNA cleavers require either the attachment of pendent groups with acid/base properties to oligonucleotides or the use of ribozymes, i.e. RNAs having inherent catalytic properties. In the pendent group approach, the pendent group is not involved with the specific Watson-Crick hybridization of the oligonucleotide or oligonucleotide analog with the mRNA but is carried along by the oligonucleotide or oligonucleotide analog to serve as a reactive or non-reactive functionality. The pendent group is intended to interact with the mRNA in some manner to more effectively inhibit translation of the mRNA into protein. Such pendent groups have also been attached to molecules targeted to either single or double stranded DNA. Such pendent groups include intercalating agents, cross-linkers, alkylating agents, or coordination complexes containing a metal ion with associated ligands.

Cross-linking of a nucleic acid with a complimentary oligonucleotide or modified oligonucleotide is used to modulate RNA activity by disrupting the function of nucleic acids. To date this has primarily been achieved by cleaving the target. The known approaches using cross-linking agents, as well as alkylating agents and radical generating species, as pendent groups on oligonucleotides for antisense diagnostics and therapeutics have had several significant shortcomings. It is known to cross-link nucleic acids by exposure to UV light; however, such cross-linking is positionally uncontrollable. To overcome this lack of specificity, some workers have covalently cross-linked complementary strands of oligonucleotides at a specific site utilizing controlled chemistry. These workers attached a nitrogen mustard to either the 3' terminal ribose unit of an oligonucleotide or oligonucleotide analog via an acetal linkage or to the 5' end of an oligonucleotide or oligonucleotide analog via a phosphoramide linkage. On hybridization, the reactive mustards covalently cross-linked to the complementary strand via alkylation of the ternary hetero-aromatic nitrogen atom at the 7-position of guanine or adenine: see Grineva et al., *FEBS.*, 1973, 32, 351–355. Other workers have attached an α-bromomethylketone to the 4-position of a cytidine nucleotide which spans the major groove and alkylates the 7-position of a complementary guanine residue in a targeted strand: see Summerton et al., *J. Mol. Biol.*, 1978, 122, 145–162; *J. Theor. Biology*, 1979, 78, 61–75; and U.S. Pat. No. 4,123,610. The alkylated bases formed under these conditions are quaternary charged species that are subject to rapid chemical degradation via imidazole ring opening followed by cleavage of the targeted strand. Meyer et. al., *J. Am. Chem. Soc.*, 1989, 111, 8517, described attaching an iodo-acetamidopropyl moiety to the 5-position of a thymidine nucleotide of DNA that alkylated the 7-position of a guanine nucleotide at a position two base pairs down the complementary strand.

Cross-linking may also be achieved by hybridization. For example, an N6,N6-ethano-adenine or N4,N4-ethanocytosine alkylates an appropriately positioned nucleophile in a complementary strand. This process has been designed to inactivate the normal function of the targeted DNA either by forming a stable adduct or by hydrolytic or enzymatic cleavage: see Mateucci et al., *Nucleic Acids Res.*, 1986, 14, 7661; *Tetrahedron Letters*, 1987, 28, 2469–2472; Ferentz et al., *J. Am. Chem. Soc.*, 1991, 113, 4000.

A serious deficiency of the early studies using oligonucleotides as antisense agents, particularly in the filed of therapeutics, resided in the use of unmodified oligonucleotides for these purposes. Such unmodified oligonucleotides are degraded by a variety of intracellular and extracellular ubiquitous nucleolytic enzymes, hereinafter referred to as "nucleases."

To enhance the above mechanisms of action of antisense agents, a number of chemical modifications have been introduced into antisense agents, i.e. oligonucleotides and oligonucleotide analogs, to increase their therapeutic activity. Such modifications are designed to modify one or more properties including cellular penetration of the antisense agents, stabilization of the antisense agents to nucleases and other enzymes that degrade or interfere with their structure or activity in the body, enhancement of the antisense agents' binding to targeted RNA, modification of the mode of disruption (terminating event) once the antisense agents are sequence-specifically bound to targeted RNA, or improvement of the antisense agents' pharmacokinetic and pharmacodynamic properties.

To increase the potency of an oligonucleotide antisense agent by increasing its resistance to nucleases, modifications are most often introduced at the sugar-phosphate backbone, particularly on the phosphorus atom. Phosphorothioates, methyl phosphonates, phosphoramidites, and phosphotriesters have been reported to have various levels of resistance to nucleases. Other backbone modifications are disclosed as set forth in U.S. patent applications assigned to a common assignee hereof, entitled "Backbone Modified Oligonucleotide Analogs," Ser. No. 703,619 and "Heteroatomic Oligonucleotide Linkages," Ser. No. 903,160, the disclosures of which are incorporated herein by reference to disclose more fully such modifications.

The phosphorothioate modified oligodeoxynucleotides are of particular use since, as noted above, they are capable of cleaving RNA by activation of RNase H upon hybridization to RNA. Hybridization arrest of RNA function may, however, play some part in their activity.

Other modifications to "wild type" oligonucleotides include functionalizing the nucleoside's naturally occurring sugar. Certain sugar modifications are disclosed as set forth in PCT Patent Application Number PCT\US91\00243, International Publication Number WO 91/10671, assigned to a common assignee hereof, entitled "Compositions and Methods for Detecting and Modulating RNA Activity and Gene Expression," the disclosures of which are incorporated herein by reference to disclose more fully such modifications. Heteroduplexes formed between RNA and oligonucleotides bearing 2'-sugar modifications, e.g. RNA mimics such as 2'-fluoro and 2'-alkoxy, do not support RNase H-mediated cleavage. These modified heteroduplexes assume an A form helical geometry as does RNA-RNA heteroduplexes, which also do not support RNase H cleavage. See Kawasaki, et al., *J. Med. Chem.*, in press 1993; Lesnik, et al., *Biochemistry*, submitted 1993; Inoue, et al., *Nucleic Acids Res.* 1987, 15, 6131.

Further modifications include modification to the heterocyclic portions, rather than to the sugar-phosphate portions, of the nucleosides of an oligonucleotide or oligonucleotide analogue. Substitutions at the N-2, N-6 and C-8 positions of certain purines, such as hypoxanthine, guanine, or adenine have been reported: see, e.g., Harris et al., *J. Am. Chem. Soc.*, 1991, 113, 4328–4329 (displacement of a 2-halogen or a 6-halogen group on a purine within an oligonucleotide to give a modified oligonucleotide wherein the purine ring of one of the nucleotides of the oligonucleotide is substituted at the 2-position or 6-position with phenylgylcinol); Johnson et al., *J. Am. Chem. Soc.*, 1992, 114, 4923–4924 (post synthetic introduction of an 8-fluorenylamino group at the 2-position of deoxyguanosine residues in oligonucleotides via a new protecting group); Lee et al., *Tetrahedron Letters*, 1990, 31, 6773–6776 (introducing a pyrene molecule at the N-2 and N-6 position of purine nucleotides of an oligonucleotide as a model for derivatization with polycyclic aromatic hydrocarbons); Casale et al. *J. Am. Chem. Soc.*, 1990, 112, 5264–5271 (introducing a 9-methyl anthracene group at the N-2 position of a 2'-deoxyguanosine nucleotide of an oligonucleotide causing destabilization of the DNA duplex); Kim et al., *J. Am. Chem. Soc.*, 1992, 114, 5480–5481 (introducing a 6-fluoro purine nucleotide into an oligonucleotide followed by displacement of the fluorine with a polycyclic aromatic amine); Gao et al., *J. Organ. Chem.*, 1992, 57, 6954–6959 (introducing a pentafluorophenyl group, i.e. $-OC_6F_5$, at the N-6 position of deoxyguanosine for post-synthetic modification to 2-aminoadenosine or 6-O-methylguanosine); Gmeiner et al., *Bioorg. Med. Chem. Letters*, 1991, 1, 487–490 (formation of 6-N-(2-cholesteroloxycarboaminethyl) or 6-N-[2-(9-fluorenylcarboamino)ethyl] adenosine moieties via a 6-chloropurine riboside followed by introduction of these derivatized adenosine nucleosides into oligonucleotides).

The common way of functionalizing the C-8 position of purines is from 8-bromoadenosine derivatives. Roduit, et. al., *Nucleosides, Nucleotides*, 1987, 6, 349, displaced an 8-bromo substituent with an N-protected cysteamine derivative to obtain an aminolinker. In a like manner a 2'-deoxyadenosine nucleotide containing an aminolinker at C-8 having fluorescein attached has been incorporated into an oligonucleotide. Biotin was coupled via a disulfide bridge and 4,5',8-trimethylpsoralen was coupled via sulfur and a 5 carbon atom long alkyl linker, also at C-8. See Pieles, et. al., *Nucleic Acids Res.*, 1989, 17, 8967. In a like manner a dansyl group has been introduced at the C-8 via displacement of the 8-bromo group with a diamino linker and coupling of the dansyl functionality to the terminal amine. See Singh, et. al., *Nucleic Acids Res.,* 1990, 18, 3339.

There still remains a great need for antisense agents that are capable of improved specificity and effectiveness both in binding and modulating mRNA or inactivating mRNA without imposing undesirable side effects. Further, heretofore, there has be no suggestion in the art of cross-linkages or methods of cross-linking that do not destroy the strands, that allow suitable conformations, that are useful on various sequences and at various positions within the sequences, or that allow normal ranges of features such as the "tilt" and "propeller twist" features found in naturally occurring nucleic acid duplexes. Accordingly, there also remains a long-felt need for nucleic acid cross-linkers and methods of cross-linking nucleic acids. The present invention addresses these as well as other needs by presenting novel oligonucleotide intermediates based on the core structure of the purine ring system.

SUMMARY OF THE INVENTION

This invention presents novel compounds based on the purine ring system that have utility, inter alia, as intermediates for antisense agents, as diagnostics and as research reagents. In particular, this invention presents novel substituted purines comprising a tether portion and at least one reactive or non-reactive functionality. In particular, this invention provides nucleosides, nucleoside analogs, nucleotides, nucleotide analogs, heterocyclic bases, and heterocyclic base analogs based on the purine ring system; oligonucleotides incorporating the same are also within the ambit of this invention.

The heterocyclic compounds of the invention are adapted for placement of a pendent group, such as an RNA cleaving moiety, cross-linking moiety or other reactive or non-reactive moiety into a site on a purine ring of a nucleotide or nucleoside that is incorporated into an oligonucleotide or oligonucleoside compositions of the invention.

The 2, 6, and 8 position of the purine ring have been found to be exemplary sites for modification including the attachment of pendent groups, such as RNA cleaving moieties, cross-linking moieties as well as other moieties that may enhance pharmacokinetic properties of antisense agents without affecting other properties such as hybridization and RNase H degradation of target RNA. In addition, a enhancement of heteroduplex binding affinity is observed when certain pendent groups are attached to the 2, 6, and 8 positions of the novel purine based compounds of the invention.

As attached to the C-2 and C-8 positions of a purine ring, the pendent groups are believed to protrude into the minor groove of a DNA-RNA heteroduplex and not to affect binding affinities. These positions have also been found to be novel sites for cross-linking with complementary oligonucleotides and oligonucleotide analogs.

In accordance with the invention compounds are provided with the formula:

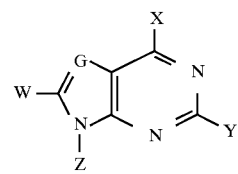

wherein G is $CR_1$ or N; $R_1$ is H or a hydrocarbyl group having from 1 to 6 carbon atoms; X is halogen $NH_2$, OH, $NHR_2Q_1$, or $OR_2Q_1$; wherein said $R_2$ is H or a hydrocarbyl group having from 2 to about 20 carbon atoms, and $Q_1$ comprises at least one reactive or non-reactive functionality; Y is halogen, $NH_2$, H, $R_3Q_2$, or $NHR_3Q_2$, wherein said $R_3$ is H or a hydrocarbyl group having from 2 to about 20 carbon atoms, and $Q_2$ comprises at least one reactive or non-reactive functionality; W is H, $R_4Q_3$, or $NHR_4Q_3$, wherein said $R_4$ is H or a hydrocarbyl group having from 2 to about 20 carbon atoms, $Q_3$ comprises at least one reactive or non-reactive functionality; and Z is H, a nitrogen protecting group, or a sugar moiety.

In certain preferred embodiments, X is $NHR_2Q_1$, where said $Q_1$ is a nitrogen-containing heterocycle, preferably a substituted or unsubstituted imidazole. In a another preferred embodiment, X is $OR_2Q_1$, where said $Q_1$ is a nitrogen-containing heterocycle, preferably a substituted or unsubstituted imidazole. In still another preferred embodiment, W is $R_4Q_3$, where said $Q_3$ is a nitrogen-containing heterocycle, preferably a substituted or unsubstituted imidazole. These compounds may further comprise a sugar moiety, Z, wherein Z is ribose or deoxyribose, preferably deoxyribose.

In another preferred embodiment, X is $NHR_2Q_1$, said $Q_1$ is an amine. In a yet another preferred embodiment, X is $OR_2Q_1$, said $Q_1$ is an amine. In further preferred embodiment, W is $R_4Q_3$, said $Q_3$ is an amine. These compounds may further comprise a sugar moiety, Z, wherein Z is ribose or deoxyribose, preferably deoxyribose.

In still a more preferred embodiment, G is N; X is $NHR_2Q_1$, said $R_2$ is a lower alkane and $Q_1$ is an imidazole; Y is H; and W is H, preferably $R_2$ is an alkane having from about 2 to about 4 carbon atoms, more preferably $R_2$ is propyl. These compounds may further comprise a sugar moiety, Z, wherein Z is ribose or deoxyribose.

In another preferred embodiment, G is N; X is $OR_2Q_1$, said $R_2$ is a lower alkane, preferably having between 2 to about 4 carbon atoms, more preferably propyl; $Q_1$ is an imidazole; Y is $NH_2$; and W is H. These compounds may further comprise a sugar moiety, Z, wherein Z is ribose or deoxyribose.

In another preferred embodiment, G is N; X is $OR_2Q_1$, said $R_2$ is a lower alkane, preferably methyl or propyl; $Q_1$ is phenyl; Y is $NH_2$; and Z is ribose or deoxyribose.

In another preferred embodiment, G is N; X is $OR_2Q_1$, said $R_2$ is propyl; $Q_1$ is nitrophenyl; Z is ribose or deoxyribose; and Y is $NH_2$ or $NHR_3Q_2$, wherein said $R_3$ is isobutyryl and said $Q_2$ is a propyl-imidazole.

In another embodiment, G is N; X is $OR_2Q_1$, said $R_2$ is methyl; $Q_1$ is phenyl; Y is flourine; and Z is ribose or deoxyribose.

In another preferred embodiment, G is N; W is $R_4Q_3$, said $R_4$ is a lower alkane, preferably having between about 2 to about 4 carbon atoms, more preferably propyl, and $Q_3$ is an imidazole; X is OH; and Y is $NH_2$. In another preferred embodiment, G is N; W is $R_4Q_3$, said $R_4$ is a lower alkane, preferably having between about 2 to about 4 carbon atoms, more preferably propyl, and $Q_3$ is an imidazole; X is $NH_2$;

and Y is H. These compounds may further comprise a sugar moiety, Z, wherein Z is ribose or deoxyribose.

In yet another preferred embodiment, G is N; X is $NHR_2Q_1$, said $R_2$ is H and $Q_1$ is an alkane having from about 2 up to about 20 carbon atoms; Y is H; and W is H. In another preferred embodiment, G is N; X is $OR_2Q_1$, said $R_2$ is H and $Q_1$ is an alkane having from about 2 up to about 20 carbon atoms; Y is $NH_2$; and W is H. In still another preferred embodiment, G is N; W is $R_4Q_3$, said $R_4$ is H and $Q_3$ is an alkane having from about 2 up to about 20 carbon atoms; X is OH; and Y is $NH_2$. In another preferred embodiment, G is N; W is $R_4Q_3$, said $R_4$ is H and $Q_3$ is an alkane having from about 2 up to about 20 carbon atoms; X is $NH_2$; and Y is H. These compounds may further comprise a sugar moiety, Z, wherein Z is ribose or deoxyribose.

In a further preferred embodiment, G is N; X is $NHR_2Q_1$, said $R_2$ is an alkane and $Q_1$ is an amine, wherein said amine comprises $NH_2$, polyalkylamine, aminoalkylamine, hydrazine (—NH—NH—), hydroxylamine (—NH—OH), semicarbazide (—NH—C(O)—NH—$NH_2$), thiosemicarbazide (—NH—C(S)—NH—$NH_2$), hydrazone (—N=NH), or hydrazide (—C—(O)—NH—$NH_2$); Y is H; and W is H. These compounds may further comprise a sugar moiety, Z, wherein Z is ribose or deoxyribose.

In another preferred embodiment, G is N; X is $OR_2Q_1$, said $R_2$ is an alkane and $Q_1$ is an amine, wherein said amine comprises $NH_2$, polyalkylamine, aminoalkylamine, hydrazine (—NH—NH—), hydroxylamine (—NH—OH), semicarbazide (—NH—C(O)—NH—$NH_2$), thiosemicarbazide (—NH—C(S)—NH—$NH_2$), hydrazone (—N=NH), or hydrazide (—C—(O)—NH—$NH_2$); Y is $NH_2$; and W is H. These compounds may further comprise a sugar moiety, Z, wherein Z is ribose or deoxyribose.

In a further embodiment, G is N; W is $R_4Q_3$, said $R_4$ is an alkane and $Q_3$ is an amine, wherein said amine comprises $NH_2$, polyalkylamine, aminoalkylamine, hydrazine (—NH—NH—), hydroxylamine (—NH—OH), semicarbazide (—NH—C(O)—NH—$NH_2$), thiosemicarbazide (—NH—C(S)—NH—$NH_2$), hydrazone (—N=NH), or hydrazide (—C—(O)—NH—$NH_2$); Y is $NH_2$; and X is OH. In another embodiment, G is N; W is $R_4Q_3$, said $R_4$ is an alkane and $Q_3$ is an amine, wherein said amine comprises $NH_2$, polyalkylamine, aminoalkylamine, hydrazine (—NH—NH—), hydroxylamine (—NH—OH), semicarbazide (—NH—C(O)—NH—$NH_2$), thiosemicarbazide (—NH—C(S)—NH—$NH_2$), hydrazone (—N=NH), or hydrazide (—C—(O)—NH—$NH_2$); Y is H; and X is $NH_2$. These compounds may further comprise a sugar moiety, Z, wherein Z is ribose or deoxyribose.

In certain other preferred embodiments, G is N; X is $NHR_2Q_1$, said $R_2$ is an alkane and $Q_1$ is a thiol group, halogen, alkoxy group, aldehyde, alcohol, or ketone; Y is H; and W is H. In another preferred embodiment, G is N; X is $OR_2Q_1$, said $R_2$ is a lower alkane and $Q_1$ is a thiol group, halogen, alkoxy group, aldehyde, alcohol, or ketone; Y is $NH_2$; and W is H. These compounds may further comprise a sugar moiety, Z, wherein Z is ribose or deoxyribose.

In further preferred embodiments, G is N; W is $R_4Q_3$, said $R_4$ is a lower alkane and $Q_3$ is a thiol group, halogen, alkoxy group, aldehyde, alcohol, or ketone; Y is $NH_2$; and X is OH. In another preferred embodiment, G is N; W is $R_4Q_3$, said $R_4$ is a lower alkane and $Q_3$ is a thiol group, halogen, alkoxy group, aldehyde, alcohol, or ketone; Y is H; and X is $NH_2$. These compounds may further comprise a sugar moiety, Z, wherein Z is ribose or deoxyribose.

Also provided are compounds according to the invention further comprising a phosphate group at the 3' position of the sugar moiety, wherein said sugar moiety is preferably ribose or deoxyribose; and the phosphate group may be a native phosphate or a modified phosphate; where said modified phosphate is preferably a methylphosphonate, phosphorothioate, phosphorodithioate, phosphoramidite, or phosphorotriester.

Also in accordance with the invention are provided mixed sequence oligonucleotides having at least one compound in accordance with the invention.

Also in accordance with preferred embodiments of the invention are provided oligonucleotides for affecting RNase H cleavage of RNA comprising a first oligonucleotide region and a second nucleotide region; together said first and said second region of a nucleotide sequence essentially complementary to at least a portion of said RNA; said first region including at least one nucleotide in accordance with the compounds of the invention; and said second region including a plurality of consecutive phosphorothioate linked nucleotides having a 2'-deoxy-erythro-pentofuranosyl sugar moiety. In another preferred embodiment, an oligonucleotide further comprises a third region of said oligonucleotide, said third region including at least one nucleotide in accordance with the compounds of the invention; and wherein said second region is positioned in said oligonucleotide between said first and third regions.

Also in accordance with the invention there are provided sequence-specific, covalently cross-linked nucleic acids comprising:

a first oligonucleotide sequence region and a second oligonucleotide sequence region, wherein said first region includes at least one nucleotide of the formula:

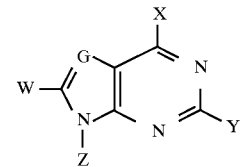

wherein G is $CR_5$ or N; $R_5$ is H or a hydrocarbyl group having from 1 to 6 carbon atoms; X is halogen $NH_2$, OH, $NHR_6Q_1$, $OR_6Q_1$, NHJ, OJ or SJ wherein said $R_6$ is H or a hydrocarbyl group having from 2 to about 20 carbon atoms, $Q_1$ comprises at least one reactive or non-reactive functionality and J comprises a space spanning group $R_7$ and an active functional group $Q_4$; Y is halogen, $NH_2$, H, SH, OH, NHJ, OJ or SJ where J comprises a space spanning group $R_7$ and an active functional group $Q_4$; W is H, NHK, OK or SK where K comprises a space spanning group $R_7$ and an active non-psoralen functional group $Q_5$; Z is H, a nitrogen protecting group, or a sugar moiety; and providing that at least one of said X or Y groups is NHJ, OJ or SJ, or at least one of said W groups is NHK, OK or SK; said second sequence region including a second nucleotide capable of covalently bonding with said J group or said K group of said first nucleotide; and a covalent cross-linkage between said first and said second nucleotides.

In certain preferred embodiments, both the first and the second nucleotides comprise a nucleotide of said formula, and said covalent linkage is between said nucleotides of said formula.

In certain preferred embodiments, the group J or K on the first nucleotide includes a first space-spanning group having a first active functional group, the group J or K on the second nucleotide includes a second space-spanning group having a second active functional group and the covalent cross-linkage is between the first and second active functional groups.

In preferred embodiments, the space-spanning group $R_7$ is from about 8 to about 13 atoms in length and the said groups $Q_4$ and $Q_5$ are, independently, a thiol, an aldehyde, a protected aldehyde, an aldehyde precursor, an amine, hydrazine, hydroxylamine, semicarbazide, thiosemicarbazide, hydrazide, alcohol, or alkoxy. In certain embodiments of the invention, the first sequence region and second sequence regions are on a single oligonucleotide strand. In further embodiments the first and second sequence regions are on different strands. It is preferred that the first sequence region and said second sequence region be complementary to and specifically hybridizable with one another.

In other more preferred embodiments, the group J is at the position X; the space-spanning group $R_7$ is from about 8 to about 13 atoms in length and said group $Q_4$ is a thiol, an aldehyde, a protected aldehyde, an aldehyde precursor, $NH_2$, polyalkylamine, aminoalkylamine, hydrazine (—NH—NH—), hydroxylamine (—NH—OH), semicarbazide (—NH—C(O)—NH—$NH_2$), thiosemicarbazide (—NH—C(S)—NH—$NH_2$), hydrazone (—N=NH), hydrazide (—C(O)—NH—$NH_2$), alcohol, or alkoxy. In one embodiment the first sequence region and second sequence regions are on a single oligonucleotide strand. In a further embodiment the first and second sequence regions are on different strands. It is preferred that the first sequence region and said second sequence region be complementary to and specifically hybridizable with one another.

In other preferred embodiments, the group J is at the position Y; the space-spanning group $R_7$ is from about 8 to about 13 atoms in length and said group $Q_4$ is a thiol, an aldehyde, a protected aldehyde, an aldehyde precursor, an amine, hydrazine, hydroxylamine, semicarbazide, thiosemicarbazide, hydrazide, alcohol, or alkoxy. In one embodiment the first sequence region and second sequence regions are on a single oligonucleotide strand. In a further embodiment the first and second sequence regions are on different strands. It is preferred that the first sequence region and said second sequence region be complementary to and specifically hybridizable with one another.

In still other preferred embodiments, the group K is at the position W; the space-spanning group $R_7$ is from about 8 to about 13 atoms in length and said group $Q_5$ is a thiol, an aldehyde, a protected aldehyde, an aldehyde precursor, an amine, hydrazine, hydroxylamine, semicarbazide, thiosemicarbazide, hydrazide, alcohol, or alkoxy. In one embodiment the first sequence region and second sequence regions are on a single oligonucleotide strand. In a further embodiment the first and second sequence regions are on different strands. It is preferred that the first sequence region and said second sequence region be complementary to and specifically hybridizable with one another.

In certain other more preferred embodiments, wherein the first nucleotide is located in a first nucleotide sequence and the second nucleotide is located in a second nucleotide sequence, and the second nucleotide sequence is complementary to and hybridizable with the first nucleotide sequence, and the first and second nucleotide sequences are located on a single strand of the oligonucleotide with the second nucleotide sequence located on the oligonucleotide at a distance separated from the first nucleotide sequence sufficient to allow the oligonucleotide to assume a conformation wherein the first and second nucleotide sequences are mutually aligned with and specifically hybridized with one another.

In another preferred embodiment, the first nucleotide is located in a first nucleotide sequence and the second nucleotide is located in a second nucleotide sequence, and the first and second nucleotide sequences are located on a single strand of an oligonucleotide with the second nucleotide sequence located on the oligonucleotide at a non-hybridizable position with respect to the first nucleotide sequence and at a distance from the first nucleotide sequence sufficient to allow the oligonucleotide to assume a conformation such that the first and second nucleotide sequences are located in spatial proximity with each other.

In certain other preferred embodiments the first nucleotide is located in a first nucleotide sequence and the second nucleotide is located in a second nucleotide sequence, the second nucleotide sequence is complementary to and specifically hybridizable with the first nucleotide sequence and the first and second nucleotide sequences are located on different oligonucleotide strands.

DETAILED DESCRIPTION OF THE INVENTION

This invention presents novel heterocyclic compounds based on a purine ring system which may be used as intermediates for oligonucleotides. This invention provides nucleosides, nucleoside analogs, nucleotides, nucleotide analogs, heterocyclic bases, heterocyclic base analogs, and oligonucleotides incorporating the same.

The novel compounds of the invention are based on the purine ring system, comprising a heterocyclic purine-base portion, at least one reactive or non-reactive functionality, and a tether portion for attaching the functionalities to the balance of the compound. The 2, 6, and 8 positions of the purine ring have been found to be particularly useful as the point of attachment for reactive and non-reactive functionalities. Attachment at these positions can enhance the oligonucleotides and oligonucleotide analogs' ability to modulate RNA activity and can also improve the antisense agents' transport properties. When non-reactive functionalities are placed at these positions, the non-reactive functionalities' utility lies, in part, in their ability to improve the pharmacodynamic or pharmacokinetic properties of the antisense agents, whether or not these functionalities may also play a role in initiating cleaving reactions. These attributes and others make these compounds useful antisense agent intermediates.

Selection of the functional sites on the base units is made in part taking into consideration the design of compositions for sequence-specific destruction or modulation of targeted RNA. The half-life of the formed duplex is likely to be greatly affected by the positioning of the tethered group that connects the reactive functionality to the base unit. Thus consideration is given in choosing the tether functionality so as to not adversely interfere with Watson-Crick base pair hydrogen bonding rules of the antisense agent to a target strand.

The compounds of the invention may have at least one reactive functionality or other moiety appended thereto capable of interacting with, via cleaving or cross-linking, an RNA. It is not necessary to tether more than one, two, or a relatively small number of pendent groups, such as RNA cleaving functionalities, to antisense agents in accordance with this invention to provide the invention's benefits. An RNA cleaving moiety will preferably be tethered to a relatively small proportion, generally only one or two, of the subunits of the antisense agents of the invention. In other embodiments of the invention, however, substantially all of the nucleotides in an oligonucleotide can be modified to include one or more pendent groups such as RNA cleaving moieties.

The compounds of the invention may be used to prepare desired oligonucleotides and oligonucleotide analogs; these oligonucleotides and oligonucleotide analogs are also within the ambit of this invention.

Incorporation of these novel compounds into antisense agents improves their pharmacokinetic and pharmacodynamic properties, improves their resistance to nucleases, facilitates anti-sense and non-antisense therapeutic uses, diagnostic uses and research reagent uses, improves their binding capabilities without adverse concomitant interference with the Watson-Crick binding, and enhances their penetration into cells.

In accordance with the teachings of this invention, RNA-RNA, DNA-DNA or DNA-RNA type duplexes can be covalently cross-linked via a space-spanning group attached to nucleotide units at desired attachment sites. Thus novel covalently cross-linked oligonucleotide or oligonucleotide analog strands are also within the ambit of the invention. Preferably such strands are "duplexed" or "complementary" along at least a portion of their length. In the context of this invention the terminology "duplex strands" or "complementary strands" or like terminology refers in a first instance to two separate strands wherein at least one nucleotide or nucleotide sequence on one of the strands is complementary to and specifically hybridizable with an opposing nucleotide or nucleotide sequence on the other strand. In a second instance, this terminology refers to two sections or sequence regions of a single strand that are spaced from one another by a distance sufficient for the strand to fold onto itself and permit hybridization of complementary nucleotides in the respective sequence regions. Folded, self-hybridizing, single strands form hairpin loops, stem loops, interior loops, or bulge type structures as a result of such hybridization.

In the context of this invention, a "nucleoside" is a nitrogenous heterocyclic base linked to a pentose sugar, either a ribose, deoxyribose, or derivatives or analogs thereof. The term "nucleotide" means a phosphoric acid ester of a nucleoside comprising a nitrogenous heterocyclic base, a pentose sugar, and one or more phosphate or other backbone forming groups; it is the monomeric unit of an oligonucleotide. The term "oligonucleotide" refers to a plurality of joined nucleotide units formed in a specific sequence from naturally occurring heterocyclic bases and pentofuranosyl equivalent groups joined through phosphodiester or other backbone forming groups. Nucleotide units may include the common bases such as guanine, adenine, cytosine, thymine, or derivatives thereof. The pentose sugar may be deoxyribose, ribose, or groups that substitute therefor.

The term "antisense agents" as used in the context of this invention encompasses oligonucleotides and oligonucleotide analogs. In the context of this invention, phosphate derivatives include phosphorothioates, methyl phosphonates, phosphoramidites, phosphotriesters, and any other groups known to those skilled in the art.

"Modified base," "base analog," "modified nucleoside," "nucleotide analog," or "modified nucleotide," in the context of this invention refer to moieties that function similarly to their naturally occurring counterparts but have been functionalized to change their properties.

"Sugar moiety" as used in the context of this invention refers to naturally occurring sugars, such as ribose or deoxyribose, and sugars and non-sugar analogs that have been functionalized to change certain properties.

"Oligonucleotide analogs" or "modified oligonucleotides" as used in connection with this invention, refer to compositions that function similarly to natural oligonucleotides but that have non-naturally occurring portions. Oligonucleotide analogs or modified oligonucleotides may have altered sugar moieties, altered bases, both altered sugars and bases, or altered inter-sugar linkages, such as, for example, phosphorothioates and other sulfur containing species which are known for use in the art. In the context of the invention, "improved pharmacodynamic property" means improved antisense agent uptake, enhanced antisense agent resistance to degradation, and/or strengthened sequence-specific hybridization with RNA. "Improved pharmacokinetic property" means improved oligonucleotide uptake, distribution, metabolism or excretion.

The hydrocarbyl groups disclosed and claimed herein are the linkers, space-spanning groups, or tethers that attach functionalities (such as nucleophiles or electrophiles) to the purine-based compounds of the invention. A hydrocarbyl compound, as used herein, means a straight, branched, or cyclic carbon and hydrogen containing compound. The space spanning groups are composed of carbon atoms or of carbon atoms plus one or more heteroatoms, such as nitrogen oxygen, or sulfur, i.e., internally interrupted. In the context of this invention, a straight chain compound means an open chain compound, such as an aliphatic compound, including alkyl, alkenyl, or alkynyl compounds. Lower alkyl, alkenyl, or alkynyl as used herein means hydrocarbyl compounds from about 1 to about 6 carbon atoms. A branched compound, as used herein, comprises a straight chain compound, such as an alkyl, alkenyl, alkynyl, which has further straight or branched chains attached to the carbon atoms of the straight chain. A cyclic compound, as used herein, refers to closed chain compounds, i.e., a ring of carbon atoms, such as a cyclic aliphatic or aromatic compounds. The hydrocarbyl compounds noted above may be substituted or unsubstituted. In the context of this invention, substituted or unsubstituted means that the hydrocarbyl compounds may have any one of a variety of substituents, in replacement, for example, of one or more hydrogen atoms in the compound, or may have no substituents. Suitable substituents will be readily apparent to those skilled in the art, in view of the present disclosure. The straight, branched, or cyclic compounds may be internally interrupted (for example, alkylalkoxy or heterocyclic compounds). In the context of this invention, internally interrupted means that the carbon chains may be interrupted with heteroatoms such as O, N, or S. However, if desired, the carbon chain may have no heteroatoms.

"Pendent groups," as used herein, refers to both reactive and non-reactive functionalities. "Reactive functionality," as used herein, means a moiety that interacts with mRNA in some manner to more effectively inhibit translation of the mRNA into protein. For example, such a moiety may act as an RNA cleaving agent. A "non-reactive functionality," as used herein, means a functional group that may not possess a reactive portion or may not initiate chemical reactions, but rather enhances the antisense agents' pharmacodynamic and pharmacokinetic properties, whether or not it plays any role in RNA cleavage or cross-linking. When "terminal end" is used in reference to the reactive or non-reactive functionality, this term means the end not attached to the purine core.

Further in the context of this invention, it will be recognized that the terms "cross-linkage", "cross-link," "cross-linkers," or "cross-linking" specifically exclude those portions of the oligonucleotide structure that linearly connect individual nucleoside subunits or nucleoside-like, modified subunits (i.e., those portions that connect the nucleoside units in the sequence that defines the primary structure of the antisense agent). Thus, "cross-linkage," "cross-link," "cross-linker," or "cross-linking" exclude native phosphodiester linkages that connect nucleosides, as well as analogous, non-native internucleoside linkages such as phosphorothioate, phosphorodithioate methyl phosphonate, phosphotriester, phosphoramidate, —O—CH$_2$—CH$_2$—O— and other non-phosphate linkages used in place of phosphodiester inter-nucleoside linkages. The terms "cross-linkage", "cross-link" or "cross-linking" as used in the context of this invention refer to "additional" linkages created across a single oligonucleotide or oligonucleotide analog strand or several oligonucleotide or oligonucleotide analog strands to hold the strand or strands in secondary or other, higher-ordered structures. Primary, secondary, and higher-order structures are as defined in standard reference texts such as *Nucleic Acids In Chemistry And Biology*, (eds. Blackburn & Gait, Oxford University Press, New York, 1991).

Cross-linking is employed in accordance with the present invention to fix separate oligonucleotide or oligonucleotide analog strands in duplex structures or to fix a single oligonucleotide or oligonucleotide analog strand in hairpin loops, stem loops, interior loops, bulges or other similar higher-order structures. Such fixation is believed to confer nuclease resistance to antisense agents and to optimize structure-dependent function. Fixing a strand or strands in a duplex structure also can disrupt the normal function of single-strand nucleic acid-binding proteins by forming nuclease-resistant mimics of the proteins' binding receptors. Fixing a strand or strands in set secondary structures also makes it possible to mimic the RNA secondary structures found in diseased cells, particularly cells infected with viruses and retroviruses. A detailed delineation of such RNA mimicry is disclosed in Application PCT/US91/01822, filed Mar. 19, 1991, entitled Reagents and Methods For Modulating Gene Expression Through RNA Mimicry, assigned to the same assignee as this application, the disclosures of which are herein incorporated by reference in their entirety.

The "fixing" of multiple oligonucleotide or oligonucleotide analog strands or a single oligonucleotide or oligonucleotide analog strand in defined secondary or other higher-order structure is achieved in accordance with this invention by cross-linking the oligonucleotide or oligonucleotide analog strands.

In one aspect of the invention, the compounds of the invention have the following general formula:

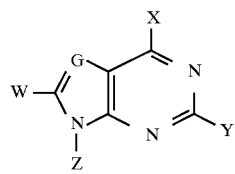

wherein G is CR$_1$ or N;

R$_1$ is H or a hydrocarbyl group having from 1–6 carbon atoms;

X is halogen, OH, NH$_2$, NHR$_2$Q$_1$, or OR$_2$Q$_1$, wherein said R$_2$ is H or a hydrocarbyl group having from 2 to about 20 carbon atoms, and Q$_1$ comprises at least one reactive or non-reactive functionality;

Y is halogen, NH$_2$, H, R$_3$Q$_2$, or NHR$_3$Q$_2$, wherein said R$_3$ is H or a hydrocarbyl group having from 2 to about 20 carbon atoms, and Q$_2$ comprises at least one reactive or non-reactive functionality;

W is H, R$_4$Q$_3$, or NHR$_4$Q$_3$, wherein said R$_4$ is H or a hydrocarbyl group having from 2 to about 20 carbon atoms, and Q$_3$ comprises at least one reactive or non-reactive functionality; and Z is H, a nitrogen protecting group, or a sugar moiety.

In certain preferred embodiments, X is NHR$_2$Q$_1$, where said Q$_1$ is a nitrogen-containing heterocycle, preferably a substituted or unsubstituted imidazole. In a another preferred embodiment, X is OR$_2$Q$_1$, where said Q$_1$ is a nitrogen-containing heterocycle, preferably a substituted or unsubstituted imidazole. In still another preferred embodiment, W is R$_4$Q$_3$, where said Q$_3$ is a nitrogen-containing heterocycle, preferably a substituted or unsubstituted imidazole. These compounds may further comprise a sugar moiety, Z, wherein Z is ribose or deoxyribose, preferably deoxyribose.

In another preferred embodiment, X is NHR$_2$Q$_1$, said Q$_1$ is an amine. In a yet another preferred embodiment, X is OR$_2$Q$_1$, said Q$_1$ is an amine. In further preferred embodiment, W is R$_4$Q$_3$, said Q$_3$ is an amine. These compounds may further comprise a sugar moiety, Z, wherein Z is ribose or deoxyribose, preferably deoxyribose.

In still a more preferred embodiment, G is N; X is NHR$_2$Q$_1$, said R$_2$ is a lower alkane and Q$_1$ is an imidazole; Y is H; and W is H, preferably R$_2$ is an alkane having from about 2 to about 4 carbon atoms, more preferably propyl. These compounds may further comprise a sugar moiety, Z, wherein Z is ribose or deoxyribose, preferably deoxyribose.

In another preferred embodiment, G is N; X is OR$_2$Q$_1$, said R$_2$ is a lower alkane, preferably having between 2 to about 4 carbon atoms, more preferably propyl; Q$_1$ is an imidazole; Y is NH$_2$; and W is H. In another preferred embodiment, G is N; X is OR$_2$Q$_1$, said R$_2$ is a lower alkane, preferably having between 2 to about 4 carbon atoms, more preferably propyl; Q$_1$ is phenyl; Y is NH$_2$; and W is H. In another preferred embodiment, G is N; X is OR$_2$Q$_1$, said R$_2$ is a lower alkane, preferably having between 2 to about 4 carbon atoms, more preferably propyl; Q$_1$ is nitrophenyl; Y is NH$_2$; and W is H. These compounds may further comprise a sugar moiety, Z, wherein Z is ribose or deoxyribose, preferably deoxyribose.

In another preferred embodiment, G is N; W is R$_4$Q$_3$, said R$_4$ is a lower alkane, preferably having between about 2 to about 4 carbon atoms, more preferably propyl, and Q$_3$ is an imidazole; X is OH; and Y is NH$_2$. In another preferred embodiment, G is N; W is R$_4$Q$_3$, said R$_4$ is a lower alkane, preferably having between about 2 to about 4 carbon atoms, more preferably propyl, and Q$_3$ is an imidazole; X is NH$_2$; and Y is H. These compounds may further comprise a sugar moiety, Z, wherein Z is ribose or deoxyribose, preferably deoxyribose.

In another preferred embodiment, G is N; X is NHR$_2$Q$_1$, said R$_2$ is H and Q$_1$ is an alkane having from about 2 up to about 20 carbon atoms; Y is H; and W is H. In another preferred embodiment, G is N; X is OR$_2$Q$_1$, said R$_2$ is H and Q$_1$ is an alkane having from about 2 up to about 20 carbon atoms; Y is NH$_2$; and W is H. In still another preferred embodiment, G is N; W is R$_4$Q$_3$, said R$_4$ is H and Q$_3$ is an alkane having from about 2 up to about 20 carbon atoms; X is OH; and Y is NH$_2$. In another preferred embodiment, G is N; W is R$_4$Q$_3$, said R$_4$ is H and Q$_3$ is an alkane having from about 2 up to about 20 carbon atoms; X is NH$_2$; and Y is H. These compounds may further comprise a sugar moiety, Z, wherein Z is ribose or deoxyribose, preferably deoxyribose.

In a further preferred embodiment, G is N; X is NHR$_2$Q$_1$, said R$_2$ is an alkane and Q$_1$ is an amine, wherein said amine comprises NH$_2$, polyalkylamine, aminoalkylamine, hydrazine (—NH—NH—), hydroxylamine (—NH—OH), semicarbazide (—NH—C(O)—NH—NH$_2$), thiosemicarbazide (—NH—C(S)—NH—NH$_2$), hydrazone (—N=NH), or hydrazide (—C—(O)—NH—NH$_2$); Y is H; and W is H. These compounds may further comprise a sugar moiety, Z, wherein Z is ribose or deoxyribose, preferably deoxyribose.

In another preferred embodiment, G is N; X is OR$_2$Q$_1$, said R$_2$ is an alkane and Q$_1$ is an amine, wherein said amine comprises NH$_2$, polyalkylamine, aminoalkylamine, hydrazine (—NH—NH—), hydroxylamine (—NH—OH), semicarbazide (—NH—C(O)—NH—NH$_2$), thiosemicarbazide (—NH—C(S)—NH—NH$_2$), hydrazone (—N=NH), or hydrazide (—C—(O)—NH—NH$_2$); Y is NH$_2$; and W is H. These compounds may further comprise a sugar moiety, Z, wherein Z is ribose or deoxyribose, preferably deoxyribose.

In a further embodiment, G is N; W is R$_4$Q$_3$, said R$_4$ is an alkane and Q$_3$ is an amine, wherein said amine comprises NH$_2$, polyalkylamine, aminoalkylamine, hydrazine (—NH—NH—), hydroxylamine (—NH—OH), semicarbazide (—NH—C(O)—NH—NH$_2$), thiosemicarbazide (—NH—C(S)—NH—NH$_2$), hydrazone (—N=NH), or hydrazide (—C—(O)—NH—NH$_2$); Y is NH$_2$; and X is OH. In another embodiment, G is N; W is R$_4$Q$_3$, said R$_4$ is an alkane and Q$_3$ is an amine, wherein said amine comprises NH$_2$, polyalkylamine, aminoalkylamine, hydrazine (—NH—NH—), hydroxylamine (—NH—OH), semicarbazide (—NH—C(O)—NH—NH$_2$), thiosemicarbazide (—NH—C(S)—NH—NH$_2$), hydrazone (—N=NH), or hydrazide (—C—(O)—NH—NH$_2$); Y is H; and X is NH$_2$. These compounds may further comprise a sugar moiety, Z, wherein Z is ribose or deoxyribose, preferably deoxyribose.

In certain other preferred embodiments, G is N; X is NHR$_2$Q$_1$, said R$_2$ is an alkane and Q$_1$ is a thiol group, halogen, alkoxy group, aldehyde, alcohol, or ketone; Y is H; and W is H. In another preferred embodiment, G is N; X is OR$_2$Q$_1$, said R$_2$ is a lower alkane and Q$_1$ is a thiol group, halogen, alkoxy group, aldehyde, alcohol, or ketone; Y is NH$_2$; and W is H. These compounds may further comprise a sugar moiety, Z, wherein Z is ribose or deoxyribose, preferably deoxyribose.

In further preferred embodiments, G is N; W is R$_4$Q$_3$, said R$_4$ is a lower alkane and Q$_3$ is a thiol group, halogen, alkoxy group, aldehyde, alcohol, or ketone; Y is NH$_2$; and X is OH. In another preferred embodiment, G is N; W is R$_4$Q$_3$, said R$_4$ is a lower alkane and Q$_3$ is a thiol group, halogen, alkoxy group, aldehyde, alcohol, or ketone; Y is H; and X is NH$_2$. These compounds may further comprise a sugar moiety, Z, wherein Z is ribose or deoxyribose, preferably deoxyribose.

The hydrocarbyl groups (R$_n$) may serve as tethers, space-spanning groups, or linkers for attaching reactive or non-reactive functionalities to the purine ring system of the compounds of the invention. The hydrocarbyl groups, R$_n$, suitable for practicing this invention may be alkyl, alkenyl, aryl, or cyclic groups. Alkyl groups of the invention include, but are not limited to, straight and branched chained alkyls such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl straight chained alkyl groups; 2-methylpropyl, 2-methyl-4-ethylbutyl, 2,4-diethylpropyl, 3-propylbutyl, 2,8-dibutyldecyl, 6,6-dimethyloctyl, 6-propyl-6-butyloctyl, 2-methylbutyl, 2-methylpentyl, 3-methylpentyl, 2-ethylhexyl, 3-penten-2-one, 3-methyl-2-butanol, 2-cyanooctyl, 3-methoxy-4-heptanal, 3-nitrobutyl, 4-isopropoxydodecyl, 4-azido-2-nitrodecyl, 5-mercaptononyl, 4-amino-1-pentenyl branched or substituted groups; allyl, crotyl, propargyl, 2-pentenyl unsaturated groups; 4-methylenebenzyl, 1,4-naphthyl, 2,7-anthracyl and 2,6-phenanthryl aryl or aralkyl groups. While propyl groups have been found to be highly useful R$_n$ groups, other alkyl groups, including methyl, ethyl, butyl and others up to about octyl, can find utility; preferred are C$_2$ to C$_4$ alkyl with propyl being most preferred. Ethylene, propylene and other glycols and polyamines are also useful.

Other tether, linkers, or space-spanning groups include, without limitation, polyamines, polyamides, polyesters, polyethylene glycols polyether (polyalkoxy-alkyl) and heterocyclic groups. The amine functionalities can be primary amines, hydrazines, semicarbazides, thiosemicarbazides or similar nitrogenous species.

Alkenyl groups useful in the invention include, but are not limited to, unsaturated moieties derived from the above alkyl groups including but not limited to vinyl, allyl, crotyl, and propargyl.

Useful aryl groups include, but are not limited to, phenyl, tolyl, benzyl, naphthyl, anthracyl, phenanthryl, and xylyl.

Any of the hydrocarbyl groups, that is, the straight, branched, or cyclic alkyl, alkenyl, or alkynyl groups discussed above may be internally interrupted with heteroatoms, such as O, N, or S; however, this is not required. For example, polyoxyhydrocarbyl or polyaminohydrocarbyl compounds are fully contemplated within the ambit of the invention. Some further examples include those where hydrocarbyl groups may comprise a polyhydric alcohol, such as —CH$_2$—(CHOH)$_n$—CH$_2$OH, wherein n=1 to 5. Alternatively, by way of example, hydrocarbyl groups may comprise an ether, such as —CH$_2$(CHOH)nCH$_2$O(CH$_2$)$_m$, where n=1 to 10 and m=1 to 10.

The hydrocarbyl groups may be further substituted. Substituent groups for the above include, but are not limited to, other alkyl, haloalkyl, alkenyl, alkoxy, thioalkoxy, haloalkoxy and aryl groups as well as amino, azido, carboxy, cyano, halogen, heterocycles, hydroxyl, keto, mercapto, nitrates, nitrites, nitro, nitroso, nitrile, sulfides, sulfones, sulfoxides, trifluoromethyl, O-alkyl, S-alkyl, NH-alkyl, silyl, intercalators, conjugates, polyamines, polyamides, polyethylene glycols, polyethers, groups that enhance the pharmacodynamic properties of oligonucleotides and groups that enhance the pharmacokinetic properties of oligonucleotides. Typical intercalators and conjugates include cholesterols, phospholipids, biotin, phenanthroline, phenazine, phenanthridine, anthraquinone, acridine, fluoresceins, rhodamines, coumarins, and dyes. Halogens include fluorine, chlorine, bromine and iodine. Other suitable substituent groups will be apparent to those skilled in the art and may be used without departing from the spirit of the invention.

Representative examples of the hydrocarbyl groups are, without limitation, C$_1$–C$_{20}$ straight chain alkyl, C$_1$–C$_{20}$ straight chain O-alkyl, C$_1$–C$_{20}$ straight chain S-alkyl, C$_1$–C$_{20}$ straight chain NH-alkyl, C$_1$–C$_{20}$ straight chain substituted alkyl, C$_1$–C$_{20}$ straight chain substituted O-alkyl, C$_1$–C$_{20}$ straight chain substituted S-alkyl, C$_1$–C$_{20}$ straight chain substituted NH-alkyl, C$_2$–C$_{20}$ branched chain alkyl, C$_2$–C$_{20}$ branched chain O-alkyl, C$_2$–C$_{20}$ branched chain S-alkyl, C$_2$–C$_{20}$ branched chain NH-alkyl, C$_2$–C$_{20}$ branched chain substituted alkyl, C$_2$–C$_{20}$ branched chain substituted O-alkyl, C$_2$–C$_{20}$ branched chain substituted S-alkyl, C$_2$–C$_{20}$ branched chain substituted NH-alkyl, C$_2$–C$_{20}$ straight chain alkenyl, C$_2$–C$_{20}$ straight chain O-alkenyl, C$_2$–C$_{20}$ straight chain S-alkenyl, C$_2$–C$_{20}$ straight chain NH-alkenyl, C$_2$–C$_{20}$ straight chain substituted alkenyl, C$_2$–C$_{20}$ straight chain substituted O-alkenyl, C$_2$–C$_{20}$ straight chain substituted S-alkenyl, $C_2$–$C_{20}$ straight chain substituted NH-alkenyl, $C_3$–$C_{20}$ branched chain alkenyl, $C_3$–$C_{20}$ branched chain O-alkenyl, $C_3$–$C_{20}$ branched chain S-alkenyl, $C_3$–$C_{20}$ branched chain NH-alkenyl, $C_3$–$C_{20}$ branched chain substituted alkenyl, $C_3$–$C_{20}$ branched chain substituted O-alkenyl, $C_3$–$C_{20}$ branched chain substituted S-alkenyl, $C_3$–$C_{20}$ branched chain substituted NH-alkenyl, $C_2$–$C_{20}$ straight chain alkyne, $C_2$–$C_{20}$ straight chain O-alkyne, $C_2$–$C_{20}$ straight chain S-alkyne, $C_2$–$C_{20}$ straight chain NH-alkyne, $C_2$–$C_{20}$ straight chain substituted alkyne, $C_2$–$C_{20}$ straight chain substituted O-alkyne, $C_2$–$C_{20}$ straight chain substituted S-alkyne, $C_2$–$C_{20}$ straight chain substituted NH-alkyne, $C_3$–$C_{20}$ branched chain alkyne, $C_2$–$C_{20}$ branched chain O-alkyne, $C_3$–$C_{20}$ branched chain S-alkyne, $C_3$–$C_{20}$ branched chain NH-alkyne, $C_3$–$C_{20}$ branched chain substituted alkyne, $C_3$–$C_{20}$ branched chain substituted O-alkyne, $C_3$–$C_{20}$ branched chain substituted S-alkyne, $C_3$–$C_{20}$ branched chain substituted NH-alkyne, polyamine, polyamide, polyester, polyethylene glycol, aryl, aralkyl or heterocyclic.

The following compounds are useful for forming compounds having amine-functionalized space-spanning groups and are commercially available from Aldrich Chemical Co., Inc., Milwaukee, Wis.: N-(2-bromoethyl)phthalimide, N-(3-bromopropyl)phthalimide and N-(4-bromobutyl) phthalimide. Other phthalimide-protected amine compounds can be conveniently synthe-sized from appropriate alkyl, aralkyl or aryl halides and phthalimide. Representative compounds include N-(7-bromoheptyl)phthalimide; N-(8-bromooctyl)phthalimide; N-(9-bromononyl)phthalimide; N-(10-bromododecyl)phthalimide; N-(11-bromoundecyl) phthalimide; N-(12-bromodocecyl)phthalimide; N-(13-bromotridecyl)phthalimide; N-(14-bromotetradecyl) phthalimide; N-(15-bromopentadecyl)phthalimide; N-(16-bromo-hexadecyl)phthalimide; N-(17-bromoheptadecyl) phthalimide; N-(18-bromooctadecyl)phthalimide; N-(19-bromononadecyl)phthalimide; N-(3-bromo-2-methylpropyl)phthalimide; N-(4-bromo-2-methyl-3-ethylbutyl)phthalimide; N-(3-bromo-2,2-diethyl-propyl) phthalimide; N-(4-bromo-3-propylbutyl)phthalimide; N-(10-bromo-2,8-dibutyldecyl)phthalimide; N-(8-bromo-6,6-dimethyloctyl)phthalimide; N-(8-bromo-6-propyl-6-butyloctyl) phthalimide; N-(4-bromo-2-methylbutyl) phthalimide; N-(5-bromo-2-methylpentyl)phthalimide; N-(5-bromo-3-methylpentyl) phthalimide; N-(6-bromo-2-ethylhexyl)phthalimide; N-(5-bromo-3-penten-2-one) phthalimide; N-(4-bromo-3-methyl-2-butanol) phthalimide; N-(8-bromo-3-amino-4-chloro-2-cyanooctyl) phthalimide; N-(7-bromo-3-methoxy-4-heptanal)phthalimide; N-(4-bromo-2-iodo-3-nitrobutyl)phthalimide; N-(12-bromo-4-isopropoxydodecyl)phthalimide; N-(10-bromo-4-azido-2-nitrodecyl)phthalimide;N-(9-bromo-5-mercaptononyl) phthalimide; N-(5-bromo-4-aminopentenyl)phthalimide; N-(5-bromo-penten-2-yl)phthalimide;N-(3-bromoallyl) phthalimide; N-(4-bromocrotyl)phthalimide;N-(3-bromopropargyl)phthalimide; N-(1-bromonaphth-4-yl) phthalimide; N-(2-bromoanthran-7-yl)phthalimide; and N-(2-bromophenanthr-6-yl)phthalimide. Such halide compounds are then reacted with an appropriate 2, 6 or 8-oxygen, 2, 6 or 8-sulfur or 2, 6 or 8 amine substituted purine or purine containing nucleoside.

Appended to these linkers, tethers, or space-spanning groups, are reactive or non-reactive functionalities. In a first embodiment of the invention, reactive functionalities are capable of catalyzing, alkylating, or otherwise effecting the cleavage of RNA, especially its phosphodiester bonds. In a further embodiment of the invention, the reactive functionalities are capable of cross-linking to a further RNA or DNA nucleic acid strand or to a further oligonucleotide including oligonucleotides of the invention. The reactive functionalities may either be basic, acidic, or amphoteric. Heteroatomic species can be formulated to be either basic or acidic or, indeed, to be amphoteric for such purposes. Alkylating and free radical forming functionalities may also be used.

Non-reactive functionalities, such as groups that enhance pharmacodynamic properties, include groups that improve oligonucleotide uptake, enhance oligonucleotide resistance to degradation, and/or strengthen sequence-specific hybridization with RNA. Non-reactive functionalities may also enhance pharmacokinetic properties. In the context of this invention, such groups improve oligonucleotide uptake, distribution, metabolism or excretion.

Reactive functionalities suitable for use as Q in the practice of this invention include, but are not limited to, halogens; substituted or unsubstituted heterocyclic compounds, such as substituted or unsubstituted heterocycloalkyls; amino containing groups, such as heterocycloalkylamines, polyalkylamines, imidazoles, imadiazole amides, alkylimidazoles; substituted or unsubstituted aldehydes; substituted or unsubstituted ketones; substituted or unsubstituted ethers; substituted or unsubstituted esters; substituted or unsubstituted aryl compounds having from about 6 to about 20 carbon atoms, such as aralkylamino having from about 6 to about 20 carbon atoms, aminoaralkylamino having from about 6 to about 20 carbon atoms, alkyloxyaryl compounds, or allyloxyaryl compounds.

In addition to amines (—$NH_2$), further preferred reactive moieties suitable for the functional groups of the invention include hydrazines (—NH—NH—), hydroxylamines (—NH—OH), semicarbazides (—NH—C(O)—NH—$NH_2$), thiosemicarbazides (—NH—C(S)—NH—$NH_2$), hydrazones (—N=NH), hydrazides (—C(O)—NH—$NH_2$), alcohols (—OH), thiols (—SH), and aldehydes (—CH=O). Amines of this invention are also meant to include polyalkylamino compounds and aminoalkylamines such as aminopropylamines and further heterocycloalkylamines, such as imidazol-1, 2, or 4-yl-propylamine.

Suitable heterocyclic groups include, but are not limited to, imidazole, tetrazole, triazole, pyrrolidine, piperidine, piperazine and morpholine. Amines include amines of all of the above alkyl, alkenyl and aryl groups including primary and secondary amines and "masked amines" such as phthalimide. Other reactive functionalities suitable for practicing the invention include, without limitation, compounds having thiol (SH), carbonyl (aldehyde HC=O or ketone C=O), or alcohol (OH) functionalities.

Non-reactive functionalities for Q, include, but are not limited to, alkyl chains, polyamines, ethylene glycols, polyamides, aminoalkyl chains, amphipathic moieties, points for reporter group attachment, and intercalators attached to any of the preferred sites for attachment, as described above.

The invention further provides the above compounds comprising a sugar and base moiety as discussed above. In certain preferred embodiments, Z is ribose or deoxyribose. In a more preferred embodiment, Z is deoxyribose. In another preferred embodiment, Z is a sugar analog, preferably the deoxyribose type.

Preferably the sugar is the deoxyribose type, but ribose and sugar analogs are fully contemplated within the scope of this invention. Sugar analogs with substituents at the 3' or 5' of deoxyribose, or at the 2', 3', or 5' of ribose are contemplated. Suitable substituents on the sugar moiety include, but are not limited to, O, H, lower alkyl, substituted lower alkyl, aralkyl, heteroaralkyl, heterocycloalkyl, aminoalkylamino, heterocycloalkyl, polyalkylamino, substituted silyl, F, Cl, Br, CN, $CF_3$, $OCF_3$, OCN, O-alkyl, S-alkyl, SOMe, $SO_2Me$, $ONO_2$, $NO_2$, $N_3$, $NH_2$, NH-alkyl, $OCH_2CH=CH_2$, $OCH=CH_2$, $OCH_2CCH$, OCCH, OCCHO, or an RNA cleaving moiety. As will be appreciated by persons of ordinary skill in the art, variations in the structures of the sugar moieties useful in the preparation of the subject compositions may be made without deviating from the spirit of the invention.

Generally, sugar moieties may be attached to the novel purine based compounds of the invention using methods known in the art. See Revankar, supra.

Substituted sugars may be synthesized according to the methods disclosed in PCT Patent Application Number PCT\US91\00243 assigned to a common assignee hereof, entitled "Compositions and Methods for Detecting and Modulating RNA Activity and Gene Expression," the disclosures of which are incorporated herein by reference to disclose more fully such modifications. See also Motawai, supra.

For example, a substituted sugar as, methyl 3-O-(t-butyldiphenylsilyl)-2,5-dideoxy-5-C-formyl-α/β-D-erythro-pentofuranoside, can be prepared by modifying 2-deoxy-D-ribose to methyl 2-deoxy-α/β-D-erythro-pentofuranoside (prepared according to the method of M. S. Motawai and E. B. Pedersen, *Liebigs Ann. Chem.* 1990, 599–602), which on selective tosylation followed by 3-O-silylation gave methyl 3-O-(t-butyldimethylsilyl)-2-deoxy-5-O-tosyl-α/β-D-erythro-pentofuranoside.

There is no specific number of sugar moieties which must be in modified form in an oligonucleotide of the invention to achieve the benefits of the invention. Any number, from zero to all sugar moieties present in the oligonucleotide may be so modified, provided that the targeting portion of the oligonucleotide exhibits an ability to penetrate into the intracellular spaces of cells of the organism in question or to otherwise contact the target and specifically bind therewith to form a hybrid capable of detection and/or modulation of the RNA activity.

In some preferred embodiments, X will be a nitrogen protecting group. Generally, protecting groups are known per se as chemical functional groups that can be selectively appended to and removed from functionalities, such as amine groups. These groups are present in a chemical compound to render such functionality inert to chemical reaction conditions to which the compound is exposed. See, e.g., Greene and Wuts, *Protective Groups in organic Synthesis,* 2d edition, John Wiley & Sons, New York, 1991. Numerous amine protecting groups are known in the art, including, but not limited to, the allyloxycarbonyl (Alloc), benzyloxycarbonyl (CBz), chlorobenzyloxycarbonyl, t-butyloxycarbonyl (Boc), fluorenylmethoxycarbonyl (Fmoc), isonicotinyloxycarbonyl (i-Noc) groups. (see, e.g., Veber and Hirschmann, et al., *J. Org. Chem.* 1977, 42, 3286 and Atherton, et al., The Peptides, Gross and Meienhofer, Eds, Academic Press; New York, 1983; Vol. 9 pp. 1–38). For example, it is known that the Boc group can protect an amine group from base and from reducing conditions but that it can be removed with acid. Other nitrogen protecting groups will be apparent to those skilled in the art and may be used without detracting from the spirit of the invention. Any ester protecting groups known to those skilled in the art may be used; tetrahydropyranyl is an example of such a group. See Theodora Green and P. Woods, *Protective Groups in Organic Synthesis,* 2d Ed., supra.

The invention further provides compositions comprising a sugar and base moiety as discussed above, with the 3' position of the sugar moiety derivatized with an activated phosphate group. Generally, nucleotides of the invention may be prepared by protecting the 5' position of the sugar moiety and derivatizing the 3' position with an appropriate phosphoramidite or other activated phosphate suitable for use on a DNA synthesizer.

In another aspect of the invention, oligonucleo-tides or oligonucleotide analogs incorporating the novel compounds of the invention are provided. Generally, the oligonucleotides or oligonucleotide analogs may comprise a sugar modified or native oligonucleotide containing a target sequence that is specifically hybridizable with a preselected nucleotide sequence, a sequence of DNA or RNA that is involved in the production of proteins whose synthesis is ultimately to be modulated or inhibited entirely, and is a single stranded or double stranded DNA or RNA molecule which is nuclease resistant.

In a preferred embodiment, the oligonucleotide comprises a first oligonucleotide region and a second nucleotide region; together said first and said second region of a nucleotide sequence essentially complementary to at least a portion of said RNA; said first region including at least one nucleotide in accordance with the compounds of the invention as discussed above; and said second region including a plurality of consecutive phosphorothioate linked nucleotides having a 2'-deoxy-erythro-pentofuranosyl sugar moiety.

In another preferred embodiment, an oligonucleotide comprises a third region of said oligonucleotide, said third region including at least one nucleotide in accordance with the compounds of the invention as discussed above; and wherein said second region is positioned in said oligonucleotide between said first and third regions.

Oligonucleotides or oligonucleotide analogs incorporating the novel compounds of the invention may be synthesized conveniently, through solid state synthesis of known methodology, to be complementary to or at least to be specifically hybridizable with the preselected nucleotide sequence of the RNA or DNA. Nucleic acid synthesizers are commercially available and their use is generally understood by persons of ordinary skill in the art as being effective in generating nearly any oligonucleotide of reasonable length which may be desired. An oligonucleotide or oligonucleotide analog may then be constructed on a synthesizer incorporating one or more of the purine compounds of the invention in its sequence.

The resulting novel oligonucleotides or oligonucleotide analogs are synthesized by a standard solid phase, automated nucleic acid synthesizer such as the Applied Biosystems Incorporated 380B or MilliGen/Biosearch 7500 or 8800. Triester, phosphoramidite, or hydrogen phosphonate coupling chemistries described in, for example, M. Caruthers, *Oligonucleotides: Antisense Inhibitors of Gene Expression.,* pp. 7–24, J. S. Cohen, ed. (CRC Press, Inc. Boca Raton, Fla., 1989), are employed by these synthesizers to provide the desired oligonucleotides or oligonucleotide analogs. The Beaucage reagent, as described in, for example, *Journal of American Chemical Society,* Vol. 112, pp. 1253–1255 (1990), or elemental sulfur, as described in Beaucage et al., *Tetrahedron Letters,* Vol. 22, pp. 1859–1862 (1981), is used with phosphoramidite or hydrogen phosphonate chemistries to provide substituted phosphorothioate oligonucleotides.

These antisense agents comprise a targeting portion specifically hybridizable with a preselected nucleotide sequence of RNA. Some of the phosphodiester bonds may be substituted with a structure that functions to enhance the compositions' ability to penetrate into the intracellular region of a cell where the RNA, the activity of which is to be modulated, is located. Such substitutions can include substitution or modification about the phosphorus atoms of the oligonucleotides. Variations in the phosphate backbone useful in the preparation of the subject compositions may be made without deviating from the spirit of the invention.

Modifications to the phosphate portion of the oligonucleotide backbone, which are thought in some cases to enhance properties of sugar modified oligonucleotides, are within the scope of the invention. Such substitutions include, but are not limited to, phosphorothioate, phosphorodithioate, methyl phosphonate, alkyl phosphate, phosphoramidites, phosphotriester and other like modifications. Other modifications also included within the scope of this inventions are disclosed as set forth in U.S. Patent Applications assigned to a common assignee hereof, entitled "Backbone Modified Oligonucleotide Analogs," Ser. No. 703,619 and "Heteroatomic Oligonucleotide Linkages," Ser. No. 903,160, the disclosures of which are incorporated herein by reference in order to disclose more fully such modifications.

In addition to substitutions at the 2, 6, and 8 positions of the purine core, other positions for attachment of reactive and non-reactive functionalities having a similar effect may be found, especially when further modifications of the purine structure is undertaken as may be done by persons of ordinary skill in the art, without deviating from the spirit of the present invention.

Also in accordance with this invention, there are provided sequence-specific, covalently cross-linked nucleic acids comprising:

a first oligonucleotide sequence region and a second oligonucleotide sequence region, wherein said first region includes at least one purine nucleotide of the formula:

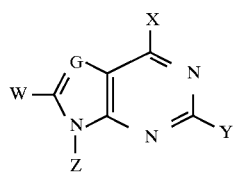

wherein G is $CR_5$ or N;
$R_5$ is H or a hydrocarbyl group having from 1 to 6 carbon atoms;
X is halogen, $NH_2$, OH, $NHR_6Q_1$, $OR_6Q_1$, NHJ, OJ or SJ wherein said $R_6$ is H or a hydrocarbyl group having from 2 to about 20 carbon atoms, $Q_1$ comprises at least one reactive or non-reactive functionality and J comprises a space spanning group $R_7$ and an active functional group $Q_4$;
Y is halogen, $NH_2$, H, SH, OH, NHJ, OJ or SJ where J comprises a space spanning group $R_7$ and an active functional group $Q_4$;
W is H, NHK, OK or SK where K comprises a space spanning group $R_7$ and an active non-psoralen functional group $Q_5$;
Z is H, a nitrogen protecting group, or a sugar moiety; and providing that at least one of said X or Y groups is NHJ, OJ or SJ, or at least one of said W groups is NHK, OK or SK;
said second sequence region including a second nucleotide capable of covalently bonding with said J group or said K group of said first nucleotide; and
a covalent cross-linkage between said first and said second nucleotides.

In preferred embodiments of the invention, J is a tether, linker or space-spanning group $R_7$ coupled to the reactive functional group $Q_4$, and K is a tether, linker or space-spanning group $R_7$ coupled to the reactive functional group $Q_5$. The groups $Q_4$ or $Q_5$ are functional groups that are capable of forming a covalent bond with a further functionality. Preferably, $R_7$ is a hydrocarbyl group having from 1 to about 20 carbon atoms.

In certain preferred embodiments, both the first and the second nucleotides are one of said purine nucleotides of the proceeding structure each including a group J or a group K and said covalent cross-linkage is between these groups J or groups K.

In preferred embodiments, the space-spanning group $R_7$ is from about 8 to about 13 atoms in length and the functional group $Q_n$ is a thiol, an aldehyde, a protected aldehyde, an aldehyde precursor, an amine, hydrazine, hydroxylamine, semicarbazide, thiosemicarbazide, hydrazide, alcohol, or alkoxy. In certain embodiments of the invention, the first sequence region and second sequence regions are on a single oligonucleotide strand. In further embodiments the first and second sequence regions are on different strands. It is preferred that the first sequence region and said second sequence region be complementary to and specifically hybridizable with one another.

In other more preferred embodiments, the group J is at the position X, and the space-spanning group $R_7$ is from about 8 to about 13 atoms in length and said group $Q_4$ is a thiol, an aldehyde, a protected aldehyde, an aldehyde precursor, $NH_2$, polyalkylamine, aminoalkylamine, hydrazine (—NH—NH—), hydroxylamine (—NH—OH), semicarbazide (—NH—C(O)—NH—$NH_2$), thiosemicarbazide (—NH—C(S)—NH—$NH_2$), hydrazone (—N═NH), hydrazide (—C(O)—NH—$NH_2$), alcohol, or alkoxy. In one embodiment the first sequence region and second sequence regions are on a single oligonucleotide strand. In a further embodiment the first and second sequence regions are on different strands. It is preferred that the first sequence region and said second sequence region be complementary to and specifically hybridizable with one another.

In other preferred embodiments, the group J is at the position Y; the space-spanning group $R_7$ is from about 8 to about 13 atoms in length and said group $Q_4$ is a thiol, an aldehyde, a protected aldehyde, an aldehyde precursor, an amine, hydrazine, hydroxylamine, semicarbazide, thiosemicarbazide, hydrazide, alcohol, or alkoxy. In one embodiment the first sequence region and second sequence regions are on a single oligonucleotide strand. In a further embodiment the first and second sequence regions are on different strands. It is preferred that the first sequence region and said second sequence region be complementary to and specifically hybridizable with one another.

In still other certain preferred embodiments, the group K is at the position W and the space-spanning group $R_7$ is from about 8 to about 13 atoms in length and said group $Q_5$ is a thiol, an aldehyde, a protected aldehyde, an aldehyde precursor, an amine, hydrazine, hydroxylamine, semicarbazide, thiosemicarbazide, hydrazide, alcohol, or alkoxy. In one embodiment the first sequence region and second sequence regions are on a single oligonucleotide strand. In a further embodiment the first and second sequence regions are on different strands. It is preferred that the first sequence region and said second sequence region be complementary to and specifically hybridizable with one another.

In certain other more preferred embodiments, wherein the first nucleotide is located in a first nucleotide sequence and the second nucleotide is located in a second nucleotide sequence, and the second nucleotide sequence is complementary to and hybridizable with the first nucleotide sequence, and the first and second nucleotide sequences are located on a single strand of said oligonucleotide, the second nucleotide sequence is located on the oligonucleotide at a distance separated from the first nucleotide sequence sufficient to allow the oligonucleotide to assume a conformation wherein said first and second nucleotide sequences are mutually aligned with and specifically hybridized with one another.

In another preferred embodiment, the first nucleotide is located in a first nucleotide sequence and the second nucleotide is located in a second nucleotide sequence, and the first and second nucleotide sequences are located on a single strand of an oligonucleotide with the second nucleotide sequence located on the oligonucleotide at a non-hybridizable position with respect to the first nucleotide sequence and at a distance from the first nucleotide sequence sufficient to allow the oligonucleotide to assume a conformation such that the first and second nucleotide sequences are located in spatial proximity with each other.

In certain other preferred embodiments the first nucleotide is located in a first nucleotide sequence and the second nucleotide is located in a second nucleotide sequence, the second nucleotide sequence is complementary to and specifically hybridizable with the first nucleotide sequence and the first and second nucleotide sequences are located on different oligonucleotide strands.

In certain preferred embodiments, the group J or K on the first nucleotide includes a first space-spanning group having a first active functional group, the group J or K on the second nucleotide includes a second space-spanning group having a second active functional group and the covalent cross-linkage is between the first and second active functional groups.

In certain preferred embodiments, the first and second space-spanning groups $R_7$ are in accordance with $R_n$, as discussed above. The first and second space-spanning groups $R_7$ may be independently any of the $R_n$ groups as discussed above; it is not required that the first and second region have the same space-spanning groups nor is it required that the space-spanning groups be different.

Space-spanning groups $R_7$ according to the invention comprise hydrocarbyl groups having from about 2 to about 20 carbon atoms, preferably from about 8 to about 13 carbon atoms. The length of the space-spanning group on each strand or region of a single strand can be between 1 to about 20 carbon atoms. Therefore, when two space-spanning groups are linked together, the total number of carbon atoms should be less than about 40 atoms in length. It is preferred that the space-spanning group on an individual strand or on a sequence region of a single strand be about 20 atoms or less in length. More preferably, the cross-linking group is from 8 to 13 atoms in length.

As discussed above, the space-spanning group may be a linear or straight chain hydrocarbyl group. In one embodiment of the invention, the space-spanning group comprises a methylene chain from 2 to about 20 carbon atoms in length. Where the connecting atoms are methylene groups, the connecting group and the space-spanning group together form an alkyl chain. In other embodiments, one or more unsaturated sites are located in the space-spanning group, resulting in alkenyl or alkynyl chains. In these embodiments the alkenyl or alkynyl space-spanning groups have from 2 to about 20 carbon atoms.

In other embodiments the space-spanning group further includes branched chains and substituent groups that extend from a backbone or primary straight chain. Branched chains can be selected from branched alkyl, branched alkenyl or branched alkyne space-spanning groups. The branched chains, in addition to the carbon atoms of the main chain, have from 2 to about 20 carbon atoms. Further substituent atoms or substituent groups can also extend from the backbone or from any branched chains. Additionally, any of the hydrocarbyl groups discussed above (i.e., straight, branched, or cyclic alkyl, alkenyl, or alkynyl groups) may be internally interrupted with heteroatoms, such as O, N, or S; however, this is not required. For example, polyoxy-hydrocarbyl or polyamino-hydrocarbyl compounds are fully contemplated within the ambit of the invention. Some further examples include embodiments where hydrocarbyl groups may comprise a polyhydric alcohol, such as —$CH_2$—$(CHOH)_n$—$CH_2OH$, wherein n=1 to 5. Alternatively, by way of example, hydrocarbyl groups may comprise an ether, such as —$CH_2(CHOH)nCH_2$. $O(CH_2)_m$, where n=1 to 10 and m=1 to 10.

Thus, the space-spanning group can include $C_1$–$C_{20}$ straight chain alkyl, $C_1$–$C_{20}$ straight chain substituted alkyl, $C_2$–$C_{20}$ branched chain alkyl, $C_2$–$C_{20}$ branched chain substituted alkyl, $C_2$–$C_{20}$ straight chain alkenyl, $C_2$–$C_{20}$ straight chain substituted alkenyl, $C_3$–$C_{20}$ branched chain alkenyl, $C_3$–$C_{20}$ branched chain substituted alkenyl, $C_2$–$C_{20}$ straight chain alkyne, $C_2$–$C_{20}$ straight chain substituted alkyne, $C_3$–$C_{20}$ branched chain alkyne and $C_3$–$C_{20}$ branched chain substituted alkyne groups. Other space-spanning groups include aryl, aralkyl and heterocyclic groups.

Alkyl, alkenyl, and alkynyl groups of the invention are as discussed above in connection with the hydrocarbyl groups of the invention. Substituent groups for the above include, but are not limited to, other alkyl, haloalkyl, alkenyl, alkoxy, thioalkoxy, haloalkoxy and aryl groups as well as amino, azido, carboxy, cyano, halogen, heterocycles, hydroxyl, keto, mercapto, nitrates, nitrites, nitro, nitroso, nitrile, sulfides, sulfones, sulfoxides, trifluoromethyl, O-alkyl, S-alkyl, NH-alkyl, silyl, intercalators, conjugates, polyamines, polyamides, polyethylene glycols, polyethers, groups that enhance the pharmacodynamic properties of oligonucleotides and groups that enhance the pharmacokinetic properties of oligonucleotides. Typical intercalators and conjugates include cholesterols, phospholipids, biotin, phenanthroline, phenazine, phenanthridine, anthraquinone, acridine, fluoresceins, rhodamines, coumarins, and dyes. Halogens include fluorine, chlorine, bromine and iodine. Other suitable substituent groups will be apparent to those skilled in the art and may be used without departing from the spirit of the invention.

The active functional groups on the space-spanning moieties can be reacted with both heterobifunctional and homobifunctional groups. As will be recognized, formaldehyde is a homobifunctional group when it is reacted with two amines. Reaction of formaldehyde with amine functional groups that are attached to each of two strands (or regions of a single strand) yields an aminoalkylamine (—NH—$CH_2$—NH—) linkage.

Reaction of a hydrazine (—NH—NH—) with an aldehyde yields a hydrazone (—HC=N—NH—) cross-linkage, while reaction of a hydroxylamine (HO—N—) with an aldehyde yields an oxime (—O—N=CH—) cross-linkage. Reaction of an aldehyde with a hydrazide (—C(O)—NH—$NH_2$) yields a hydrazide-hydrazone (—C(O)—NH—N=CH—) cross-linkage, reaction of an aldehyde with a semicarbazide (—NH—C(O)—NH—$NH_2$) yields a semicarbazone (—NH—C(O)—NH—N=C—) cross-linkage, and reaction of an aldehyde with a thiosemicarbazide (—NH—C(S)—NH—NH$_2$) yields a thiosemi-carbazone (—NH—C(S)—NH—N=C—) cross-linkage. The hydrazone, oxime, hydrazidehydrazone, semicarbazone and thiosemi-carbazone linkages can be reduced to corresponding hydrazine, hydroxylamine, hydrazide-hydrazine, semicarbazide and thio-semicarbazide, respectively, if desired. Hydrazine can also be used as a bifunctional group to join strands that each have a space-spanning group terminated with an aldehyde. The hydrazine adds to a first aldehyde group to form an aldehyde-hydrazone that, in turn, reacts with the second aldehyde to yield an azine (—CH=N—N=CH—) cross-linkage.

Heterobifunctional groups allow the use of one active functionality on one strand (or a region of a single strand) and the use of a different active functionality on another strand (or another region of a single strand). Thus, one strand could have an amine functionality on an end of its space-spanning group and another strand could have a thiol functionality on the end of its space-spanning group.

Space-spanning groups on one of the strands (or region of a single strand) may not be necessary where heterobifunctional groups or certain of the above-noted active functionalities are employed.

A variety of heterobifunctional coupling reagents are available from commercial sources including Pierce (Rockford, Ill.). These reagents include 1-ethyl-3-(3-dimethylaminopropyl)carbodiimide (a water soluble DCC type coupling reagent), bifunctional imidoesters such as dimethyl adipimidate dihydrochloride, dimethyl pimelimidate dihydrochloride, and dimethyl 3,3'-dithiobispropionimidate dihydrochloride (for coupling amine groups), and 2-iminothiolane (for coupling amines thiols). Coupling reagents also include compounds having N-hydroxysuccinimide moieties that react with amines, compounds having internal disulfide bonds that can be released to expose an active thiol moiety that can be further coupled via a disulfide bond with a further thiol functionality, and compounds having sulfosuccinimidyl groups (e.g., N-hydroxysulfosuccinimide) that have different reactivity toward amines than N-hydroxysuccinimides. Coupling reagents further include pyridyl-disulfides that exchange with free thiol moieties, active halogen species such as β-carbonyl alkylhalides, e.g. iodo acetamide, maleimide moieties and photoreactive aryl azides such as phenyl azide. Also, thioisocyanates can be used to couple with active functionalities on space-spanning groups.

The various functional groups of the bifunctional cross-linkers are joined together with suitable linking atoms. Representative, commercially available bifunctional compounds include sulfosuccinimidyl 4-(N-maleimidoethyl) cyclohexane-1-carboxylate, N-succinimidyl 3-(2-pyridyldithio)propionate, N-sulfosuccinimidyl(4-iodoacetyl)amino-benzoate, sulfo-succinimidyl 4-(p-maleimidophenyl)butyrate, m-maleimido-benzoyl-N-hydroxysulfosuccinimide ester, succinimidyl 4-(N-maleimidomethyl)cyclohexane-1-carboxylate, bismaleimidohexane, disulfosuccinimidyl tartrate, ethylene glycolbis(succinimidylsuccinate), dithiobis(succinimidyl-propionate), disuccinimidyl suberate, N-hydroxysuccinimidyl-4-azidosalicylic acid, N-5-azido-2-nitrobenzoyloxysuccinimide and sulfonsuccinimidyl 2-(m-azido-o-nitrobenzamido)-ethyl-1,3'-dithiopropionate. Each of these bifunctional groups are reacted with an appropriate active functionality on the space-spanning group. Thus, oligonucleotide strands (or regions of a single strand) bearing the space-spanning groups are cross-linked through the bifunctional group.

The present invention is further described in the following examples. These examples are for illustrative purposes only, and are not to be construed as limiting the appended claims.

EXAMPLE 1

2,6-Dichloro-9-(2-deoxy-3,5-di-O-p-toluoyl-β-D-erythro-pentofuranosyl)purine. (1)

To a stirred solution of 2,6-dichloropurine (25.0 g, 132.27 mmol) in dry acetonitrile (1000 mL) was added sodium hydride (60% in oil, 5.40 g, 135 mmol) in small portions over a period of 30 minutes under an atmosphere of argon. After the addition of NaH, the reaction mixture was allowed to stir at room temperature for 30 minutes. Predried and powdered 1-chloro-2-deoxy-3,5-di-O-p-toluoyl-β-D-erythro-pentofuranose (53.0 g, 136 mmol) was added during a 15 minute period and the stirring continued for 10 hours at room temperature under argon atmosphere. The reaction mixture was evaporated to dryness and the residue dissolved in a mixture of $CH_2Cl_2/H_2O$ (250:100 mL) and extracted in dichloromethane (2×250 mL). The organic extract was washed with brine (100 mL), dried, and evaporated to dryness. The residue was dissolved in dichloromethane (300 mL), mixed with silica gel (60–100 mesh, 250 g) and evaporated to dryness. The dry silica gel was placed on top of a silica gel column (250–400 mesh, 12×60 cm) packed in hexane. The column was eluted with hexanes (1000 mL), toluene (2000 mL), and toluene:ethyl acetate (9:1, 3000 mL). The fractions having the required product were pooled together and evaporated to give 52 g (72%) of 1 as a white solid. A small amount of solid was crystallized from ethanol for analytical purposes. mp 160°–162° C.; $^1$H NMR (DMSO-$d_6$); δ2.36 (s, 3H, $CH_3$), 2.38 (s, 3H, $CH_3$), 2.85 (m, 1H, $C_2$'H), 3.25 (m, 1H, $C_2$'H), 4.52 (m, 1H, $C_4$H), 4.62 (m, 2H, $C_5$'$CH_2$), 5.80 (m, 1H, $C_3$'H), 6.55 (t, 1H, $J_{1',2'}$=6.20 Hz, $C_1$'H), 7.22 (dd, 2H, ArH), 7.35 (dd, 2H, ArH), 7.72 (dd, 2H, ArH), 7.92 (dd, 2H, ArH), and 8.92 (s, 1H, $C_8$H).

EXAMPLE 2

2-Chloro-6-allyloxy-9-(2-deoxy-β-D-erythro-pentofuranosyl) purine. (2)

To a stirred suspension of 1, (10.3 g, 19.04 mmol) in allyl alcohol (150 mL) was added sodium hydride (60%, 0.8 g, 20.00 mmol) in small portions over a 10 minute period at room temperature. After the addition of NaH, the reaction mixture was placed in a preheated oil bath at 55° C. The reaction mixture was stirred at 55° C. for 20 minutes with the exclusion of moisture. The reaction mixture was cooled, filtered, and washed with allyl alcohol (50 mL). To the filtrate IRC-50 (weakly acidic) H$^+$ resin was added until the pH of the solution reached 4–5. The resin was filtered, washed with methanol (100 mL), and the filtrate was evaporated to dryness. The residue was absorbed on silica gel (10 g, 60–100 mesh) and evaporated to dryness. The dried silica gel was placed on top of a silica column (5×25 cm, 100–250 mesh) packed in dichloromethane. The column was then eluted with $CH_2Cl_2$/acetone (1:1). The fractions having the product were pooled together and evaporated to dryness to give 6 g (96%) of 2 as foam. $^1$H NMR ($Me_2$SO-$d_6$) δ2.34 (m, 1H, $C_2$'H), 2.68 (m, 1H, $C_{2'H}$), 3.52 (m, 2H, $C_5$'H), 3.86 (m, 1H, $C_4$'H), 4.40 (m, 1H, $C_3$'H), 4.95 (t, 1H, $C_5$'OH), 5.08 (d, 2H, $CH_2$), 5.35 (m, 3H, $CH_2$ and $C_3$'OH), 6.10 (m, 1H, CH), 6.35 (t, 1H, $J_{1',2'}$=6.20 Hz, $C_1$'H), 8.64 (s, 1H, $C_8$H). Anal. Calcd for $C_{13}H_{15}ClN_4O_4$: C, 47.78; H, 4.63; N, 17.15; Cl, 10.86. Found: C, 47.58; H, 4.53; N, 17.21; Cl, 10.91.

EXAMPLE 3

2-Chloro-9-(2-deoxy-β-D-erythro-pentofuranosyl) inosine. (3)

A mixture of 2 (6 g, 18.4 mmol), Pd/C (10%, 1 g) and triethylamine (1.92 g, 19.00 mmol) in ethyl alcohol (200 mL) was hydrogenated at atmospheric pressure during 30 minute periods at room temperature. The reaction mixture was followed by the absorption of volume of hydrogen. The reaction mixture was filtered, washed with methanol (50 mL), and the filtrate evaporated to dryness. The product 5.26 g (100%) was found to be moisture sensitive and remained as a viscous oil. The oil was used as such for further reaction without purification. A small portion of the oil was dissolved in water and lyophilized to give an amorphous solid 3: $^1$H NMR (Me$_2$SO-d$_6$) δ2.35 (m, 1H, C$_{2'}$H), 2.52 (m, 1H, C$_{2'}$H), 3.54 (m, 2H, C$_{5'}$H), 3.82 (m, 1H, C$_{4'}$H), 4.35 (m, 1H, C$_{3'}$H), 4.92 (b s, 1H, C$_{5'}$OH), 5.35 (s, 1H, C$_{3'}$OH), 6.23 (t, 1H, J$_{1',2'}$=6.20 Hz, C$_1$H), 8.32 (s, 1H, C$_8$H), 13.36 (b s, 1H, NH).

EXAMPLE 4

N$_2$-[Imidazol-1-yl(propyl)]-9-(2-deoxy-β-D-erythro-pentofuranosyl)guanosine. (4)

A solution of the nucleoside of 3 (10.3 g, 36.00 mmol) and 1-(3-aminopropyl)imidazole (9.0 g, 72.00 mmol) in 2-methoxyethanol (60 mL) was heated in a steel bomb at 100° C. (oil bath) for 24 hours. The bomb was cooled to 0° C., opened carefully and the precipitated solid was filtered. The solid was washed with methanol (50 mL), acetone (50 mL), and dried over sodium hydroxide to give 9 g (67%) of pure 4. A small amount was recrystallized from DMF for analytical purposes: mp 245°–47° C.: $^1$H NMR (Me$_2$SO-d$_6$) δ1.94 (m, 2H, CH$_2$), 2.20 (m, 1H, C$_{2'}$H), 2.54 (m, 1H, C$_{2'}$H), 3.22 (m, 2H, CH$_2$), 3.51 (m, 2H, C$_{5'}$H), 3.80 (m, 1H, C$_{4'}$H), 3.98 (m, 2H, CH$_2$), 4.34 (m, 1H, C$_{3'}$H), 4.90 (b s, 1H, C$_{5'}$OH), 5.51 (s, 1H, C$_{3'}$OH), 6.12 (t, 1H, J$_{1',2'}$=6.20 Hz, C$_1$H), 6.46 (b s, 1H, NH), 6.91 (s, 1H, ImH)), 7.18 (s, 1H, ImH), 7.66 (s, 1H, ImH), 7.91 (s, 1H, C$_8$H), 10.60 (b s, 1H, NH). Anal. Calcd for C$_{16}$H$_{21}$N$_7$O$_4$: C, 51.19; H, 5.64; N, 26.12. Found: C, 50.93; H, 5.47; N, 26.13.

EXAMPLE 5

3',5'-Di-O-isobutyryl-N$_2$-[imidazol-1-yl(propyl)]-N$_2$-isobutyryl-9-(2-deoxy-β-D-erythro-pentofuranosyl)guanosine. (5)

To a well dried solution of the substrate of the substrate 4(1.5 g, 4.00 mmol) and triethylamine (1.62 g, 16.00-mmol) in dry pyridine (30 mL) and dry DMF (30 mL) was added isobutyryl chloride (1.69 g, 16.00 mmol) at room temperature. The reaction mixture was allowed to stir at room temperature for 12 hours and evaporated to dryness. The residue was partitioned between dichloromethane (100 mL) and water (50 mL) and extracted with CH$_2$Cl$_2$ (2×200 mL). The organic extract was washed with brine (100 mL) and dried over anhydrous MgSO$_4$. The dried organic extract was evaporated to dryness and the residue was purified by flash chromatography using CH$_2$Cl$_2$/MeOH as eluent. The pure fractions were pooled, evaporated to dryness which on crystallization from CH$_2$Cl$_2$/MeOH gave 1.8 g (77%) of 5 as a colorless crystalline solid: mp 210°–212° C.: $^1$H NMR (Me$_2$SO-d$_6$) δ1.04 (m, 18H, 3 Isobutyryl CH$_3$), 1.94 (m, 2H, CH$_2$), 2.56 (m, 4H, C$_{2'}$H and 3 Isobutyryl CH) 2.98 (m, 1H, C$_{2'}$H), 3.68 (m, 2H, CH$_2$), 3.98 (m, 2H, CH$_2$), 4.21 (2 m, 3H, C$_{5'}$H and C$_{4'}$H), 5.39 (m, 1H, C$_{3'}$H), 6.30 (t, 1H, J$_{1',2'}$=6.20 Hz, C$_1$H), 6.84 (s, 1H, ImH), 7.18 (s, 1H, ImH), 7.34 (s, 1H, ImH), 8.34 (s, 1H, C$_8$H), 10.60 (b s, 1H, NH). Anal. Calcd for C$_{28}$H$_{39}$N$_7$O$_7$: C, 57.42; H, 6.71; N, 16.74. Found: C, 57.29; H, 6.58; N, 16.56.

EXAMPLE 6

6-0-[2-(4-Nitrophenyl)ethyl]-N$_2$-3',5'-tri-O-isobutyryl-N$_2$-[imidazol-1-yl(propyl)]-9-(2-deoxy-β-D-erythro-pentofuranosyl)guanosine. (6)

To a stirred solution of 5 (2.0 g, 3.42 mmol), triphenylphosphine (2.68 g, 10.26 mmol) and p-nitrophenyl ethanol (1.72 g, 10.26 mmol) in dry dioxane was added diethylazodicarboxylate (1.78 g, 10.26 mmol) at room temperature. The reaction mixture was stirred at room temperature for 12 hours and evaporated to dryness. The residue was purified by flash chromatography over silica gel using CH$_2$Cl$_2$/acetone as the eluent. The pure fractions were pooled together and evaporated to dryness to give 2.4 g (96%) of the title compound as an amorphous solid: $^1$H NMR (Me$_2$SO-d$_6$) δ1.04 (m, 18H, 3 Isobutyryl CH$_3$), 1.94 (m, 2H, CH$_2$), 2.50 (m, 3H, C$_{2'}$H and 2 Isobutyryl CH), 3.00 (m, 1H, C$_{2'}$H), 3.12 (m, 1H, Isobutyryl CH), 3.24 (m, 2H, CH$_2$), 3.82 (m, 2H, CH$_2$), 3.98 (m, 2H, CH$_2$), 4.21 (2 m, 3H, C$_{5'}$CH$_2$ and C$_{4'}$H), 4.74 (m, 2H, CH$_2$), 5.39 (m, 1H, C$_{3'}$H), 6.34 (t, 1H, J$_{1',2'}$=6.20 Hz, C$_1$H), 6.82 (s, 1H, ImH), 7.08 (s, 1H, ImH), 7.56 (s, 1H, ImH), 7.62 (d, 2H, ArH), 8.1 (d, 2H, ArH), 8.52 (s, 1H, C$_8$H). Anal. Calcd for C$_{36}$H$_{46}$N$_8$O$_9$·½ H$_2$O: C, 58.13; H, 6.37; N, 15.01. Found: C, 58.33; H, 6.39; N, 14.75.

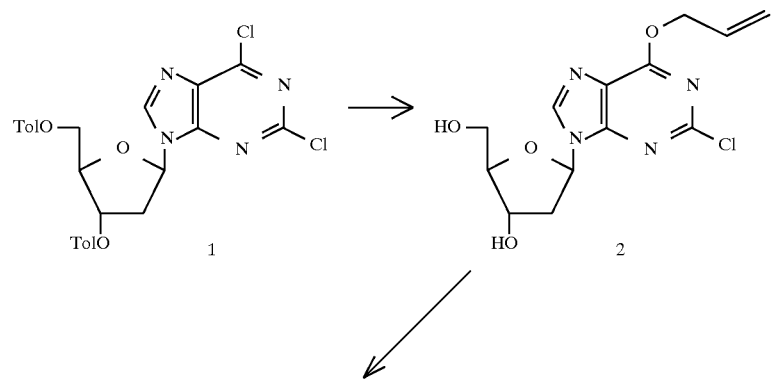

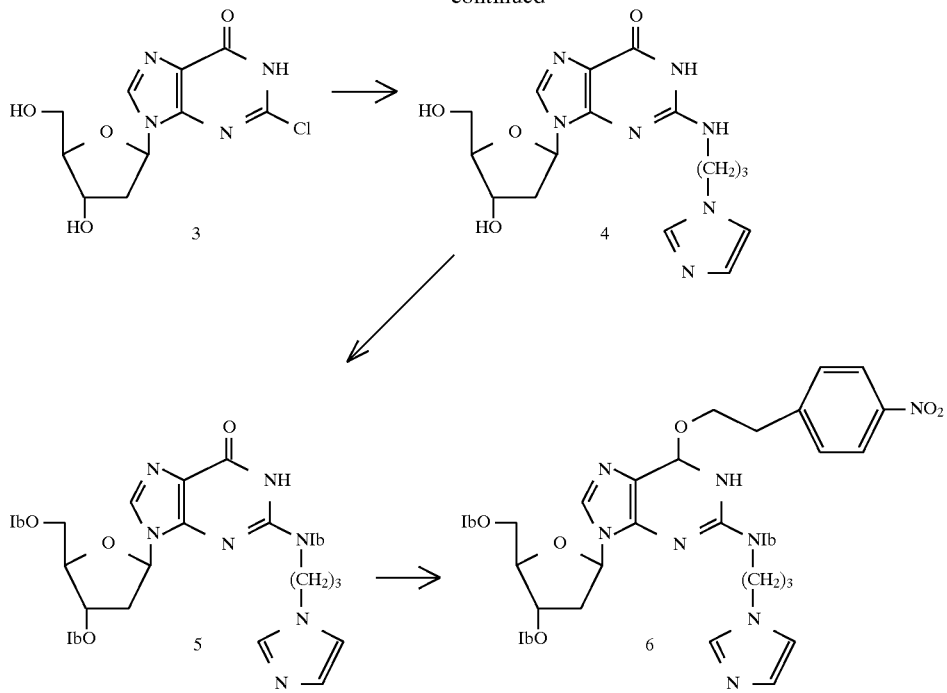

EXAMPLE 7

6-O-[2-(4-Nitrophenyl)-ethyl]-$N_2$-isobutyryl-$N_2$-[imidazol-1-yl(propyl)]-9-(2-deoxy-β-D-erythro-pentofuranosyl)guanosine. (7)

To a stirred solution of 6 (9.00 g, 12.26 mmol) in methanol (250 ml) was treated with ammonium hydroxide (30%, 150 ml) at room temperature. The reaction mixture was stirred at room temperature for 4 hours and evaporated to dryness under reduced pressure. The residue was purified by flash chromatography over silica gel using $CH_2Cl_2$/MeOH as the eluent. The pure fractions were pooled together and evaporated to dryness to give 5.92 g (81%) of the title compound: $^1$H NMR ($Me_2SO$-$d_6$) δ1.04 (m, 6H, Isobutyryl $CH_3$), 1.96 (m, 2H, $CH_2$), 2.32 (m, 1H, $C_{2'}$H), 2.62 (m, 1H, $C_{2'}$H), 3.14 (m, 1H, Isobutyryl CH), 3.26 (m, 2H, $CH_2$), 3.52 (m, 2H, $C_{5'}CH_2$), 3.82 (m, 3H, $CH_2$ and $C_{4'}$H), 3.96 (m, 2H, $CH_2$), 4.36 (m, 1H, $C_{3'}$H), 4.70 (m, 2H, $CH_2$), 4.96 (b s, 1H, $C_{5'}$OH), 5.42 (b s, 1H, $C_{3'}$OH), 6.34 (t, 1H, $J_{1',2'}$=6.20 Hz, $C_{1'}$H), 6.82 (s, 1H, ImH), 7.12 (s, 1H, ImH), 7.54 (s, 1H, ImH), 7.62 (d, 2H, ArH), 8.16 (d, 2H, ArH), 8.56 (s, 1H, $C_8$H). Anal. Calcd for $C_{28}H_{34}N_8O_7$-½$H_2O$: C, 55.71; H, 5.84; N, 18.56. Found: C, 55.74; H, 5.67; N, 18.43.

EXAMPLE 8

5'-O-(4,4'-Dimethoxytrityl)-6-O-[2-(4-nitrophenyl)ethyl]-$N_2$-isobutyryl-$N_2$-[imidazol-1-yl(propyl)]-(2-deoxy-β-D-erythropentofuranosyl)guanosine. (8)

The substrate 7 (5.94 g, 10 mmol), was dissolved in dry pyridine (75 mL) and evaporated to dryness. This was repeated three times to remove traces of moisture. To this well dried solution of the substrate in dry pyridine (100 mL) was added dry triethylamine (4.04 g, 40 mmol), 4-(dimethylamino)pyridine (1.2 g, 30 mmol) at room temperature. The reaction mixture was stirred at room temperature for 12 hours under an atmosphere of argon. Methanol (50 mL) was added and the stirring was continued for 15 minutes and evaporated to dryness. The residue was purified by flash chromatography over silica gel using dichloromethane-acetone containing 1% triethylamine as the eluent. The pure fractions were pooled together and evaporated to dryness to give 7.2 g (80%) of the title compound as a colorless foam: $^1$H NMR ($Me_2SO$-$d_6$) δ1.04 (m, 6H, Isobutyryl $CH_3$), 1.94 (m, 2H, $CH_2$), 2.34 (m, 1H, $C_{2'}$H), 2.80 (m, 1H, $C_{2'}$H), 3.04 (m, 1H, Isobutyryl CH), 3.18 (m, 2H, $CH_2$), 3.28 (m, 2H, $CH_2$), 3.62 (s, 3H, $OCH_3$), 3.66 (s, 3H, $OCH_3$), 3.74 (2 m, 2H, $C_{5'}CH_2$), 3.98 (m, 3H, $CH_2$ and $C_{4'}$H), 4.36 (m, 1H, $C_{3'}$H), 4.70 (m, 2H, $CH_2$), 5.44 (b s, 1H, $C_{3'}$OH), 6.32 (t, 1H, $J_{1',2'}$=6.20 Hz $C_{1'}$H), 6.64–7.32 (m, 15H, ImH and ArH), 7.52 (s, 1H, ImH), 7.62 (d, 2H, ArH), 8.16 (d, 2H, ArH), 8.42 (s, 1H, $C_8$H). Anal. Calcd for $C_{49}H_{52}N_8O_9$-$H_2O$: C, 64.32; H, 5.95; N, 12.25. Found: C, 64.23; H, 5.85; N, 12.60.

EXAMPLE 9

3'-O-[(N,N-Diisopropylamino)(β-cyanoethoxy)phosphanyl]-5'-O-(4,4'-dimethoxytrityl)-6-O-[2-(4-nitrophenyl)ethyl]-$N_2$-isobutyryl-$N_2$-[imidazol-1-yl(propyl)]-9-(2-deoxy-β-D-erythropentofuranosyl)guanosine. (9)

The substrate of 8 (2.5 g, 2.7 mmol), was dissolved in dry pyridine (30 mL) and evaporated to dryness. This was repeated three times to remove last traces of water and dried over solid sodium hydroxide overnight. The dried 8 was dissolved in dry dichloromethane (30 mL) and cooled to 0° C. under an atmosphere of argon. To this cold stirred solution was added N,N-diisopropylethylamine (0.72 g, 5.6 mmol) followed by (β-cyanoethoxy)chloro(N,N-diisopropylamino) phosphate (1.32 g, 5.6 mmol) dropwise over a period of 15 minutes. The reaction mixture was stirred at 0° C. for 1 hour and at room temperature for 2 hours. The reaction mixture was diluted with dichloromethane (100 mL) and washed with brine (50 mL). The organic extract was dried over anhydrous MgSO$_4$ and the solvent was removed under reduced pressure. The residue was purified by flash chromatography over silica gel using hexane/acetone containing 1% triethylamine as the eluent. The main fractions were collected and evaporated to dryness. The residue was dissolved in dry dichloromethane (10 mL) and added dropwise, into a stirred solution of hexane (1500 mL), during 30 minutes. After the addition, the stirring was continued for an additional 1 hour at room temperature under argon. The precipitated solid was filtered, washed with hexane and dried over solid NaOH under vacuum overnight to give 2.0 g (65%) of the title compound as a colorless powder: $^1$H NMR (Me$_2$SO-d$_6$) δ1.04 (2 m, 18H, 3 Isobutyryl CH$_3$), 1.94 (m, 2H, CH$_2$), 2.44 (m 3H, C$_2$H and 2 Isobutyryl CH), 2.80 (m, 1H, C$_2$H), 3.2 (m, 5H, 2 CH$_2$ and Isobutyryl CH), 3.44–3.98 (m, 12H, CH$_2$, 2 OCH$_3$ and C$_5$CH$_2$), 4.16 (m, 1H, C$_4$H), 4.64 (m, 3H, C$_3$H and CH$_2$), 6.32 (t, 1H, J$_{1',2'}$=6.20 Hz, C$_1$H), 6.64–7.32 (m, 16H, 3 ImH and ArH), 7.44 (d, 2H, ArH), 8.16 (d, 3H, ArH and C$_8$H).

dried. The filtrate was evaporated to dryness and the residue carried over to the next reaction without further purification: $^1$H NMR (Me$_2$SO-d$_6$) δ1.94 (m, 2H, CH$_2$), 2.18 (m, 1H, C$_2$H), 2.36 (m, 1H, C$_2$H), 3.18 (m, 2H, CH$_2$), 3.52 (2 m, 2H, C$_5$CH$_2$), 3.80 (m, 1H, C$_4$H), 4.02 (m, 2H, CH$_2$), 4.36 (m, 1H, C$_3$H), 5.24 (b s, 2H, C$_3$OH and C$_5$OH), 6.18 (t, 1H, J$_{1',2'}$=6.20 Hz, C$_1$H), 6.42 (t, 1H, NH), 6.70 (b s, 2H NH$_2$), 6.96 (s, 1H, ImH), 7.24 (s, 1H, ImH), 7.78 (s, 1H, ImH), 7.90 (s, 1H, C$_8$H). Anal. Calcd for C$_{16}$H$_{22}$N$_8$O$_3$: C, 51.33; H, 5.92; N, 29.93. Found: C, 51.30; H, 5.92; N, 29.91.

EXAMPLE 11

3',5'-O-(Tetraisopropyldisiloxane-1,3-diyl)-N$_2$-(imidazol-1-yl) (propyl)]-9-(2-deoxy-β-D-erythro-pentofuranosyl) aminoadenosine. (12)

The crude product 11 (14.03 g) was dissolved in dry DMF (100 mL) dry pyridine (50 mL), and evaporated to dryness. This was repeated three times to remove all the water. The dried substrate was dissolved in dry DMF (75 mL) and

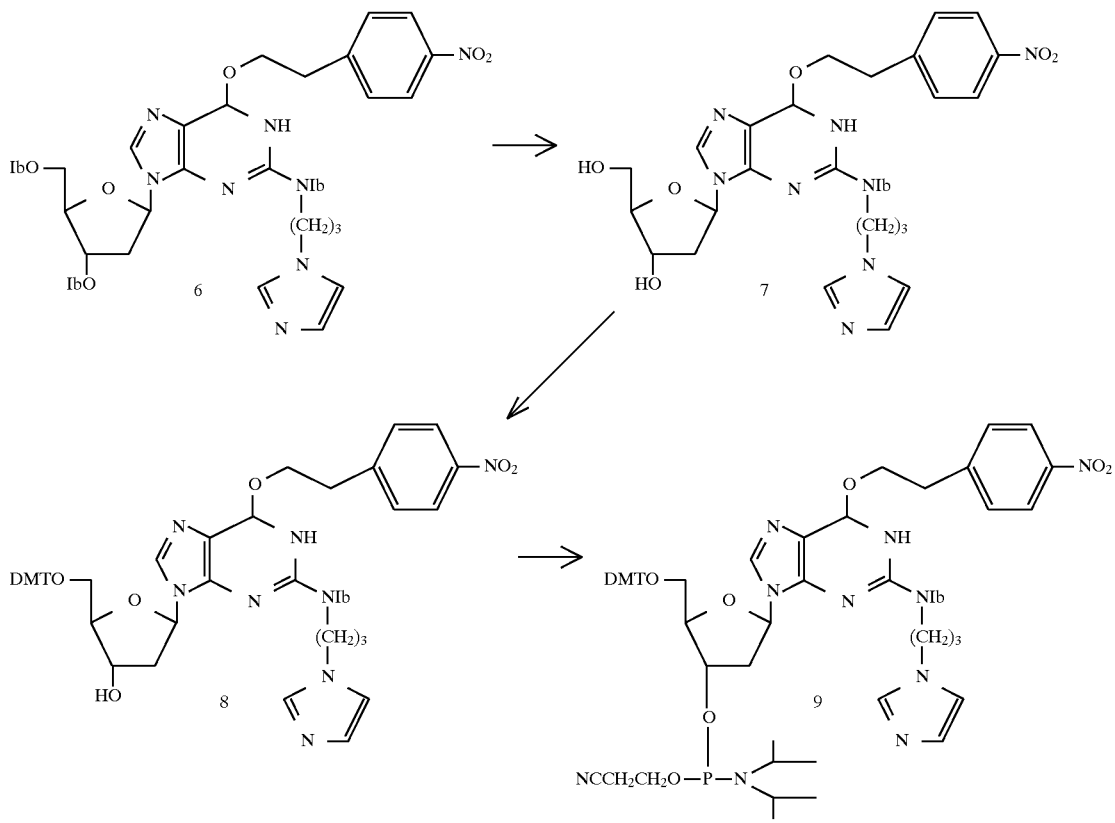

EXAMPLE 10

N$_2$-[Imidazol-1-yl(propyl)]-9-(2-deoxy-β-D-erythro-pentofuranosyl)adenosine. (11)

A suspension of 2-chloro-9-(2'-deoxy-β-D-erythropentofuranosyl)adenosine (10, 10.68 g, 37.47 mmol) and 1-(3 aminopropyl) imidazole (12.5 g, 100 mmol) in 2-methoxyethanol (80 mL) was heated at 125° C. for 45 hours in a steel bomb. The bomb was cooled to 0° C., opened carefully, and evaporated to dryness. The residue was coevaporated several times with a mixture of ethanol and toluene. The residue was dissolved in ethanol which on cooling gave a precipitate. The precipitate was filtered and allowed to stir at room temperature under argon atmosphere. To this stirred solution was added dry triethylamine (10.1 g, 100 mmol) and 1,3-dichloro-1,1,3,3-tetraisopropyldisiloxane (TipSiCl, 15.75 g, 50.00 mmol) during a 15 minute period. After the addition of TipSiCl, the reaction mixture was allowed to stir at room temperature overnight. The reaction mixture was evaporated to dryness. The residue was mixed with toluene (100 mL) and evaporated again. The residue was purified by flash chromatography over silica gel using CH$_2$Cl$_2$/MeOH as eluent. The pure fractions were pooled and evaporated to dryness to give 12.5 g (54%) of 12 as an amorphous powder: $^1$H NMR (Me$_2$SO-d$_6$) δ1.00 (m, 28H), 1.92 (m, 2H, CH$_2$), 2.42 (m, 1H, C₂'H), 2.80 (m, 1H, C₂'H), 3.18 (m, 2H, CH₂), 3.84 (2 m, 3H, C₅'CH₂ and C₄'H), 4.00 (t, 2H, CH₂), 4.72 (m, 1H, C₃'H), 6.10 (m, 1H, C₁'H), 6.48 (t, 1H, NH), 6.74 (b s, 2H, NH₂), 6.88 (s, 1H, ImH), 7.18 (s, 1H, ImH), 7.64 (s, 1H, ImH), 7.82 (s, 1H, C₈H). Anal. Calcd for C₂₈H₅₀N₈O₄Si₂: C, 54.33; H, 8.14; N, 18.11. Found: C, 54.29; H, 8.09; N, 18.23.

EXAMPLE 12

3',5'-O-(Tetraisopropyldisiloxane-1,3-diyl)-N₆-isobutyryl-N₂-[(imidazol-1-yl)propyl]-9-(2-deoxy-β-D-erythro-pentofuranosyl)adenosine. (13)

A solution of 12 (12.0 g, 19.42 mmol) in pyridine (100 mL) was allowed to stir at room temperature with triethylamine (10.1 g, 100 mmol) under an atmosphere of argon. To this stirred solution was added isobutyryl chloride (6.26 g, 60 mmol) dropwise during a 25 minute period. The reaction mixture was stirred under argon for 10 hours and evaporated to dryness. The residue was partitioned between dichloromethane/water and extracted with dichloromethane (2×150 mL). The organic extract was washed with brine (30 mL) and dried over anhydrous MgSO₄. The solvent was removed under reduced pressure and the residue was purified by flash chromatography over silica gel using CH₂Cl₂/acetone as the eluent to give the 13 as a foam: ¹H NMR (Me₂SO-d₆) δ1.00 (m, 34H), 1.92 (m, 2H, CH₂), 2.42 (m, 1H, C₂'H), 2.92 (m, 2H, C₂'H and Isobutyryl CH), 3.24 (m, 2H, CH₂), 3.86 (H, 3H, C₅'CH₂ and C₄'H), 4.40 (m, 2H, CH₂), 4.74 (m, 1H, C₃'H), 6.22 (m, 1H, J₁',₂'=6.20 Hz, C₁'H) 6.82 (t, 1H, NH), 6.92 (s, 1H, ImH), 7.18 (s, 1H, ImH) 7.60 (s, 1H, ImH), 8.12 (s, 1H, C₈H), 10.04 (b s, 1H, NH). Anal. Calcd for C₃₂H₅₄N₈O₅Si₂: C, 55.94; H, 7.92; N, 16.31. Found: C, 55.89; H, 7.82; N, 16.23.

EXAMPLE 13

3',5'-Di-O-isobutyryl-N₂-[imidazol-1-yl (propyl)]-N₆-isobutyryl-9-(2-deoxy-β-D-exythro-pentofuranosyl)adenosine. (14)

The crude product 11 (9.2 g, 24.59 mmol) was coevaporated three times with dry DMF/pyridine (100:50 mL). The above dried residue was dissolved in dry DMF (100 mL) and dry pyridine (100 mL) and cooled to 0° C. To this cold stirred solution was added triethylamine (20.2 g, 200 mmol) followed by isobutyryl chloride (15.9 g, 150 mmol). After the addition of isobutyryl chloride, the reaction mixture was allowed to stir at room temperature for 12 hours. The reaction mixture was evaporated to dryness. The residue was extracted with dichloromethane (2×200 mL), washed with 5% NaHCO₃ (50 mL) solution, water (50 mL), and brine (50 mL). The organic extract was dried over dry MgSO₄ and the solvent was removed under reduced pressure. The residue was purified by flash column using CH₂Cl₂/acetone (7:3) as the eluent. The pure fractions were collected together and evaporated to give 7.0 g (44%) of 14 as a foam: ¹H NMR (Me₂SO-d₆) δ1.00 (m, 18H, 3 Isobutyryl CH₃), 1.98 (m, 2H, CH₂), 2.42 (m, 3H, C₂'H and 2 Isobutyryl CH), 2.92 (m, 2H, C₂'H and Isobutyryl CH), 3.24 (m, 2H, CH₂), 4.04 (m, 2H, CH₂), 4.22 (m, 3H, C₅'CH₂ and C₄'H), 5.42 (m, 1H C₃'H), 6.24 (t, 1H, J₁',₂'=6.20 Hz, C₁'H), 7.04 (s, 1H, ImH), 7.12 (t, 1H, NH), 7.32 (s, 1H, ImH), 8.00 (s, 1H, ImH), 8.12 (s, 1H, C₈H), 10.14 (b s, 1H, NH). Anal. Calcd for C₂₈H₄₀N₈O₆: C, 57.52; H, 6.89; N, 19.17. Found: C, 57.49; H, 6.81: N, 19.09.

EXAMPLE 14

N₆-Isobutyryl-N₂-[imidazol-1-yl (propyl)]-9-(2-deoxy-β-D-erythropentofuranosyl)adenosine. (15)

Method 1: To a stirred solution of 13 (2.6 g, 3.43 mmol) in dry tetrahydrofuran (60 mL) was added tetrabutylammonium flouride (1M solution in THF, 17.15 mL, 17.15 mmol) at room temperature. The reaction mixture was stirred at room temperature for I hour and quenched with H⁺ resin. The resin was filtered, and washed with pyridine (20 mL) and methanol (50 mL). The filtrate was evaporated to dryness and the residue on purification over silica column using CH₂Cl₂/MeOH (95:5) gave the title compound in 59% (1 g) yield: ¹H NMR (Me₂SO-d₆) δ1.04 (m, 6H, Isobutyryl CH₃), 1.98 (m, 2H, CH₂), 2.22 (m, 1H, Isobutyryl CH), 2.70 (m, 1H, C₂'H), 2.98 (m, 1H, C₂'H), 3.22 (m, 2H CH₂), 3.52 (2 m, 2H, C₅'CH₂), 3.82 (m, 1H, C₄'H), 4.04 (m, 2H, CH₂), 4.38 (m, 1H, C₃'H), 4.92 (b s, 1H, OH), 5.42 (b s, 1H, OH) 6.22 (t, 1H, J₁',₂'=6.20 Hz, C₁'H), 6.92 (s, 1H, ImH), 7.06 (t, 1H, NH), 7.24 (s, 1H, ImH), 7.74 (s, 1H, ImH), 8.12 (s, 1H, C₈H), 10.08 (b s, 1H, NH). Anal. Calcd for C₂₀H₂₈N₈O₄·H₂O; C, 54.04; H, 6.35; N, 25.21. Found: C, 54.14; H, 6.53; N, 25.06.

Method 2: To an ice cold (0° to –5° C.) solution of 14 (7.4 g. 12.65 mmol) in pyridine:EtOH:H₂O (70:50:10 mL) was added 1N KOH solution (0° C., 25 mL, 25 mmol). After 10 minutes of stirring, the reaction was quenched with H⁺ resin (pyridinium form) to pH 7. The resin was filtered, and washed with pyridine (25 mL) and methanol (100 mL). The filtrate was evaporated to dryness and the residue was purified by flash chromatography over silica gel using CH₂Cl₂/MeOH (9:1) as eluent. The pure fractions were pooled together and evaporated to give 1.8 g (37%) of 15.

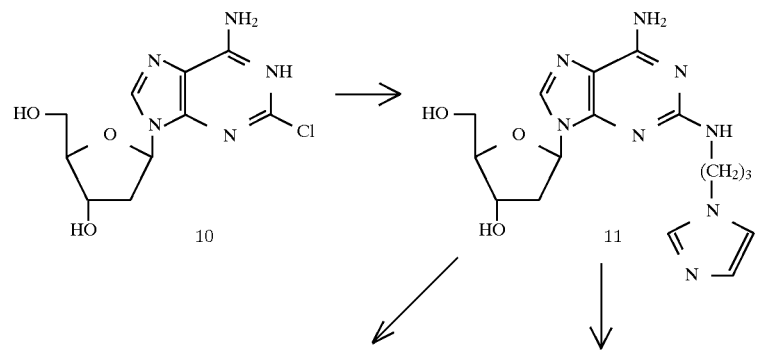

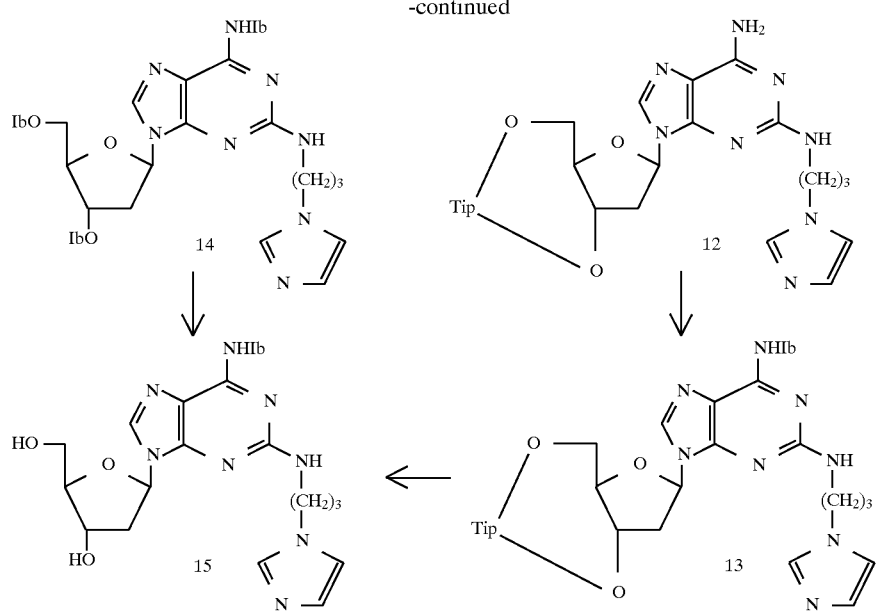

EXAMPLE 15

5'-O-(4,4'-Dimethoxytrityl)-N₆-isobutyryl-N₂-[imidazol-1-yl (propyl)]-9-(2-deoxy-β-D-exythro-pentofuranosyl)adenosine. (16)

To a well dried (coevaporated three times with dry pyridine before use) solution of 15 (3.6 g, 8.11 mmol) in dry pyridine (100 mL) was added triethylamine (1.01 g, 10.00 mmol) followed by 4,4'-dimethoxytrityl chloride (3.38 g, 10.00 mmol) at room temperature. The reaction mixture was stirred under argon for 10 hours and quenched with methanol (20 mL). After stirring for 10 minutes, the solvent was removed under reduced pressure. The residue was dissolved in dichloromethane (250 mL), washed with water (50 mL), and brine (50 mL), and dried over MgSO₄. The dried organic extract was evaporated to dryness to an orange foam. The foam was purified by flash chromatography over silica gel using CH₂Cl₂/MeOH (95:5) as eluent. The required fractions were collected together and evaporated to give 4.6 g (76%) of 16 as amorphous solid: ¹H NMR (Me₂SO-d₆) δ1.04 (m, 6H, Isobutyryl CH₃), 1.90 (m, 2H, CH₂), 2.30 (m, 1H, C₂'H), 2.82 (m, 1H, C₂'H), 2.94 (m, 1H, Isobutyryl CH), 3.14 (m, 4H, CH₂ and C₅'C₂), 3.72 (m, 6H, OCH₃), 3.92 (m, 3H, CH₂ and C₄'H), 4.44 (m, 1H, C₃'H), 5.44 (b s, 1H, C₅'OH), 6.28 (t, 1H, J₁',₂'=6.20 Hz, C₁'H), 6.72–7.32 (m, 18H, ImH, NH and ArH), 7.64 (s, 1H ImH), 8.02 (s, 1H, C₈H), 10.10 (b s, 1H, NH). Anal. Calcd for C₄₁H₄₆N₈O₆: C, 65.93; H, 6.21; N, 15.00. Found: C, 65.81; H, 6.26; N, 14.71.

EXAMPLE 16

3'-O-[(N,N-diisopropylamino) (β-cyanoethoxy) phosphanyl]-5'-O-(4,4'-dimethoxytrityl)-N₆-isobutyryl-N₂-[imidazol-1-yl(propyl)]-9-(2-deoxy-β-D-erythro-pentofuranosyl)adenosine. (17)

The substrate 16 (4.2 g, 5.6 mmol) was coevaporated with dry pyridine(50 mL) three times. The resulting residue was dissolved in dry dichloromethane (50 mL) and cooled to 0° C. in a ice bath. To this cold stirred solution was added N,N-diisopropylethylamine (1.44 g, 11.2 mmol) followed by (β-cyanoethoxy)chloro(N,N-diisopropyl-amino)phosphane (1.32 g, 5.6 mmol) over a period of 15 minutes. After the addition, the reaction mixture was stirred at 0° C. for 1 hour and room temperature for 2 hours. The reaction was diluted with dichloromethane (150 mL) and washed with 5% NaHCO₃ solution (25 mL) and brine (25 mL). The organic extract was dried over MgSO₄ and the solvent was removed under reduced pressure. The residue was purified by flash chromatography over silica gel using CH₂Cl₂/MeOH (98:2) containing 1% triethylamine as eluent. The pure fractions were collected together and evaporated to dryness to give 3.9 g (73%) of 17.

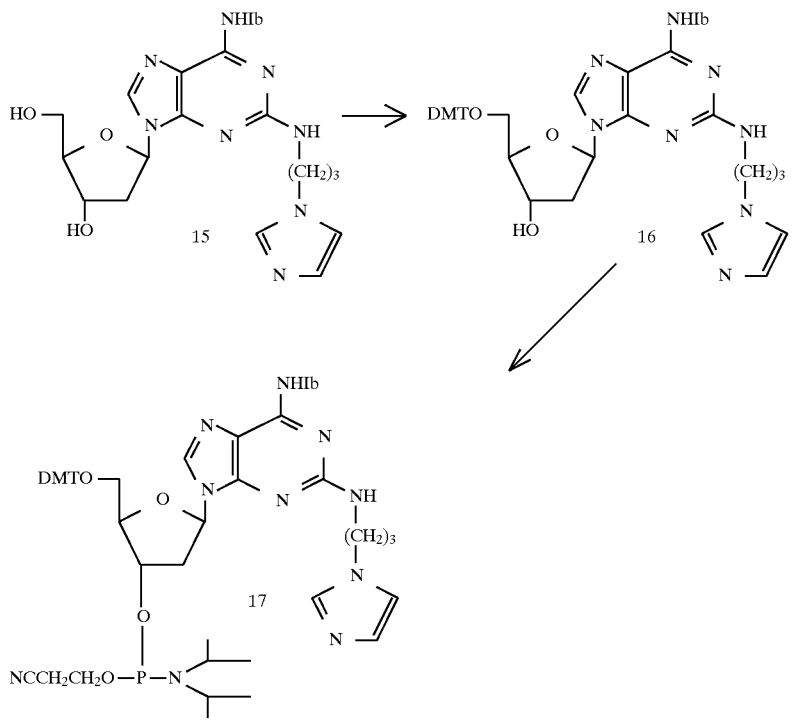

EXAMPLE 17

N$_2$-[Imidazol-4-yl(ethyl)]-9-(2-deoxy-β-D-erythro-pentofuranosyl)guanosine. (18)

A mixture of 3 and histamine (4.4 g, 40.00 mmol) in 2-methoxyethanol (60 mL) was heated at 110° C. in a steel bomb for 12 hours. The steel bomb was cooled to 0° C., opened carefully, and the precipitated solid was filtered, washed with acetone and dried. The dried material was recrystallized from DMF/H$_2$O for analytical purposes. Yield 6 g (79%): mp 220°–22° C.: $^1$H NMR (Me$_2$SO-d$_6$) δ2.22 (m, 1H, C$_{2'}$H), 2.64 (m, 1H, C$_{2'}$H), 2.80 (m, 1H, CH$_2$), 3.52 (m, 4H, CH$_2$ and C$_{5'}$CH$_2$), 3.80 (m, 1H, C$_{4'}$H), 4.42 (m, 1H, C$_{3'}$H), 4.98 (b s, 1H, C$_{5'}$OH), 5.44 (b s, 1H, C$_{3'}$OH), 6.16 (t, 1H, J$_{1',2'}$=6.20 Hz, C$_{1'}$H), 6.44 (b s, 1H, NH), 6.84 (s, 1H, ImH), 7.56 (s, 1H, ImH), 7.92 (s, 1H, C$_8$H), 10.60 (b s, 1H, NH), 11.90 (b s, 1H, NH). Anal. Calcd for C$_{15}$H$_{19}$N$_7$O$_4$: C, 49.85; H, 5.30; N, 27.13. Found: C, 49.61; H, 5.21; N, 26.84.

EXAMPLE 18

3',5'-O-(Tetraisopropyldisiloxane-1,3-diyl)-N$_2$-(imidazol-4-yl(ethyl))-9-(2-deoxy-β-D-erythro-pentofuranosyl)guanosine. (19)

To a stirred suspension of 18 (2.4 g, 6.65 mmol) in dry DMF (50 mL) and dry pyridine (20 mL) was added triethylamine (4.04 g, 40.00 mmol) followed by 1,3-dichloro-1,1,3,3-tetraisopropyldisiloxane (4.18 g, 13.3 mmol) at room temperature. After the addition of TipSiCl, the reaction mixture was stirred overnight and evaporated to dryness. The residue was purified by flash chromatography over silica gel using CH$_2$Cl$_2$/MeOH (9:1) as eluent. The pure fractions were pooled together and evaporated to dryness to give 3.2 g (80%) of 19. The pure product was crystallized from acetone/dichloromethane as colorless solid. mp 245°–247° C.: $^1$H NMR (Me$_2$SO-d$_6$) δ1.00 (m, 28H), 2.46 (m, 1H, C$_{2'}$H), 2.72 (m, 1H, C$_{2'}$H), 2.84 (m, 1H, CH$_2$), 3.54 (m, 2H, CH$_2$), 3.90 (m, 3H, C$_{4'}$H and C$_{5'}$CH$_2$), 4.70 (m, 1H, C$_{3'}$H), 6.12 (t, 1H, J$_{1',2'}$=6.20 Hz, C$_{1'}$H), 6.68 (b s, 1H, NH), 7.20 (s, 1H, ImH), 7.80 (s, 1H, ImH), 8.40 (s, 1H, C$_8$H), 10.72 (b s, 1H, NH). Anal. Calcd for C$_{27}$H$_{45}$N$_7$O$_5$Si$_2$: C, 53.70; H, 7.51; N, 16.24. Found: C, 53.38; H, 7.63; N, 15.86.

EXAMPLE 19

3'5'-O-(Tetraisopropyldisiloxane-1,3-diyl)-6-O-diphenylcarbamoyl-N$_2$-[(N$_1$-diphenylcarbamoyl)imidazol-4-yl(ethyl)]-9-(2-deoxy-β-D-exythro-pentofuranosyl)guanosine. (20)

To a well stirred solution of the substrate 19 (6.03 g, 10.00 mmol) in dry DMF (50 mL) and dry pyridine (50 mL) was added N,N-diisopropylethylamine (5.16 g, 40.00 mmol) followed by diphenylcarbamoyl chloride (6.93 g, 30.00 mmol) at room temperature. The reaction mixture was allowed to stir at room temperature for 5 hours and evaporated to dryness. The residue was dissolved in CH$_2$Cl$_2$ (400 mL), washed with water (100 mL) and brine (50 mL), dried over MgSO$_4$, and evaporated to dryness. The residue was purified by flash chromatography using hexane/acetone (8:2) to give 7.8 g (78%) of 20: $^1$H NMR (Me$_2$SO-d$_6$) δ1.04 (m,28H), 2.54 (m, 1H, C$_{2'}$H), 2.65 (m, 1H, C$_{2'}$H), 2.72 (m, 2H, CH$_2$), 3.64 (m, 2H, CH$_2$), 3.86 (m, 1H, C$_{4'}$H), 4.00 (m, 2H, C$_{5'}$CH$_2$), 4.74 (m, 1H, C$_{3'}$H), 5.30 (b s, 1H, NH), 6.22 (m, 1H, C$_{1'}$H), 6.72 (s, 1H, ImH), 7.12–7.50 (m, 20H, ArH), 7.70 (s, 1H, ImH), 7.86 (s, 1H, C$_8$H). Anal. Calcd for C$_{53}$H$_{63}$N$_9$O$_7$Si$_2$: C, 64.02; H, 6.39; N, 12.68. Found: C, 64.13; H, 6.43; N, 12.79.

EXAMPLE 20

6-O-Diphenylcarbamoyl-N$_2$-[(N$_1$-diphenylcarbamoyl)imidazol-4-yl(ethyl)]-9-(2-deoxy-β-D-erythro-pentofuranosyl)guanosine. (21)

To a stirred solution of the protected derivative of 20 (1.8 g, 1.81 mmol) in pyridine/THF (30:20 mL) was added a 0.5M tetrabutyl-ammonium flouride [prepared in a mixture of tetrahydrofuran-pyridine-water (8:1:1;v/v/v; 20 mL)] at room temperature. The reaction mixture was stirred for 15 minutes and quenched with H+ resin (pydinium form) to pH 6-7. The resin was filtered off, and washed with pyridine (25 mL) and methanol (30 mL). The filtrate was evaporated to dryness and the residue was purified by flash chromatography using $CH_2Cl_2$/MeOH (95:5) to give 1.2 g (88%) of 21 as a colorless amorphous solid: $^1$H NMR ($Me_2SO-d_6$) δ2.32 (m, 1H, $C_2$'H), 2.72 (m, 2H, $CH_2$), 2.94 (m, 1H, $C_2$'H), 3.46 (m, 1H, $C_4$'H), 3.54–3.88 (m, 4H, $CH_2$ and $C_5$'$CH_2$), 4.00 (b s, 1H, $C_3$'H), 5.20 (b s, 2H, OH), 5.42 (t, 1H, NH), 6.10 (t, 1H, $J_{1',2'}$=6.20 Hz $C_1$'H), 6.80 (s, 1H, ImH), 7.14–7.48 (m, 20H, ArH), 7.64 (s, 1H, ImH), 7.74 (s, 1H, $C_8$H). Anal. Calcd for $C_{41}H_{37}N_9O_6$: C, 65.50; H, 4.96; N, 16.77. Found: C, 65.31; H, 5.10; N, 16.40.

(0.85 g, 2.5 mmol) at room temperature. The stirring was continued overnight under argon atmosphere. Methanol (10 mL) was added, stirred for 10 minutes and evaporated to dryness. The residue was dissolved in $CH_2Cl_2$ (150 mL), washed with water (20 mL) and brine (20 mL), dried over $MgSO_4$, and the solvent removed under reduced pressure. The crude product was purified by flash chromatography over silica gel using $CH_2Cl_2$/acetone (7:3) containing 1% triethylamine as eluent. Yield 1.4 g (71%): $^1$H NMR ($Me_2SO-d_6$) δ2.44 (m, 1H, $C_2$'H), 2.62 (m, 2H, $CH_2$), 2.98 (m, 1H, $C_2$'H), 3.26 (m, 4H, $CH_2$ and $C_5$'$CH_2$), 3.40 (m, 1H, $C_4$'H), 3.68 (2 s, 6H, 2H $OCH_3$), 4.00 (m, 1H, $C_3$'H), 5.34 (t, 1H, NH), 5.44 (b s, 1H, $C_3$'OH), 6.12 (m, 1H, $C_1$'H), 6.66–7.48 (m, 34H, ImH and ArH), 7.62 (s, 1H, ImH), 7.78 (s, 1H, $C_8$H). Anal. Calcd for $C_{62}H_{55}N_9O_{84}$: C, 70.64; H, 5.26; N, 11.96. Found: C, 70.24; H, 5.39; N, 11.66.

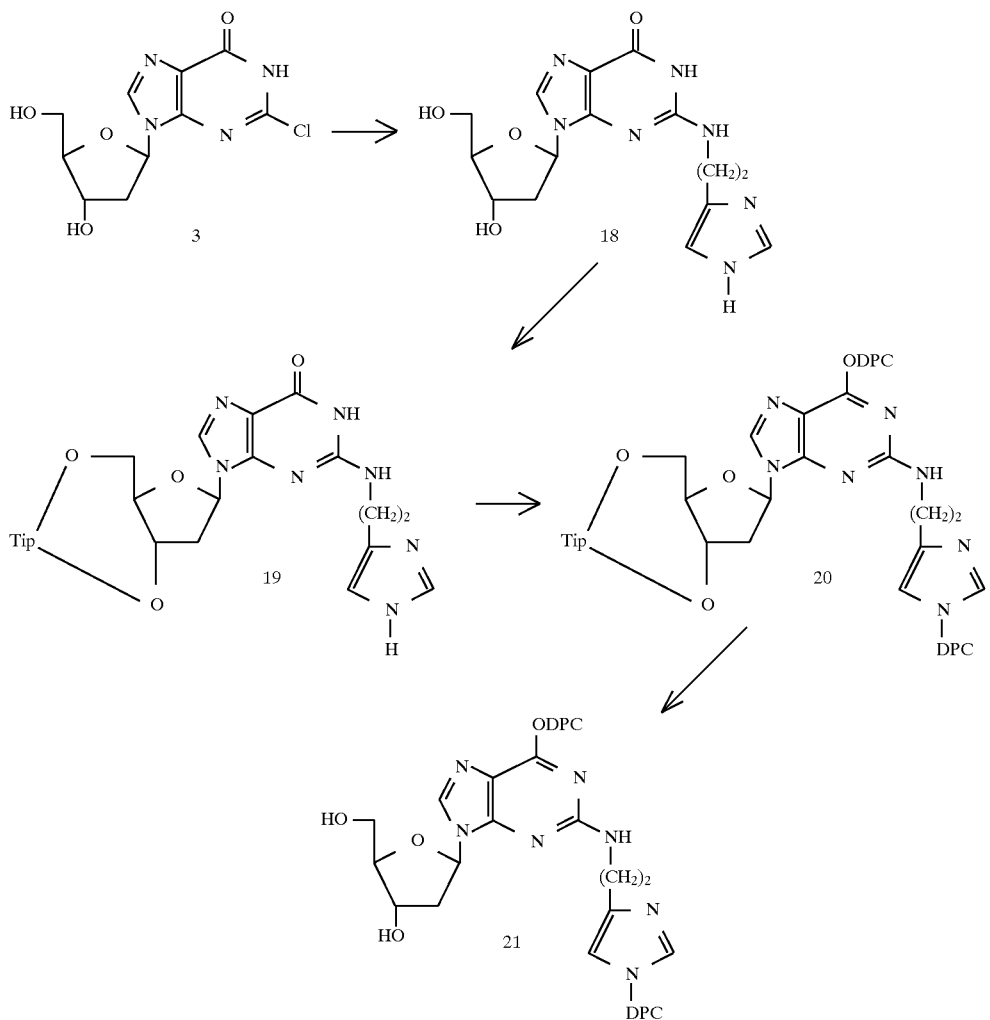

EXAMPLE 21

5'-O-(4,4'-Dimethoxytrityl)-6-diphenylcarbamoyl-$N_2$-[($N_1$-diphenylcarbamoyl)imidazol-4-yl(ethyl)]-9-(2-deoxy-β-D-erythropentofuranosyl) guanosine. (22)

To a well dried solution of the substrate 21 (1.4 g, 1.87 mmol) in dry pyridine (70 mL) was added triethylamine (0.30 g, 3.0 mmol) followed by 4,4'-dimethoxytrityl chloride

EXAMPLE 22

3'-O-[(N,N-Diisopropylamino) (β-cyanoethoxy) phosphanyl]-5'-O-(4,4'-dimethoxytrityl)-6-0-diphenylcarbamoyl-$N_2$-[($N_1$diphenylcarbamoyl) imidazol-4-yl(ethyl)]-9-(2-deoxy-β-D-erythropentofuranosyl)guanosine. (23)

Well dried 22 was dissolved in dry dichloromethane (30 mL) and cooled to 0° C. under argon atmosphere. To this cold stirred solution was added N,N-diisopropylethylamine (0.39 g, 3.00 mmol) followed by (β-cyanoethoxy)chloro (N,N-diisopropylamino)phosphane (0.71 g, 3.0 mmol) over a period of 10 minutes. The reaction mixture was allowed to stir at room temperature for 2 hours and diluted with $CH_2Cl_2$ (120 mL). The organic layer was washed with 5% $NaHCO_3$ (25 mL), water (25 mL), and brine (25 mL). The extract was dried over anhydrous $MgSO_4$ and evaporated to dryness. The residue was purified by flash using hexane/ethyl acetate (3:7) containing 1% triethylamine as eluent. The pure fractions were pooled together and concentrated to dryness to give 1.0 g (70%) of 23 as a foam: $^1H$ NMR ($Me_2SO-d_6$) δ1.12 (m, 12H, 2 Isobutyryl $CH_3$), 2.52 (m, 5H, $C_{2'}H$, $CH_2$ and Isobutyryl CH), 2.62 (m, 2H), 3.06 (m, 1H, $C_{2'}H$), 3.24 (m, 2H, $CH_2$) 3.40 (m, 2H, $CH_2$), 3.50–3.80 (m, 10H, 2 $OCH_3$, $CH_2$ and $C_{5'}CH_2$), 4.08 (m, 1H, $C_{4'}H$), 4.82 (m, 1H, $C_{3'}H$), 5.74 (b s, 1H, NH), 6.24 (m, 1H, $C_{1'}H$), 6.64–7.52 (m, 34H, ImH and ArH), 7.62 (s, 1H, ImH), 7.94 (s, 1H, $C_8H$).

1H, $C_{4'}H$), 4.32 (m, 1H, $C_{3'}H$), 4.84 (t, 1H, $C_{5'}OH$), 5.24 (m, 1H, $C_{3'}OH$), 6.12 (m, 1H, $C_{1'}H$), 6.44 (b s, 1H, NH), 7.86 (s, 1H, $C_8H$), 10.52 (b s, 1H, NH). Anal. Calcd for $C_{19}H_{31}N_5O_4 \cdot H_2O$: C, 55.45; H, 8.08; N, 17.00. Found: C, 55.96; H, 7.87; N, 16.59.

EXAMPLE 24

3',5'-Di-O-isobutyryl-$N_2$-isobutyryl-$N_2$-nonyl-9-(2-deoxy-β-D-erythro-pentofuranosyl)guanosine. (25)

The crude product of 24 (18 g, 32.91 mmol) was coevaporated three times with a mixture of dry DMF/pyridine (50 mL each). The residue was dissolved in dry pyridine (150 mL) and cooled to 0° C. To this cold stirred solution was added triethylamine (30.3 g, 300 mmol) followed by isobutyryl chloride (21.2 g, 200 mmol) over a 30 minute period. After the addition of IbCl, the reaction mixture was allowed to stir at room temperature for 10 hours and was then

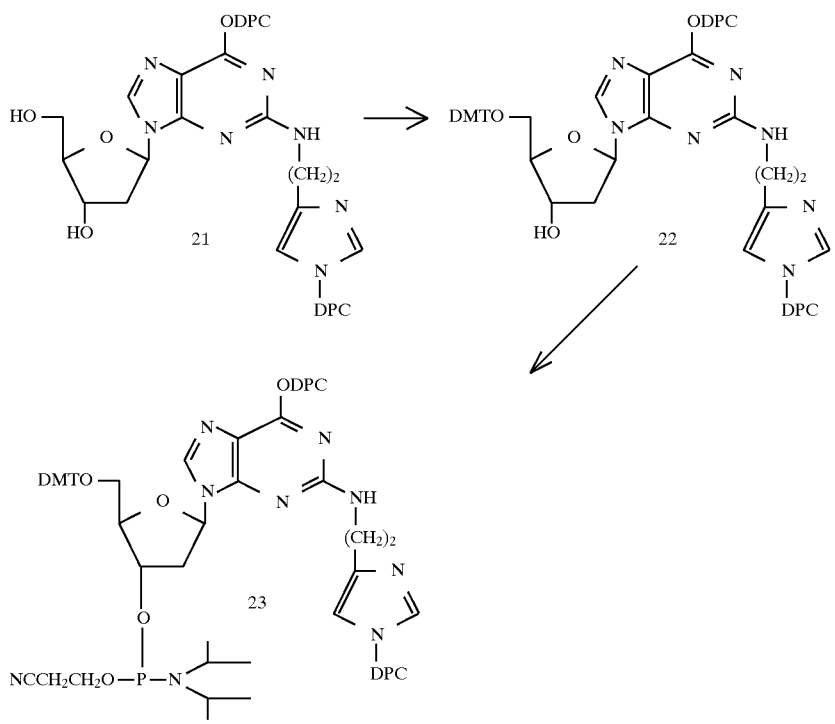

EXAMPLE 23

$N_2$,Nonyl-9-(2-deoxy-β-D-erythro-pentofuranosyl) guanosine. (24)

A mixture of 2-chloro-2'-deoxyinosine and compound 3 (9.5 g, 33.22 mmol) and nonylamine (9.58 g, 67.00 mmol) in 2-methoxyethanol (60 mL) was heated at 120° C. for 12 hours in a steel bomb. The steel bomb was cooled to 0° C., opened carefully and the solvent removed under reduced pressure. The residue was coevaporated with a mixture of dry pyridine/dry toluene (50 mL each). The above process was repeated for three times and the resultant residue was carried over to the next reaction without further purification. A small amount of material was precipitated from the solution which was filtered and dried: mp 164°–167° C.: $^1H$ NMR ($Me_2SO-d_6$) δ0.82 (t, 3H, $CH_3$), 1.24 (m, 12H, 6 $CH_2$), 1.48 (m, 2H, $CH_2$), 2.18 (m, 1H, $C_{2'}H$), 2.62 (m, 1H, $C_{2'}H$), 3.22 (m, 2H, $CH_2$), 3.50 (m, 2H, $C_{5'}CH_2$), 3.78 (m, evaporated to dryness. The residue was partitioned between $CH_2Cl_2$/water (300:150 mL) and extracted in $CH_2Cl_2$. The organic extract was washed with 5% $NaHCO_3$ (50 mL), water (50 mL) and brine (50 mL), dried over anhydrous $MgSO_4$, and evaporated to dryness. The residue was purified by flash chromatography over silica gel using $CH_2Cl_2$/ EtOAc (6:4) as eluent. The pure fractions were pooled and evaporated to give 10 g (40%) of 25 as foam: $^1H$ NMR ($Me_2SO-d_6$) δ0.82 (t, 3H, $CH_3$), 1.12 (m, 30H, 3 Isobutyryl $CH_3$ and 6 $CH_2$), 1.44 (m, 2H, $CH_2$), 2.54 (m, 4H, $C_{2'}H$ and 3 Isobutyryl CH), 3.00 (m, 1H, $C_{2'}H$), 3.62 (m, 2H, $CH_2$), 4.20 (m, 3H, $C_{5'}CH_2$ and $C_{4'}H$), 5.32 (m, 1H, $C_{3'}H$), 6.24 (t, 1H, $J_{1', 2'}$, 6.20 Hz, $C_{1'}H$), 8.28 (s, 1H, $C_8H$), 12.82 (b s, 1H, NH). Anal. Calcd for $C_{31}H_{49}N_5O_7$: C, 61.67; H, 8.18; N, 11.60. Found: C, 61.59; H, 8.23; N, 11.34.

EXAMPLE 25

3',5'-O-(Tetraisopropyldisiloxane-1,3-diyl)-$N_2$-nonyl-9-(2-deoxy-β-D-erythro-pentofuranosyl) guanosine. (26)

To a well dried solution of the crude product of 24 (16.4 g, 30.00 mmol) in dry DMF (100 mL) and dry pyridine (100 mL) was added triethylamine (10.1 g, 100 mmol) and 1,3-dichloro-1,1,3,3-tetraisopropyldisiloxane (15.75 g, 50 mmol) during 30 min period. The reaction mixture was allowed to stir at room temperature overnight and was then evaporated to dryness. The crude product was dissolved in $CH_2Cl_2$ (300 mL), washed with water (100 mL), and brine (50 mL). The extract was dried over $MgSO_4$ and the solvent was removed under reduced pressure. The residue was purified over silica column using $CH_2Cl_2$/acetone (7:3) to give 14 g (59%) of 26 as colorless foam. This on crystallization with the same solvent provided crystalline solid. mp 210°–212° C.: $^1$H NMR ($Me_2SO-d_6$) δ0.82 (m, 3H, $CH_3$), 1.02 (m, 28H), 1.24 (m, 12H, 6 $CH_2$), 1.50 (m, 2H, $CH_2$), 2.42 (m, 1H, $C_{2'}H$), 2.84 (m, 1H, $C_{2'}H$), 3.24 (m, 2H, $CH_2$), 3.82 (m, 2H, $C_{5'}CH_2$), 3.92 (m, 1H, $C_{4'}H$), 4.72 (m, 1H, $C_{3'}H$), 6.12 (t, 1H, $J_{1',2'}$=6.20 Hz, $C_{1'}H$), 6.36 (b s, 1H, NH), 7.78 (s, 1H, $C_8H$), 10.38 (b s, 1H, NH). Anal. Calcd for $C_{31}H_{57}N_5O_5Si_2$: C, 58.54; H, 9.03; N, 11.01. Found: C, 58.64; H, 9.09; N, 10.89.

EXAMPLE 26

$N_2$-Isobutyryl-3',5'-O-(tetraisopropyldisiloxane-1,3-diyl)-$N_2$-nonyl-9-(2-deoxy-β-D-erythro-pentofuranosyl)guanosine. (27)

To a solution of 26 (14.0 g, 17.72 mmol) in dry DMF (50 mL) and dry pyridine (150 mL) was added triethylamine (3.54 g, 35.00 mmol) and isobutyryl chloride (3.71 g, 3.5 mmol). The reaction mixture was stirred at room temperature overnight and evaporated to dryness. The residue was dissolved in $CH_2Cl_2$ (250 mL), washed with 5% $NaHCO_3$ (50 mL), water (50 mL) and brine (50 mL), dried over $MgSO_4$, and the solvent removed under reduced pressure. The residue was purified by flash chromatography over silica gel using $CH_2Cl_2$/acetone (9:1) as eluent. The pure fractions were pooled together and evaporated to dryness to give 12.0 g (77%) of the title compound as foam: $^1$H NMR ($Me_2SO-d_6$) δ0.80 (m, 3H, $CH_3$), 0.98 (m, 34H), 1.20 (m, 12H, 6 $CH_2$), 1.42 (m, 2H, $CH_2$), 2.52 (m, 2H, $C_{2'}H$ and Isobutyryl CH), 2.82 (m, 1H, $C_{2'}H$), 3.62 (m, 2H, $CH_2$), 3.84 (m, 3H, $C_{5'}CH_2$ and $C_{4'}H$), 4.72 (m, 1H, $C_{3'}H$), 6.22 (t, 1H, $J_{1',2'}$=6.20 Hz, $C_{1'}H$), 8.18 (s, 1H, $C_8H$), 12.80 (b s, 1H, NH).

EXAMPLE 27

$N_2$-Isobutyryl-$N_2$-nonyl-9-(2-deoxy-β-D-erythro-pentofuranosyl)guanosine. (28)

Method 1: The substrate of 25 (5.00 g, 6.6 mmol) was dissolved in methanol (100 mL) and treated with concentrated $NH_4OH$ (100 mL). The reaction mixture was stirred for 4 hours at room temperature and evaporated to dryness. The residue was purified by flash chromatography over silica gel using $CH_2Cl_2$/MeOH (95:5) as eluent. The required fractions were collected together and evaporated to dryness and the residue on crystallization from $CH_2Cl_2$/acetone gave a colorless crystalline solid. yield 2 g (66%): mp 113°–115° C.

Method 2: A stirred solution of 27 (4.29 g, 4.99 mmol) in dry tetrahydrofuran (50 mL) was treated with 1M solution of tetrabutylammonium fluoride (20 mL, 20.00 mmol). The reaction mixture was stirred at room temperature for 4 hours and evaporated to dryness. The residue was purified by flash chromatography using $CH_2Cl_2$/MeOH (95:5) to give 1.59 g (69%) of 28: $^1$H NMR ($Me_2SO-d_6$) δ0.80 (m, 3H, $CH_3$), 0.98 (m, 6H, Isobutyryl $CH_3$), 1.16 (m, 12H, 6 $CH_2$), 1.42 (m, 2H, $CH_2$), 2.24 (m, 1H, $C_{2'}H$), 2.52 (m, 2H, $C_{2'}H$ and Isobutyryl CH), 3.50 (m, 2H, $C_{5'}CH_2$), 3.62 (m, 2H, $CH_2$), 3.82 (m, 1H, $C_{4'}H$), 4.36 (m, 1H, $C_{3'}H$), 4.94 (t, 1H, $C_{5'}OH$), 5.34 (m, 1H, $C_{3'}OH$), 6.22 (t, 1H, $J_{1',2'}$=6.20 Hz, $C_{1'}H$), 8.28 (s, 1H, $C_8H$), 12.78 (b s, 1H, NH). Anal. Calcd for $C_{23}H_{37}N_5O_5$: C, 59.59; H, 8.05; N, 15.11. Found: C, 59.50; H, 8.08; N, 15.06.

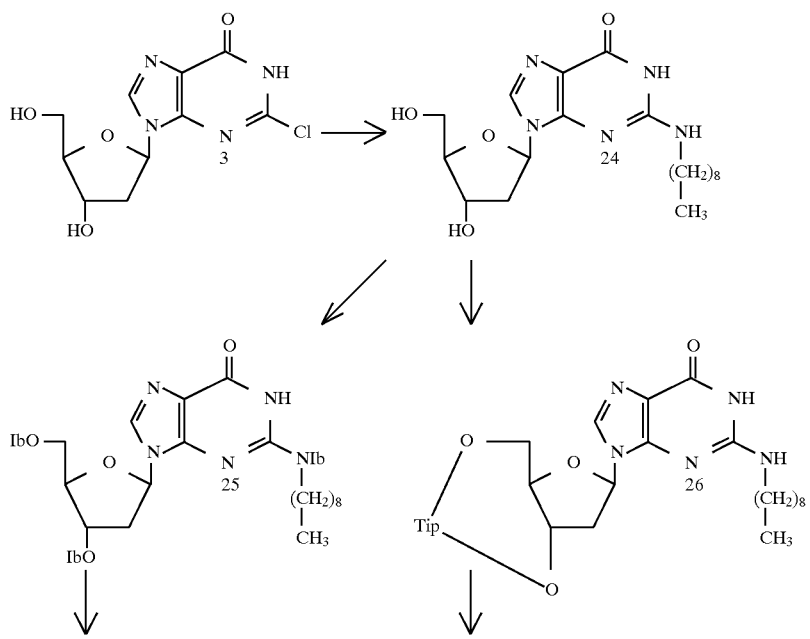

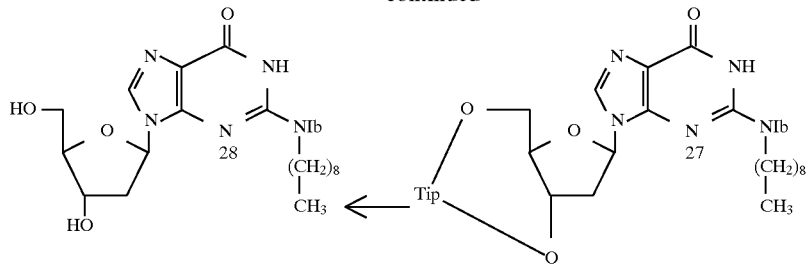

EXAMPLE 28

5'-O-(4,4'-Dimethoxytrityl)-N₂-isobutyryl-N₂-nonyl-9-(2-deoxy-β-D-erythro-pentofuranosyl) guanosine. (29)

To a stirred solution of 28 (2.00 g, 4.32 mmol) in dry pyridine (75 mL) was added triethylamine (0.61 g, 6.00 mmol) and 4,4'-dimethoxytrityl chloride (2.03 g, 6.00 mmol) at room temperature. The reaction was stirred under argon atmosphere for 6 hours and quenched with methanol (10 mL). The solvent was removed under reduced pressure and the residue dissolved in $CH_2Cl_2$ (150 mL). The organic extract was washed with water (25 mL) and brine (25 mL), dried over $MgSO_4$, and evaporated to dryness. The residue was purified by flash chromatography over silica gel using $CH_2Cl_2$/acetone (7:3) as eluent. The pure fractions were pooled together and evaporated to give 2 g (60%) of 29 as foam: $^1$H NMR ($Me_2SO$-$d_6$) δ0.80 (m, 3H, $CH_3$), 0.96 (m, 6H, Isobutyryl $CH_3$), 1.16 (m, 12H, 6 $CH_2$), 1.36 (m, 2H, $CH_2$), 2.32 (m, 1H, $C_{2'}H$), 2.60 (m, 1H, Isobutyryl CH), 2.72 (m, 1H, $C_{2'}H$), 3.12 (m, 2H, $CH_2$), 3.52 (m, 2H, $C_{5'}CH_2$), 3.70 (2 d, 6H, 2 $OCH_3$), 3.90 (m, 1H, $C_{4'}H$), 4.34 (m, 1H, $C_{3'}H$), 5.36 (m, 1H, $C_{3'}OH$), 6.26 (t, 1H, $J_{1',2'}$=6.20 Hz, $C_{1'}H$), 6.70–7.36 (m, 13H, ArH), 8.18 (s, 1H, $C_8H$). Anal. Calcd for $C_{44}H_{56}N_5O_7$: C, 68.90; H, 7.36; N, 9.31. Found: C, 68.76; H, 7.47; N, 9.09.

EXAMPLE 29

3'-O-[(N,N-Diisopropylamino) (β-cyanoethoxy) phosphanyl]-5'-O-(4,4'-dimethoxytrityl)-N₂-isobutyryl-N₂-nonyl-9-(2-deoxy-β-D-erythro-pentofuranosyl)guanosine. (30)

A well dried solution of 29 (1.7 g, 2.22 mmol) in dry dichloromethane (30 mL) was cooled to 0° C. To this cold solution was added N,N-diisopropyethylamine (0.57 g, 4.4 mmol) and (β-cyanoethoxy)chloro(N,N-diisopropylamino) phosphane (0.94 g, 4.0 mmol) under argon atmosphere. The reaction mixture was stirred at room temperature for 2 hours and diluted with $CH_2Cl_2$ (170 mL). The organic extract was washed with 5% $NaHCO_3$ (25 mL), water (25 mL) and brine (25 mL), dried over $Na_2SO_4$, and evaporated to dryness. The residue was purified on a silica column using $CH_2Cl_2$/acetone (9:1) containing 1% triethylamine as eluent. The pure fractions were pooled together and evaporated to dryness to give 1.5 g (53%) of 30.

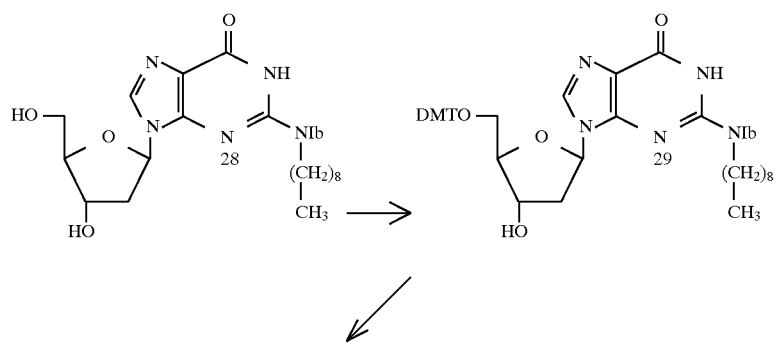

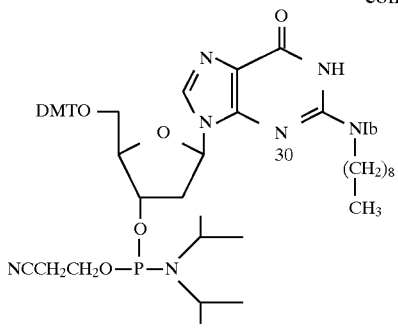

EXAMPLE 30

3',5'-O-(Tetraisopropyldisiloxane-1,3-diyl)-2-chloro-9-(2-deoxy-β-D-erythro-pentofuranosyl) adenosine. (31)

Compound 31 was prepared from compound 10 by following the procedure used for the preparation of 12. Starting materials used: 10 (4.30 g, 15.09 mmol), 1,3-dichloro-1,1,3,3-tetraisopropyldisiloxane (4.74 g, 15.1 mmol), dry TEA (3.05 g, 30.2 mmol), and dry pyridine (100 mL). The crude product was purified by flash chromatography using $CH_2Cl_2$/acetone (7:3) as eluent to give 7.3 g (92%) of 31. The pure product was crystallized from ethylacetate/hexane as a colorless solid. mp 183°–185° C.: $^1$H NMR ($Me_2SO$-$d_6$) δ1.00 (m, 28H), 2.54 (m, 1H, $C_2$H), 2.82 (m, 1H, $C_2$H), 3.76 (m, 1H, $C_4$H), 3.86 (m, 2H, $C_5$·$CH_2$), 5.08 (m, 1H, $C_3$H), 6.22 (t, 1H, $J_{1',2'}$=6.20 Hz, $C_1$·H), 7.82 (b s, 2H, $NH_2$), 8.22 (s, 1H, $C_8$H). Anal. Calcd for $C_{22}H_{38}ClN_5O_4Si_2$: C, 50.02; H, 7.25; N, 13.26, Cl, 6.72. Found: C, 50.24; H, 7.28; N, 13.07, Cl, 6.63.

EXAMPLE 31

3',5'-O-(Tetraisopropyldisiloxane-1,3-diyl)-2-chloro-$N_6$-benzoyl-9-(2-deoxy-β-D-erythro-pentofuranosyl) adenosine. (32)

A well dried solution of 31 (8 g, 15.00 mmol) in dry pyridine (150 mL) was allowed to react with triethylamine (4.55 g, 45.00 mmol) and benzoyl chloride (6.3 g, 45.00 mmol) at room temperature for 12 hours under an atmosphere of argon. The reaction mixture was evaporated to dryness. The residue was partitioned between $CH_2Cl_2$/water and extracted in $CH_2Cl_2$ (2×150 mL). The organic extract was washed with brine (60 mL), dried over $MgSO_4$ and evaporated to dryness. The residue was purified by silica column using $CH_2Cl_2$/acetone as eluent and crystallization from the same solvent gave 8.2 g (86%) of 32. mp 167°–170° C.: $^1$H NMR ($Me_2SO$-$d_6$) δ1.00 (m, 28H), 2.60 (m, 1H, $C_2$·H), 3.02 (m, 1H, $C_2$·H), 3.84 (m, 3H, $C_5$·$CH_2$ and $C_4$·H), 5.04 (m, 1H, $C_3$·H), 6.34 (d, 1H, $C_1$·H), 7.42–7.84 (m, 5H, ArH), 8.70 (s, 1H, $C_8$H). Anal. Calcd for $C_{29}H_{42}ClN_5O_5Si_2$: C, 55.08; H, 6.69; N, 11.08, Cl, 5.61. Found: C, 55.21; H, 6.79; N, 11.19, Cl, 5.70.

EXAMPLE 32

$N_6$-Benzoyl-2-chloro-9-(2-deoxy-β-D-erythro-pentofuranosyl)adenosine. (33)

To a stirred solution of 32 (7.9 g, 12.5 mmol) in dry THF (100 mL) was added 1M solution of tetrabutylammonium fluoride (50 mL, 50.00 mmol) slowly over a 15 minute period at room temperature. The reaction mixture was stirred for 6 hours and evaporated to dryness. The residue was purified by flash chromatography using $CH_2Cl_2$/acetone (7:3) as eluent to give 3.88 g (80%) of 33. mp>275° C. dec: $^1$H NMR ($Me_2SO$-$d_6$) δ2.34 (m, 1H, $C_2$·H), 2.72 (m, 1H, $C_2$·H), 3.58 (m, 2H, $C_5$·$CH_2$), 3.88 (m, 1H, $C_4$·H), 4.42 (m, 1H, $C_3$·H), 4.96 (t, 1H, $C_5$·OH), 5.38 (d, 1H, $C_3$·OH), 6.40 (t, 1H, $J_{1',2'}$=6.20 Hz, $C_1$·H), 7.52 (m, 2H, ArH), 7.64 (m, 1H, ArH), 8.04 (d, 2H, ArH), 8.70 (s, 1H, $C_8$H), 11.52 (b s, 1H, NH). Anal. Calcd for $C_{17}H_{16}ClN_5O_4$: C, 52.37; H, 4.14; N, 17.97; Cl, 9.11. Found: C, 52.31; H, 4.07; N, 17.94; Cl, 9.03.

EXAMPLE 33

5'-O-(4,4'-Dimethoxytrityl)-$N_6$-benzoyl-2-chloro-9-(2-deoxy-β-D-erythro-pentofuranosyl) adenosine. (34)

The compound was prepared from 33 by following the procedure used for the preparation of 8. Starting materials used: 33 (2.5 g. 6.43 mmol), 4,4'-dimethoxytrityl chloride (2.37 g, 7.0 mmol), dry TEA (0.71 g, 7.0 mmol) and dry pyridine (100 mL). The crude product was purified by flash chromatography using $CH_2Cl_2$/EtOAc (7:3) containing 1% triethylamine as the eluent to give 3 g (68%) of 34 as foam: $^1$H NMR ($Me_2SO$-$d_6$) δ2.34 (m, 1H, $C_2$·H), 2.82 (m, 1H, $C_2$·H) 3.18 (m, 2H, $C_5$·$CH_2$), 3.64 (2d, 6H, $OCH_3$), 3.98 (m, 1H, $C_4$·H), 4.44 (m, 1H, $C_3$·H), 5.40 (d, 1H, OH), 6.42 (t, 1H, $J_{1',2'}$=6.20 Hz, $C_1$·H), 6.74 (m, 4H, ArH), 7.16 (m, 7H, ArH), 7.32 (m, 2H, ArH), 7.52 (m, 7H, ArH), 7.64 (m, 1H, ArH), 8.04 (m, 2H, ArH), 8.58 (s, 1H, $C_8$H), 11.50 (b s, 1H, NH). Anal. Calcd for $C_{38}H_{34}ClN_5O_6$: C, 65.93; H, 4.95; N, 10.12; Cl, 5.13. Found: C, 65.55; H, 5.16; N, 9.73; Cl, 5.10.

EXAMPLE 34

3'-O-[(N,N-Diisopropylamino) (β-cyanoethoxy) phosphanyl]-5'-O-(4,4'-dimethoxytrityl)-$N_6$-benzoyl-2-chloro-9-(2-deoxy-β-D-erythro-pentofuranosyl) adenosine. (35)

The title compound was prepared from 34 by following the procedure used for the preparation of 9. Starting materials used: Compound 34 (2.4 g, 3.47 mmol), N, N-diisopropylethylamine (1.22 mL, 7.00 mmol), (β-cyanoethoxy) chloro(N,N-diisopropylamino)phosphene (1.65 g, 7.00 mmol) and dry $CH_2Cl_2$ (30 mL). The crude product was purified by flash chromatography using hexane-ethyl acetate (1:1) containing 1% triethylamine as eluent.

The pure fractions were pooled together and evaporated to dryness to give 1.8 g (58%) of 35. The foam was dissolved in dry dichloromethane (10 mL) and added dropwise into a well stirred hexane (1500 mL) under argon atmosphere. After the addition, stirring was continued for an additional 1 hour and the precipitated solid was filtered, washed with hexane and dried over solid NaOH for 3 hours. The dried powder showed no traces of impurity in $^{31}P$ spectrum: $^1H$ NMR (Me$_2$SO-d$_6$) δ1.18 (m, 12H, Isobutyryl CH$_3$), 2.58 (m, 3H, C$_{2'}$H and Isobutyryl CH), 2.98 (m, 1H, C$_{2'}$H), 3.34 (d, 2H, CH$_2$), 3.64 (m, 2H, C$_{5'}$CH$_2$), 3.72 (m, 8H, 2 OCH$_3$ and CH$_2$), 4.24 (m, 1H, C$_{4'}$H), 4.82 (m, 1H, C$_{3'}$H), 6.36 (t, 1H, J$_{1',2'}$=6.20 Hz, C$_{1'}$H), 6.76 (m, 4H, ArH), 7.22 (m, 7H, ArH), 7.38 (m, 2H, ArH), 7.52 (m, 2H, ArH), 7.64 (m, 1H, ArH), 7.98 (m, 2H, ArH), 8.24 (s, 1H, C8H), 9.34 (b s, 1H, NH).

filtrate evaporated to dryness. The product 5.26 g (100%) was found to be moisture sensitive and remains as viscous oil. The oil was used as such for further reaction without purification.

The above foam (5.26 g, 18.4 mmol) was coevaporated with dry pyridine (3×100 mL). The dried residue was dissolved in dry DMF/Py (75:50 mL) and cooled to 0° C. in an ice bath under argon atmosphere. To this cold stirred solution was added triethylamine (3.72 g, 36.8 mmol) followed by 1,3-dichloro-1,1,3,3-tetraisopropyldisiloxane (TipSiCl, 5.79 g, 18.4 mmol) during 15 min period. After the addition of TipSiCl, the reaction mixture was allowed to stir at room temperature for 12 hr. The solution was evaporated to dryness and dissolved in dicholoromethane (200 mL). The CH$_2$Cl$_2$ layer was washed with 5% NaHCO$_3$ (50 mL), water

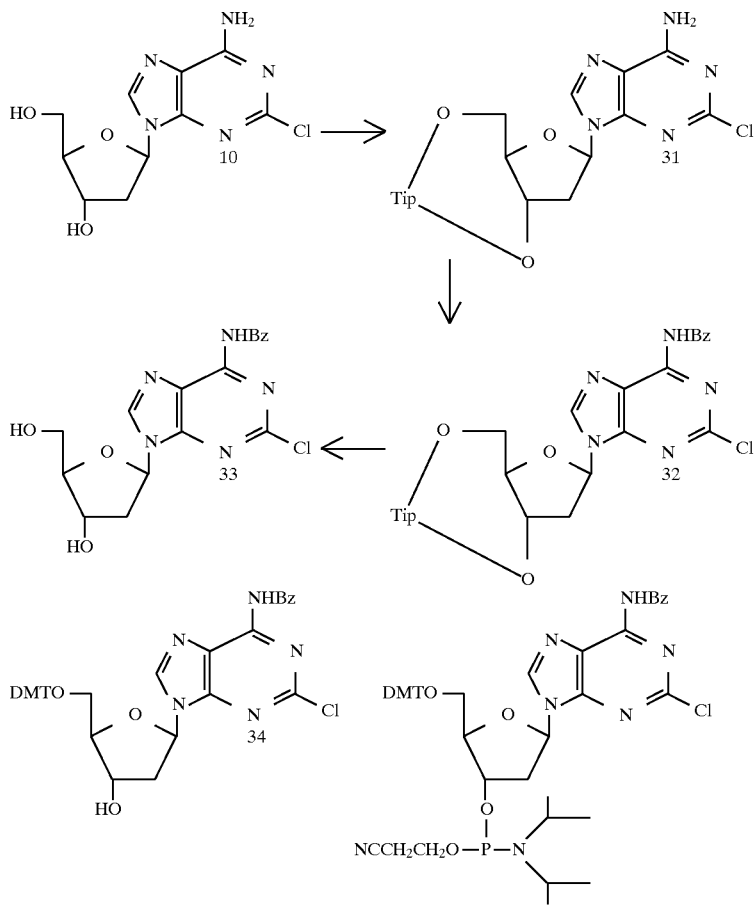

EXAMPLE 35

3',5'-O-(Tetraisopropyldisiloxane-1,3-diyl)-2-chloro-9-(2-deoxy-β-D-erythro-pentofuranosyl) inosine. (36)

2-Chloro-6-allyloxy-9-(2-deoxy-β-D-erythro-pentofuranosyl)purine (2, 6 g, 18.4 mmol), Pd/C (10%, 1 g) and triethylamine (1.92 g, 19.00 mmol) in ethyl alcohol (200 ml) was hydrogenated at atmospheric pressure during a 30 min period at room temperature. The reaction was followed by the absorption of volume of hydrogen. The reaction mixture was filtered, washed with methanol (50 mL) and the (50 mL) and brine (30 mL). The organic extract was dried and evaporated to dryness. The residue was purified by flash chromatography over silica gel column using CH$_2$Cl$_2$→MeOH as the eluent. The pure fractions were pooled together and evaporated to give 7.59 g (78%) of the titled compound as foam. $^1H$ NMR (Me$_2$SO-d$_6$) δ1.00 (m, 28H), 2.62 (m, 1H, C$_{2'}$H), 2.80 (m, 1H, C$_{2'}$H), 3.90 (m, 3H, C$_{5'}$CH$_2$, C$_{4'}$H), 5.00 (m, 1H, C$_{3'}$H), 6.24 (t, 1H, J$_{1',2'}$=6.20 Hz, C$_{1'}$H), 8.18 (s, 1H, C$_8$H). Anal. Calcd for C$_{22}$H$_{37}$ClN$_4$O$_5$Si$_2$. C, 49.93; H, 7.05; N. 10.58. Found: C, 49.92; H, 6.80; N, 10.70.

EXAMPLE 36

3',5'-O-(Tetraisopropyldisiloxane-1,3-diyl)-$N_2$-ethyl-9-(2-deoxy-β-D-erythro-pentofuranosyl) guanosine. (37)

A solution of 3',5'-O-(tetraisopropyldisiloxane-1,3-diyl)-2-chloro-9-(2-deoxy-β-D-erythro-pentofuranosyl)-inosine (36, 5.0 g, 9.45 mmol) in 2-methoxyethanol (30 mL) was placed in a steel bomb and cooled to 0° C. Freshly condensed ethylamine (7.0 mL) was quickly added. The steel bomb was sealed and the reaction mixture was stirred at 90° C. for 16 hours. The vessel was cooled and opened carefully. The precipitated white solid was filtered and crystallized from methanol. The filtrate on evaporation gave solid which was also crystallized from methanol. Total yield 3. g (65%). mp>250° C. dec: $^1$H NMR (Me$_2$SO-d$_6$) δ1.06 (m, 31H), 2.32 (m, 1H, $C_2$H), 2.84 (m, 1H, $C_2$H), 3.26 (m, 2H, $CH_2$), 4.12 (m, 2H, $C_5$CH$_2$), 4.22 (m, 1H, $C_4$H), 4.70 (m, 1H, $C_3$H), 6.23 (t, 1H, $J_{1',2'}$=6.20 Hz, $C_1$H), 6.42 (m, 1H, NH), 7.87 (s, 1H, $C_8$H), 10.58 (b s, 1H, NH). Anal. Calcd for $C_{24}H_{43}N_5O_5Si_2$. C, 53.59; H, 8.06; N, 13.02. Found: C, 53.44; H, 8.24; N, 12.91.

EXAMPLE 37

3',5'-O-(Tetraisopropyldisiloxane-1,3-diyl)-6-O-diphenylcarbamoyl-$N_2$-ethyl-9-(2-deoxy-β-D-erythro-pentofuranosyl)guanosine. (38)

Compound 37 (2.40 g, 4.46 mmol) was dissolved in anhydrous pyridine (30 mL) at room temperature. To this solution was added N,N-diisoproylethylamine (1.60 mL, 8.93 mmol) followed by diphenylcarbamoyl chloride (2.07 g, 8.93 mmol). The mixture was stirred at room temperature under an atmosphere of argon for 10 hours. A dark red solution was obtained, which was evaporated to dryness. The residue was purified by flash chromatography on a silica column using $CH_2Cl_2$/EtoAc as eluent. The pure fractions were collected together and evaporated to give 3.24 g (99%) of 38 as a brownish foam. $^1$H NMR (Me$_2$SO-d$_6$) δ1.14 (t, 31H), 2.52 (m, 1H, $C_2$H), 3.04 (m, 1H, $C_2$H), 3.34 (m, 2H, $CH_2$), 3.87 (m, 3H, $C_5$CH$_2$ & $C_4$H), 4.83 (m, 1H, $C_3$H), 6.23 (m, 1H, $C_1$H), 7.36 (m, 11H, ArH & NH), 8.17 (s, 1H, $C_8$H). Anal. Calcd for $C_{37}H_{52}N_6O_6Si_2$. C, 60.71; H. 7.16; N, 11.48. Found: C, 60.33; H, 7.18; N, 11.21.

EXAMPLE 38

6-O-Diphenylcarbamoyl-$N_2$-ethyl-9-(2-deoxy-β-D-erythro-pentofuranosyl)guanosine. (39)

To a stirred solution of 38 (3.25 g, 4.47 mmol) in pyridine (25 mL) was added a 0.5M solution of tetrabutylammonium fluoride (prepared in pyridine/THF/water, 4/1/1,36 mL, 17.88 mmol) all at once. The reaction was allowed to stir for 10 minutes and quenched with H$^+$ resin (amberlite IRC 50) to pH 7. The resin was filtered and washed with pyridine (20 mL) and MeOH (20 mL). The filtrate was evaporated to dryness. The residue was purified using flash chromatography over a silica column using methylene chloride-acetone as eluent to give 1.84 g (84%) of the pure product as a foam. $^1$H NMR (Me$_2$SO-d$_6$) δ1.14 (t, 3H, $CH_2CH_3$), 2.22 (m, 1H, $C_2$H), 2.76 (m, 1H, $C_2$H), 3.34 (m, 2H, $CH_2$), 3.57 (m, 2H, $C_5$CH$_2$), 3.84 (m, 1H, $C_4$H), 4.42 (m, 1H, $C_3$H), 4.91 (t, 1H, $C_5$OH), 5.32 (d, 1H, $C_3$OH), 6.27 (t, 1H, $J_{1',2'}$=6.20 Hz $C_1$H), 7.29 (m, 1H, NH), 7.46 (m, 10H, ArH), 8.27 (s, 1H, $C_8$H). Anal. Calcd for $C_{25}H_{26}N_6O_5$·¾$H_2O$. C, 59.61; H, 5.35; N, 16.68. Found: C, 59.83; H, 5.48; N, 16.21.

EXAMPLE 39

$N_2$-Ethyl-9-(2-deoxy-β-D-erythro-pentofuranosyl) guanosine. (40)

The intermediate of 39 (0.25 g, 0.51 mmol) was stirred in methanolic/ammonia (saturated at 0° C.) in a steel bomb at room temperature for 40 hours. The vessel was cooled to 0° C., opened carefully, and the solvent evaporated to dryness. The solid obtained was crystallized from methanol to give a white powder (0.95 g, 63%): mp 234°–238° C. $^1$H NMR (Me$_2$SO-d$_6$) δ1.14 (t, 3H, $CH_2CH_3$), 2.18 (m, 1H, $C_2$H), 2.67 (m, 1H, $C_2$H), 3.34 (m, 2H, $CH_2$), 3.52 (m, 2H, $C_5$CH$_2$), 3.82 (m, 1H, $C_4$H), 4.36 (m, 1H, $C_3$H), 4.89 (t, 1H, $C_5$OH), 5.30 (d, 1H, $C_3$OH), 6.16 (t, 1H, $J_{1',2'}$=6.20 Hz $C_1$H), 6.44 (m, 1H, NH), 7.91 (s, 1H, $C_8$H), 10.58 (b s, 1H, NH).

EXAMPLE 40

5'-O-(4,4'-Dimethoxytrityl)-6-O-diphenylcarbamoyl-$N_2$-ethyl-9-(2-deoxy-β-D-erythro-pentofuranosyl) guanosine. (41)

Compound 39 (1.6 g, 3.26 mmol) was dried well by coevaporation with dry pyridine (3×50 mL). The dried material was dissolved in anhydrous pyridine (25 mL) and allowed to stir under argon atmosphere. To this stirred solution was added triethylamine (0.59 mL, 4.24 mmol) followed by DMTCl (1.44 g, 4.24 mmol). The reaction mixture was stirred at room temperature for 14 hours and quenched with methanol (10 mL). After stirring for 15 minutes, the solvent was removed and the residue was dissolved in methylene chloride (150 mL). The organic extract was washed with saturated NaHCO$_3$ solution (30 mL), water (30 mL), and brine (30 mL). The methylene chloride extract was dried and evaporated to dryness. The residue was purified by flash chromatography over silica gel using methylene chloride/acetone as eluent. The pure fractions were collected together and evaporated to give a foam (2.24 g, 87%). $^1$H NMR (Me$_2$SO-d$_6$) δ1.10 (t, 3H, $CH_2CH_3$), 2.32 (m, 1H, $C_2$H), 2.82 (m, 1H, $C_2$H), 3.15 (m, 2H, $CH_2$), 3.34 (s, 6H, 2 OCH$_3$), 3.67 (m, 2H, $C_5$CH$_2$), 3.96 (m, 1H, $C_4$H), 4.42 (m, 1H, $C_3$H), 5.36 (d, 1H, $C_3$OH), 6.30 (t, 1H, $J_{1',2'}$=6.20 Hz, $C_1$H), 6.83 (m, 4H, ArH), 7.23 (m, 10H, ArH & NH), 8.17 (s, 1H, $C_8$H). Anal Calcd for $C_{45}H_{44}N_6O_7$. ¼ $CH_3OH$. ¼ $H_2O$. C, 68.50; H, 5.78; N, 10.60. Found: C, 68.72; H, 5.42; N, 10.40.

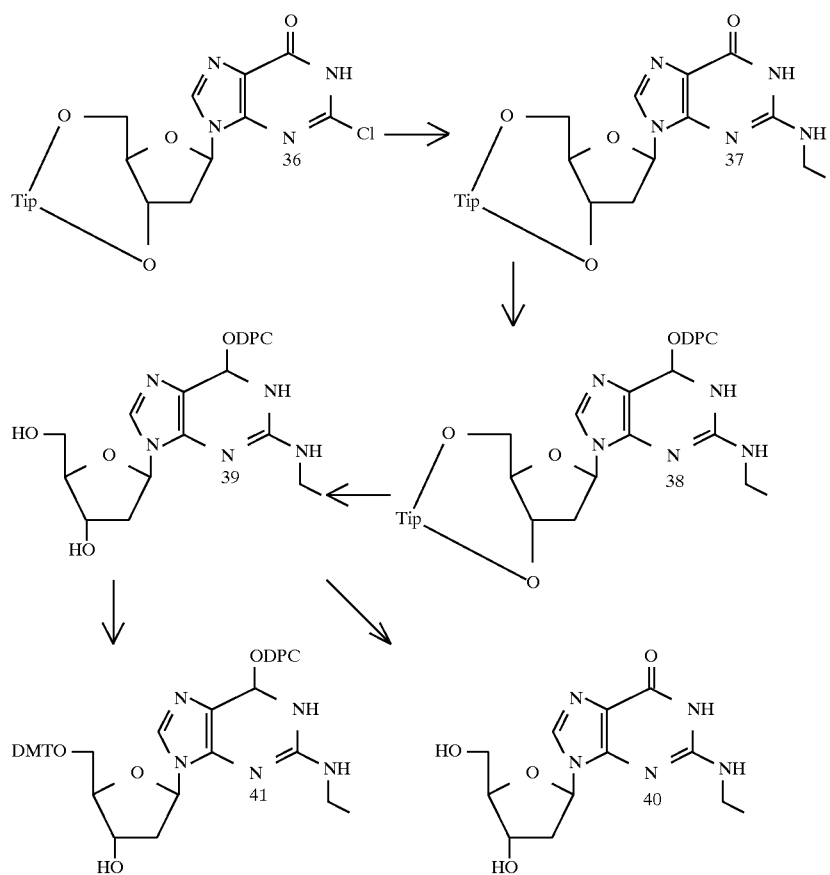

EXAMPLE 41

3'-O-[(N,N-Diisopropylamino) (β-cyanoethoxy) phosphanyl]-5'-O-(4,4'-dimethoxytrityl)-6-O-diphenylcarbamoyl-N₂-ethyl-9-(2-deoxy-β-D-erythro-pentofuranosyl)guanosine. (42)

The DMT derivative of 40 was dried well overnight at vacuum and dissolved in dry methylene chloride (25 mL). The solution was cooled to 0° C. under argon atmosphere. To this cold stirring solution N,N-diisopropylamine tetrazolide salt (0.24 g, 1.41 mmol) followed by phosphorylating reagent (1.71 mL, 5.66 mmol) were added. The mixture was stirred at room temperature for 12 hours under argon. The solution was diluted with additional methylene chloride (100 mL) and washed with saturated NaHCO₃ solution (50 mL), water (50 mL), and brine (50 mL). The organic extract was dried and evaporated to dryness. The crude product was purified by flash column over silica gel using methylene chloride/ethyl acetate containing 1% triethylamine as eluent. The pure fractions were pooled and evaporated to give 2.5 g (91%) of 42.

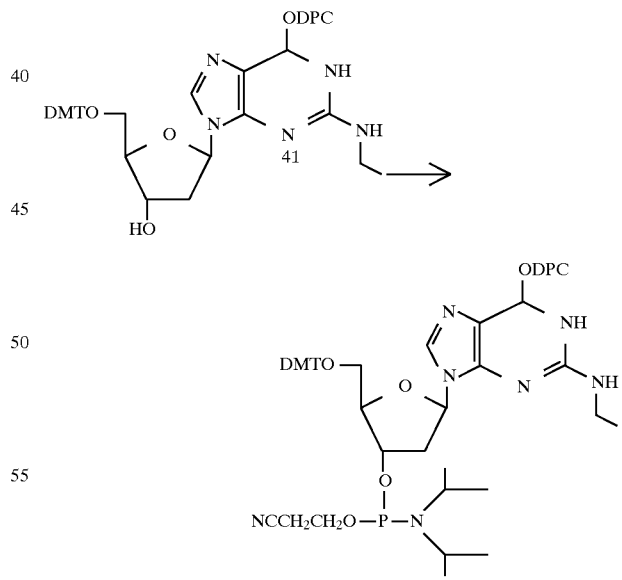

EXAMPLE 42

2-Amino-6-chloro-9-(2-deoxy-3,5-di-O-p-toluoyl-β-D-erythropentofuranosyl)purine. (43)

To a stirred suspension of 2-amino-6-chloropurine (1, 10.0 g, 60.01 mmol) in dry acetonitrile (1000 mL) was added sodium hydride (60% in oil, 2.50 g, 62.50 mmol) in small portions over a period of 30 minutes under argon atmosphere. The mixture was heated to reflux for 30 minutes. After allowing the solution to cool to room temperature, powdered and dry 1-chloro-2-deoxy-3,5-di-O-p-toluoyl-α-D-erythro-pentofuranose (25.0 g, 68.75 mmol) was quickly added and the stirring was continued for 10 h at room temperature under argon atmosphere. The reaction mixture was evaporated to dryness and the residue dissolved in a mixture of $CH_2Cl_2/H_2O$ (250:100 mL) and extracted in dichloromethane. The organic layer was washed with brine (100 mL), dried and evaporated to dryness. The residue on purification by flash chromatography over silica gel using $CH_2Cl_2 \rightarrow$ethyl acetate as the eluent afforded 43 in 77% yield. A small amount of solid was crystallized from ethanol for analytical purpose: mp 173°–175° C.; $^1H$ NMR (DMSO-$d_6$): δ2.37 (s, 3H, $CH_3$), 2.38 (s, 3H, $CH_3$), 2.7 (m, 1H, $C_2·H$), 3.22 (m, 1H, $C_2·H$), 4.59 (m, 3H, $C_5·CH_2$ and $C_4·H$), 5.75 (d, 1H, $C_3·H$), 6.32 (t, 1H, $C_1·H$), 7.00 (s, 2H, $NH_2$), 7.30 (dd, 4H, phenyl), 7.82 (dd, 4H, phenyl), and 8.32 (s, 1H, $C_8H$).

EXAMPLE 43

2-Amino-6-Chloro-9-(2-deoxy-β-D-erythro-pentofuranosyl)purine. (44)

To a solution of 43 (14.0 g, 28.35 mmol) in methylene chloride (50 mL) was added $CH_3OH/NH_3$ (750 mL) at room temperature. The reaction mixture was allowed to stir at room temperature in a steel bomb for 12 h. The steel bomb was cooled to 0° C., opened carefully and evaporated to dryness. The residue was dissolved in methanol (50 mL), adsorbed on silica gel (20 g), and evaporated to dryness. The dried silica gel was placed on top of silica column (250–400 mesh, 10×30 cm) packed in $CH_2Cl_2$. The column was eluted with $CH_2Cl_2/CH_3OH$. The fractions having the product were pooled together and evaporated to dryness to afford 44 as colorless solid 7.13 g (88%). $^1H$ NMR (DMSO-$d_6$): δ2.26 (m, 1H, $C_2·H$), 2.60 (m, 1H, $C_2·H$), 3.50 (s, 2H, $C_5·CH_2$), 3.80 (m, 1H, $C_4·H$), 4.38 (bs, 1H, $C_3·H$), 4.93 (t, 1H, $C_5·OH$), 5.25 (d, 1H, $C_3·OH$), 6.20 (t, 1H, $C_1·H$), 6.90 (s, 2H, $NH_2$), 8.32 (s, 1H, $C_8H$).

EXAMPLE 44

3',5'-O-(Tetraisopropyldisiloxane-1,3-diyl)-2-amino-6-chloro-9-(2-deoxy-β-D-erythro-pentofuranosyl)purine. (45)

2-Amino-6-chloro-9-(2-deoxy-β-D-erythro-pentofuranosyl)purine (44, 5.35 g, 18.72 mmol) was dissolved in dry pyridine (100 mL), and evaporated to dryness keeping the temperature below 35° C. This was repeated for three times to remove traces of water. The dried substrate 44 was dissolved in dry DMF (150 mL) and allowed to stir at room temperature under an atmosphere of argon. To this stirred solution was added dry triethylamine (5.24 mL, 37.44 mmol). The solution was cooled to 0° C. in an ice bath. 1,3-Dichloro-1,1,3,3-tetraisopropyldisiloxane (TipSiCl, 7.37 mL, 23.4 mmol) was added during a 30 minute period. After the addition of TipSiCl, the reaction mixture was allowed to stir at room temperature overnight. The solvent was stripped off under reduced pressure to dryness. The residue obtained was dissolved in methylene chloride (250 mL) and washed with 5% $NaHCO_3$ solution (50 mL), water (35 mL) and brine (30 mL). The extract was dried over anhydrous $Na_2SO_4$ and evaporated to dryness. The residue on purification by flash chromatography over silica gel using $CH_2Cl_2/MeOH$ gave 9.5 g (90%) of 45 as a foam: $^1H$ NMR ($Me_2SO$-$d_6$) δ0.96 (m, 28H), 2.45 (m, 1H, $C_2·H$), 2.74 (m, 1H, $C_2·H$), 3.72 (m, 1H, $C_4·H$), 3.84 (m, 2H, $C_5·CH_2$), 4.64 (q, 1H, $C_3·H$), 6.14 (m 1H, $C_1·H$), 6.85 (s, 2H, $NH_2$), 8.18 (s, 1H, $C_8H$). Anal. Calcd for $C_{22}H_{38}ClN_5O_4Si_2$ (528.20): C, 50.03; H, 7.25; N,.13.26. Found: C, 50.39; H, 7.39; N, 12.37.

EXAMPLE 45

3',5'-O-(Tetraisopropyldisiloxane-1,3-diyl)-$N_2$-isobutyryl-2-amino-6-chloro-9-(2-deoxy-β-D-erythro-pentofuranosyl)purine. (46)

To a well dried stirred solution of the substrate 45 (2.0 g, 3.54 mmol) [co-evaporated three times with dry pyridine (3×50 mL)] in dry pyridine (50 mL) at 0° C. was added dropwise a solution of isobutyryl chloride (446 μL, 4.16 mmol) in dry pyridine (10 mL) optionally containing one equivalent of triethylamine during a period of 2 h. After the addition of IbCl, the reaction mixture was allowed to stir for an additional 1 hour and quenched with $CH_3OH$ (10 mL). The solvent was removed to give a brown syrup. The crude material was dissolved in $CH_2Cl_2$ (150 mL) and washed with 5% $NaHCO_3$ (20 mL), water (20 mL), and brine (20 mL). The organic extract was dried over anhydrous $Na_2SO_4$, filtered and evaporated to dryness. The residue was purified by flash chromatography over silica gel using $CH_2Cl_2 \rightarrow$acetone as the eluent. The pure fractions were collected together and evaporated to give 1.67 g (74%) of 46 as a foam: $^1H$ NMR (DMSO-$d_6$): δ1.00 (m, 34H), 2.55 (m, 1H, $C_2·H$), 2.75 (m, 1H, isobutyryl methine), 2.96 (m, 1H, $C_2·H$), 3.85 (m, 2H, $C_5·CH_2$), 4.07 (m, 1H, $C_4·H$), 5.13 (q, 1H, $C_3·H$), 6.32 (dd 1H, $C_1·H$), 8.56 (s, 1H, $C_8H$), 10.86 (s, 1H, NH). Anal. Calcd for $C_{26}H_{44}ClN_5O_5Si_2$ (598.30): C, 52.20; H, 7.41; N, 11.70. Found: C, 52.07; H, 7.44; N, 11.35.

EXAMPLE 46

$N_2$-Isobutyryl-2-amino-6-chloro-9-(2-deoxy-β-D-erythro-pentofuranosyl)purine. (47)

To a stirred solution of the protected derivative 46 (6.29 g, 9.93 mmol) in pyridine (30 mL) was added 0.5M solution (20 mL, 10 mmol) of tetrabutylammonium fluoride [prepared in a mixture of tetrahydrofuran-pyridine-water (8:1:1, v/v/v; 20 mL)] at room temperature. The reaction mixture was stirred for 10 min and quenched with $H^+$resin (pyridinium form) to pH 6-7. The resin was filtered off, washed with pyridine (50 mL) and methanol (50 mL). The combined filtrate was evaporated to dryness at vacuum keeping e bath temperature below 35° C. The residue was dissolved in methylene chloride (50 mL) and loaded on top of a silica gel column packed in methylene chloride. The column was eluted with a gradient of $CH_2Cl_2 \rightarrow$—MeOH. The pure fractions were pooled and evaporated to give 7.7 g (93%) of 47 as yellowish foam: $^1H$ NMR ($Me_2SO$-$d_6$) δ1.13 (2 s, 6H, isobutyryl $CH_3$), 2.25 (m, 1H, $C_2·H$), 2.75 (m, 2H, isobutyryl methine & $C_2·H$), 3.55 (m, 2H, $C_5·CH_2$), 3.85 (m, 1H, $C_4·H$), 4.42 (q, 1H, $C_3·H$), 4.90 (t, 1H, $C_5·OH$), 5.35 (d, 1H, $C_3·OH$), 6.34 (t 1H, $C_1·H$), 8.70 (s, 1H, $C_8H$), 10.82 (s, 1H, NH). Anal. Calcd for $C_{14}H_{18}ClN_5O_4\cdot CH3OH$ (387.86): C, 46.45; H, 5.71; N, 18.06. Found: C, 46.68; H, 5.29; N, 18.10.

EXAMPLE 47

5'-O-(4,4-Dimethoxytrityl)-N$_2$-isobutyryl-2-amino-6-chloro-9-(2-deoxy-β-D-erythro-pentofuranosyl)purine. (48)

The substrate 47 was dried overnight under high vacuum in the presence of NaOH pellets. The dried 47 was coevaporated three times with dry pyridine (75 mL). To this dried solution of 47 (7.41 g, 20.83 mmol) in dry pyridine (100 mL) was added triethylamine (2.90 mL, 20.83 mmol) followed by 4,4'-dimethoxytrityl chloride (9.17 g, 27.08 mmol). The reaction mixture was stirred at room temperature under an atmosphere of argon for 15 hours. The reaction was quenched with methanol (10 mL) and the solvent removed under reduced pressure. The residue was dissolved in methylene chloride (250 mL) and washed with 5% NaHCO$_3$ solution (50 mL), water (40 mL), and brine (40 mL). The organic extract was dried over anhydrous Na$_2$SO$_4$ and the solvent removed to give a dark oil. The crude product was purified by flash column over silica gel using CH$_2$Cl$_2$→acetone as eluent. The fractions having the pure product was collected together and evaporated to give 48 (12.7 g, 93%) as an orange foam: $^1$H NMR (DMSO-d$_6$): δ1.07 (2 s, 6H, isobutyryl CH$_3$), 2.38 (m, 1H, C$_2$·H), 2.77 (m, 1H, C$_2$·H), 2.84 (m, 1H, isobutyryl methine), 3.72 (s, 6H, 2×OCH$_3$), 4.00 (m, 3H, C$_5$·CH$_2$ & C$_4$·H), 4.62 (m, 1H, C$_3$·H), 5.32 (d, 1H, C$_3$·OH), 6.39 (t 1H, C$_1$·H), 6.72 (m, 4H, phenyl), 7.13 (m, 9H, phenyl), 8.62 (s, 1H, C$_8$H), 10.79 (s, 1H, NH). Anal. Calcd. for C$_{35}$H$_{36}$ClN$_5$O$_6$(658.18): C, 63.87; H, 5.51; N, 10.64. Found: C, 63.68; H, 5.85; N, 10.67.

EXAMPLE 48

3'-O-[(N,N-diisopropylamino) (β-cyanoethoxy) phosphanyl]-5'-O-(4,4'-dimethoxytrityl)-N$_2$-isobutyryl-2-amino-6-chloro-9-(2-deoxy-β-D-erythro-pentofuranosyl)purine. (49)

The dried (dried over solid NaOH under vacuum overnight) substrate 48 (5.36 g, 8.15 mmol) was dissolved in dry methylene chloride (80 mL) and cooled to 0° C. under an atmosphere of argon. To this cold stirred solution was added N,N-diisopropylethylamine (2.84 mL, 16.30 mmol) and stirred for 10 min. (β-cyanoethoxy)-chloro(N,N-diisopropylamino)phosphane (3.86 mL, 16.30 mmol) was added dropwise over a period of 15 min. After the addition was over, the reaction mixture was stirred at room temperature for 2 hours and diluted with methylene chloride (100 mL). The methylene chloride extract was washed with sat.NaHCO$_3$ (50 mL) and brine (50 mL). The organic extract was dried over anhydrous Na$_2$SO$_4$ and the solvent was removed under reduced pressure. The residue was purified by flash chromatography over silica gel using methylene chloride/acetone containing 1% triethylamine as the eluent. The main fractions were collected and evaporated to give 6.64 g (95%) of 49. The foam was dissolved in dry methylene chloride (10 mL) and added dropwise into a stirred solution of hexane under argon atmosphere during an hour period. The precipitated solid was filtered, washed with dry hexane and dried over high vacuum in the presence of solid NaOH. Yield 5.42 g (78%).

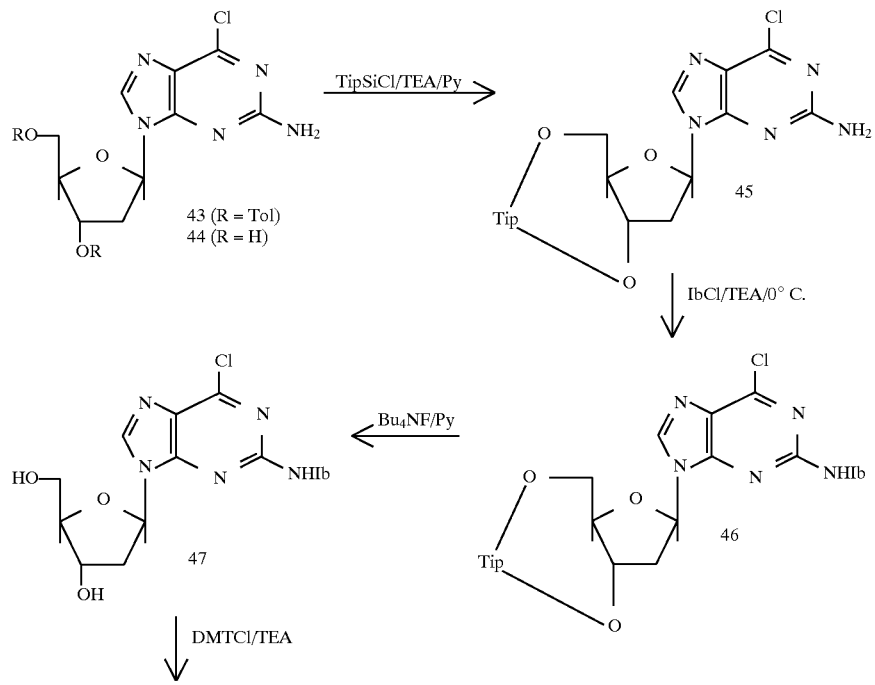

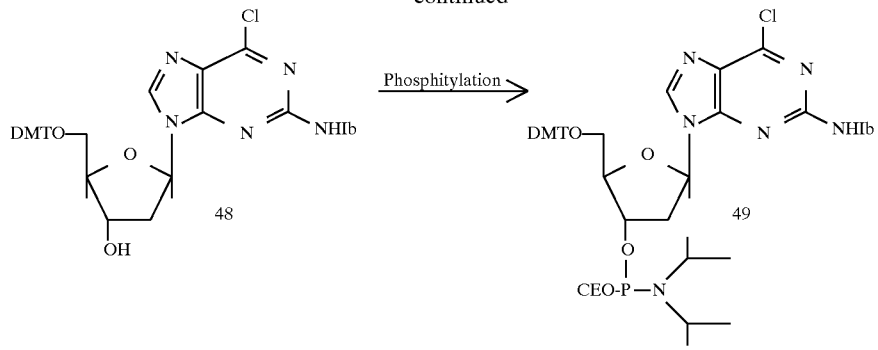

EXAMPLE 49

2-Amino-N$_6$-[imidazol-1-yl(propyl)]-9-(2-deoxy-β-D-erythro-pentofuranosyl)adenosine. (50)

A mixture of 44 (5.0 g, 17.5 mmol), 1-(3-aminopropyl) imidazole (2.5 mL, 21.0 mmol) and TEA (3.0 mL, 21.0 mmol) in 2-methoxy ethanol (60 mL) was heated at 75° C. in a steel bomb for 18 hours. The steel bomb was cooled to 0° C., opened and the solution evaporated to dryness. The resulting oil was purified by flash chromatography using CH$_2$Cl$_2$→CH$_3$OH as the eluent. The pure fractions were combined and evaporated to give 50 as a foam (5.24 g, 87%). $^1$H NMR (DMSO-d$_6$): δ2.00 (m, 2H, CH$_2$), 2.16 (m, 1H, C$_2$·H), 2.56 (m, 1H, C$_2$·H), 3.39 (m, 2H, CH$_2$), 3.50 (s, 2H, C$_5$·CH$_2$), 3.81 (m, 1H, C$_4$·H), 3.98 (m, 4H, CH$_2$), 4.33 (m, 1H, C$_3$·H), 5.74 (s, 2H, NH$_2$), 6.16 (t, 1H, C$_1$·H), 6.86 (s, 1H, Im-H), 7.16 (s, 1H, Im-H), 7.25 (s, 1H, NH), 7.67 (s, 1H, Im-H), 7.92 (s, 1H, C$_8$H). Anal. Calcd. for C$_{16}$H$_{22}$N$_8$O$_3$ (374.39): C, 51.32; H, 5.92; N, 29.93. Found: C, 51.02; H, 5.93; N, 29.46.

EXAMPLE 50

3',5'-Di-O-isobutyryl-2-amino-N$_2$-isobutyryl-N$_6$-[imidazol-1-yl(propyl)]-9-(2-deoxy-β-D-erythro-pentofuranosyl)adenosine. (51)

To a well dried stirred solution of the substrate 50 (0.5 g, 1.33 mmol) [co-evaporated three times with dry pyridine (3×50 mL)] in dry pyridine (50 mL) at 0° C. was added isobutyryl chloride (434 μL, 4.14 mmol) diluted in dry pyridine (10 mL) optionally containing one equivalent of triethylamine during a period of 1 hour. After the addition, the reaction mixture was allowed to stir for an additional 1 h and quenched with CH$_3$OH (10 mL). The solvent was removed to give a brown oil. The oil was dissolved in CH$_2$Cl$_2$ (50 mL) and washed with 5% NaHCO$_3$ (20 mL), water (20 mL), and brine (20 mL). The organic extract was dried over anhydrous Na$_2$SO$_4$ filtered and evaporated to dryness. The residue was purified by flash chromatography over silica gel using CH$_2$Cl$_2$→CH$_3$OH as the eluent. The pure fractions were collected together and evaporated to give 0.5 g (72%) of 51 as an oil: $^1$H NMR (DMSO-d$_6$): δ1.16 (m, 18H, CH$_3$), 2.11 (m, 2H, CH$_2$), 2.62 (m, 2H, C$_2$·H), 2.78–2.90 (m, 3H, isobutyryl methine), 3.44 (m, 2H, CH$_2$), 4.07 (m, 2H, CH$_2$), 4.26 (s, 2H, C$_5$·CH$_2$), 4.37 (m, 1H, C$_4$·H), 5.43 (m, 1H, C$_3$·H), 6.32 (t, 1H, C$_1$·H), 6.89 (s, 1H, Im-H), 7.23 (s, 1H, Im-H), 7.67 (s, 1H, Im-C$_2$H), 7.86 (bs, 1H, NH), 8.23 (s, 1H, C$_8$H), 9.84 (bs, 1H, NH). Anal. Calcd. for C$_{28}$H$_{40}$N$_8$O$_6$ (584.66): C, 57.52; H, 6.89; N, 19.17. Found: C, 57.42; H, 6.59; N, 20.01.

EXAMPLE 51

N$_2$-Isobutyryl-2-amino-N$_6$-[imidazol-1-yl(propyl)]-9-(2-deoxy-β-D-erythro-pentofuranosyl)adenosine. (52)

The compound 51 (0.58 g, 1.0 mmol) was dissolved in a mixture of pyridine (10 mL) and methanol (10 mL), diluted with water (10 mL), and cooled to 0° C. in an ice-salt bath. To this cold stirred solution was added pre-cooled 1N NaOH (2.2 mL, 2.2 mmol) all at once. The reaction mixture was stirred at 0° C. for 10 minutes and neutralized with Dowex H$^+$ resin (pyridinium form). The resin was filtered and washed with pyridine (10 mL) and methanol (10 mL). The filtrate was evaporated to dryness to give a foam. The foam was dissolved in methanol (20 mL), adsorbed on silica gel (60–100 mesh, 5 g) and evaporated to dryness. The dried silica gel was placed on top of silica column (2×10 cm) packed in methylene chloride. The column was eluted with CH$_2$Cl$_2$→CH$_3$OH. The fractions having the product were collected and evaporated to give 52 (0.30 g, 67%) as white form. $^1$H NMR (DMSO-d$_6$): δ1.02 (m, 6H, CH$_3$), 2.05 (m, 2H, CH$_2$), 2.26 (m, 1H, C$_2$·H), 2.64 (m, 1H, C$_2$·H), 2.90 (m, 1H, isobutyryl methine), 3.22 (m, 2H, CH$_2$), 3.46 (s, 2H, C$_5$·CH$_2$), 3.81 (m, 1H, C$_4$·H), 4.05 (m, 2H, CH$_2$), 4.33 (m, 1H, C$_3$·H), 4.93 (m, 1H, C$_5$·OH), 5.30 (m, 1H, C$_3$·OH), 6.24 (t, 1H, C$_1$·H), 6.84 (s, 1H, Im-H), 7.16 (s, 1H, Im-H), 7.62 (s, 1H, Im-H), 7.92 (bs, 1H, NH), 8.22 (s, 1H, C$_8$H), 9.80 (bs, 1H, NH). Anal. Calcd. for C$_{20}$H$_{28}$N$_8$O$_4$·½ H$_2$O (453.49): C, 52.96; H, 6.45; N, 24.71. Found: C, 52.93; H, 6.22; N, 24.55.

EXAMPLE 52

5'-O-(4,4'-Dimethoxytrityl)-N$_2$-isobutyryl-2-amino-N$_6$-[imidazol-1-yl-(propyl)]-9-(2-deoxy-β-D-erythro-pentofuranosyl)adenosine (53).

The substrate 52 (2.90 g, 6.52 mmol) was coevaporated with dry pyridine (3×50 mL) and dissolved in dry pyridine (100 mL). To this stirred solution triethylamine (1.10 mL, 7.82 mmol) and 4,4'-dimethoxytrityl chloride (3.32 g, 9.79 mmol) were added at room temperature under argon atmosphere. After the addition of DMTCl, the reaction mixture was stirred for an additional 20 h at room temperature. The reaction was quenched with methanol (10 mL) and evaporated to dryness in high vacuum. The residue was dissolved in methylene chloride (200 mL) and washed with 5% NaHCO$_3$ solution (20 mL), water (20 mL), and brine (20 mL). The organic extract was dried over anhydrous Na$_2$SO$_4$ and the solvent removed under reduced pressure to give an oil. The crude oil was purified using a flash column over silica gel with CH$_2$Cl$_2$→CH$_3$OH as eluent. The pure fractions were collected together and evaporated to give 3.90 g of 53 as a foam. $^1$H NMR (DMSO-d$_6$): δ1.02 (m, 6H, CH$_3$), 2.05 (m, 2H, CH$_2$), 2.26 (m, 1H, C$_2$·H), 2.64 (m, 1H, C$_2$·H), 2.90 (m, 1H, isobutyryl methine), 3.22 (s, 2H, C$_5$·CH$_2$), 3.46 (m, 2H, CH$_2$), 3.81 (m, 1H, C$_4$·H), 4.05 (m, 2H, CH$_2$), 4.33 (m, 1H, C$_3$·H), 4.93 (m, 1H, C$_5$·OH), 5.30 (m, 1H, C$_3$·OH), 6.42 (t, 1H, C$_1$·H), 6.84 (s, 1H, Im-H), 7.16 (s, 1H, Im-H), 7.62 (s, 1H, Im-C$_2$H), 7.92 (bs, 1H, NH), 8.20 (s, 1H, C$_8$H), 9.80 (bs, 1H, NH). Anal. Calcd. for C$_{41}$H$_{46}$N$_8$O$_6$ (746.87): C, 65.93; H, 6.21; N, 15.0. Found: C, 65.85; H, 6.52; N, 14.77.

EXAMPLE 53

3'-O-[(N,N-diisopropylamino) (β-cyanoethoxy) phosphanyl]-5'-O-(4,4'-dimethoxytrityl)-N$_2$-isobutyryl-2-amino-N$_6$-[imidazol-1-yl(propyl)]-9-(2-deoxy-β-D-erythro-pentofuranosyl)adenosine. (54)

The substrate 53 (2.5 g, 2.79 mmol) was dissolved in dry pyridine (30 mL) and evaporated to dryness. This was repeated three times to remove the last traces of water and dried under high vacuum over solid sodium hydroxide overnight. The dried 53 was dissolved in dry dichloromethane (30 mL) and cooled to 0° C. under argon atmosphere. To this cold stirred solution was added N,N-diisopropylethylamine (0.72 g, 5.6 mmol) followed by (β-cyanoethoxy)-chloro(N,N-diisopropylamino)phosphane (1.32 g, 5.6 mmol) dropwise over a period of 15 min. The reaction mixture was stirred at 0° C. for 1 h and at room temperature for 2 h. The reaction mixture was diluted with dichloromethane (100 mL) and washed with brine (50 mL). The organic extract was dried over anhydrous Na$_2$SO$_4$ and the solvent was removed under reduced pressure. The residue was purified by flash chromatography over silica gel using hexane/acetone containing 1% triethylamine as the eluent. The main fractions were collected and evaporated to dryness. The residue was dissolved in dry dichloromethane (10 mL) and added dropwise into a stirred solution of hexane (1500 mL), during 30 min. After the addition, the stirring was continued for an additional 1 hour at room temperature under argon. The precipitated solid was filtered, washed with hexane and dried over solid NaOH under vacuum overnight to give 2.0 g 65%) of the title compound as a colorless powder.

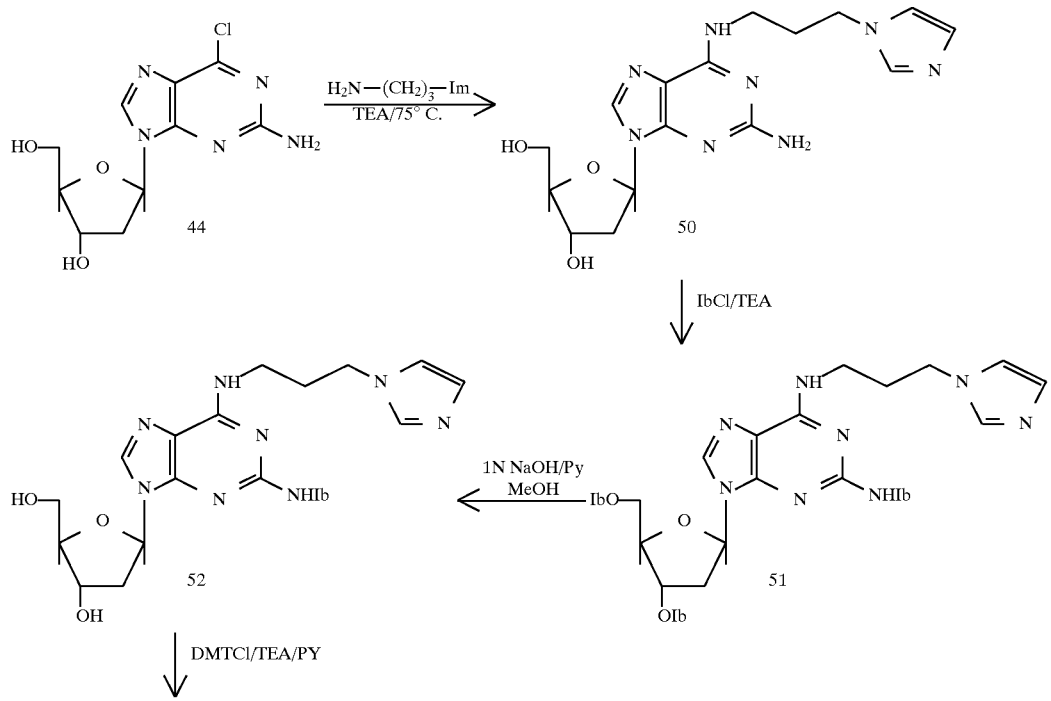

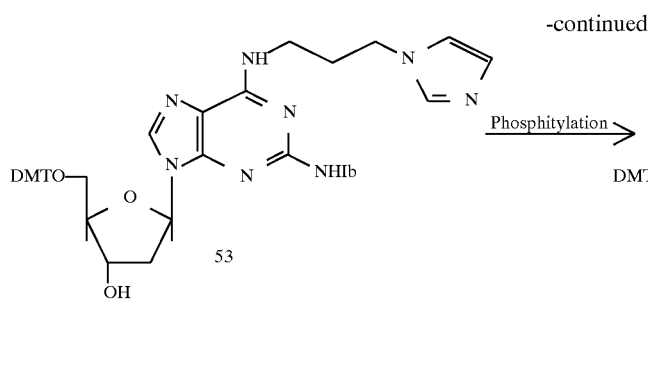 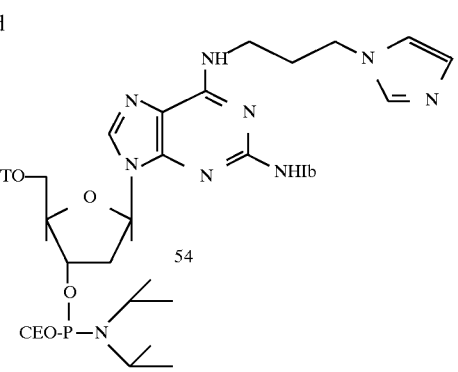

Phosphitylation

EXAMPLE 54

$N_6$-[(Imidazol-1-yl(propyl)]-9-(2-deoxy-β-D-erythro-pentofuranosyl)adenosine. (58)

A mixture of 6-chloro-9-(2'-deoxy-3',5'-di-O-p-toluoyl-β-D-erythro-pentofuranosyl)purine (55, 5.0 g, 9.86 mmol), 1-(3-aminopropyl)imidazole (2.6 mL, 22.0 mmol), and TEA (1.5 mL, 10.0 mmol) in 2-methoxyethanol (60 mL) was heated at 75° C. in a steel bomb for 18 h. The steel bomb was cooled to 0° C., opened and the solution evaporated to dryness. The crude product showed the presence of two compounds, presumably 56 and 57. The crude 56 and 57 (8.21 g) were stirred with saturated $CH_3OH/NH_3$ (750 mL) in a steel bomb at room temperature for 12 hours. The steel bomb was cooled to 0° C., opened carefully and evaporated to dryness. The residue was dissolved in methanol (50 mL), adsorbed on silica gel (20 g), and evaporated to dryness. The dried silica gel was placed on top of silica column (250–400 mesh, 10×30 cm) packed in $CH_2Cl_2$. The column was eluted with $CH_2Cl_2 \rightarrow CH_3OH$. The fractions having the product were pooled together and evaporated to dryness to afford 4.62 g (88%) of 58 as a colorless solid. $^1H$ NMR (DMSO-$d_6$): δ2.00 (m, 2H, $CH_2$), 2.25 (m, 1H, $C_2H$), 2.73 (m, 1H, $C_2H$), 3.45 (m, 2H, $CH_2$), 3.53 (m, 2H, $C_5 CH_2$), 3.85 (m, 1H, $C_4H$), 4.00 (m, 2H, $CH_2$), 4.39 (m, 1H, $C_3H$), 5.24 (t, 1H, $C_5OH$), 5.34 (d, 1H, $C_3OH$), 6.37 (t, 1H, $C_1H$), 6.86 (s, 1H, Im-H), 7.20 (s, 1H, Im-H), 7.62 (s, 1H, Im-$C_2H$), 8.00 (bs, 1H, NH), 8.20 (s, 1H, $C_8H$), 8.34 (s, 1H, $C_2H$). Anal. Calcd. for $C_{16}H_{21}N_7O_3$ (359.38): C, 53.47; H, 5.89; N, 27.28. Found: C, 53.32; H, 5.86; N, 27.01.

EXAMPLE 55

5'-O-(4,4'-Dimethoxytrityl)-$N_6$-[imidazol-1-yl (propyl)]-9-(2-deoxy-β-D-erythro-pentofuranosyl)adenosine. (59)

The substrate 58 (2.34 g, 6.51 mmol) was dried by coevaporation with dry pyridine (3×50 mL) and dissolved in dry pyridine (70 mL). To this stirred solution triethylamine (1 mL, 7.16 mmol) was added and stirred for 30 min at room temperature. 4,4'-Dimethoxytrityl chloride (3.31 g, 9.77 mmol) was added in one portion and the stirring was continued at room temperature under an atmosphere of argon for 15 hours. The reaction was quenched with methanol (10 mL) and the solvent removed under reduced pressure. The residue was dissolved in methylene chloride (200 mL) and washed with 5% $NaHCO_3$ solution (20 mL), water (20 mL) and brine (20 mL). The organic extract was dried over anhydrous $Na_2SO_4$ and removal of solvent gave an oil. The crude oil was purified by flash column over silica gel using $CH_2Cl_2 \rightarrow CH_3OH$ as eluent. The pure product 59 (4.26 g, 99%) was obtained as a foam: $^1H$ NMR (DMSO-$d_6$): δ2.05 (m, 2H, $CH_2$), 2.45 (m, 1H, $C_2H$), 2.84 (m, 1H, $C_2H$), 3.15 (m, 1H, $CH_2$), 3.68 (s, 8H, $CH_2$ & 2 $OCH_3$), 4.00 (m, 2H, $C_4H$ & $C_5 CH_2$), 4.33 (m, 1H, $C_3H$), 5.38 (d, 1H, $C_3OH$), 6.35 (t, 1H, $C_1H$), 6.77 (m, 4H, phenyl), 6.84 (s, 1H, Im-H), 7.20 (m, 9H, 2×phenyl-H), 7.30 (s, 1H, Im-H), 7.62 (s, 1H, Im-$C_2H$), 7.92 (bs, 1H, NH), 8.15 (s, 1H, $C_8H$), 8.25 (s, 1H, $C_2H$). Anal. Calcd. for $C_{37}H_{39}N_7O_5 \cdot \frac{1}{4} H_2O$ (666.24): C, 66.69; H, 5.98; N, 14.72. Found: C, 66.92; H, 6.35; N, 14.50.

EXAMPLE 56

3'-O-[(N,N-diisopropylamino) (β-cyanoethoxy) phosphanyl]-5'-O-(4,4'-dimethoxytrityl)-$N_6$-[imidazol-1-yl(propyl)]-9-(2-deoxy-β-D-erythro-pentofuranosyl)adenosine (60).

The dried (dried over solid NaOH under vacuum overnight) substrate 59 (2.47 g, 3.70 mmol) was dissolved in dry methylene chloride (60 mL) and cooled to 0° C. under an atmosphere of argon. To this cold stirred solution was added N,N-diisopropylethylamine (1.29 mL, 7.40 mmol) followed by (β-cyanoethoxy)-chloro(N,N-diisopropylamino)phosphane (1.66 mL, 7.40 mmol) dropwise over a period of 15 minutes. The reaction mixture was stirred at 0° C. for 1 h and at room temperature for 2 hours and diluted with dichloromethane (100 mL). The methylene chloride extract was washed with saturated $NaHCO_3$ (50 mL) and brine (50 mL). The organic extract was dried over anhydrous $Na_2SO_4$ and the solvent was removed under reduced pressure. The residue was purified by flash chromatography over silica gel using methylene chloride/ acetone containing 1% triethylamine as the eluent. The main fractions were collected and evaporated to dryness to yield 60 as a colorless foam. The foam was dissolved in dry dichloromethane (10 mL) and added dropwise into a stirred solution of hexane (1500 mL), during 30 min. After the addition, the stirring was continued for additional 1 h at room temperature under argon. The precipitated solid was filtered, washed with hexane and dried over solid NaOH under vacuum overnight to give 2.0 g (65%) of the title compound as a colorless powder.

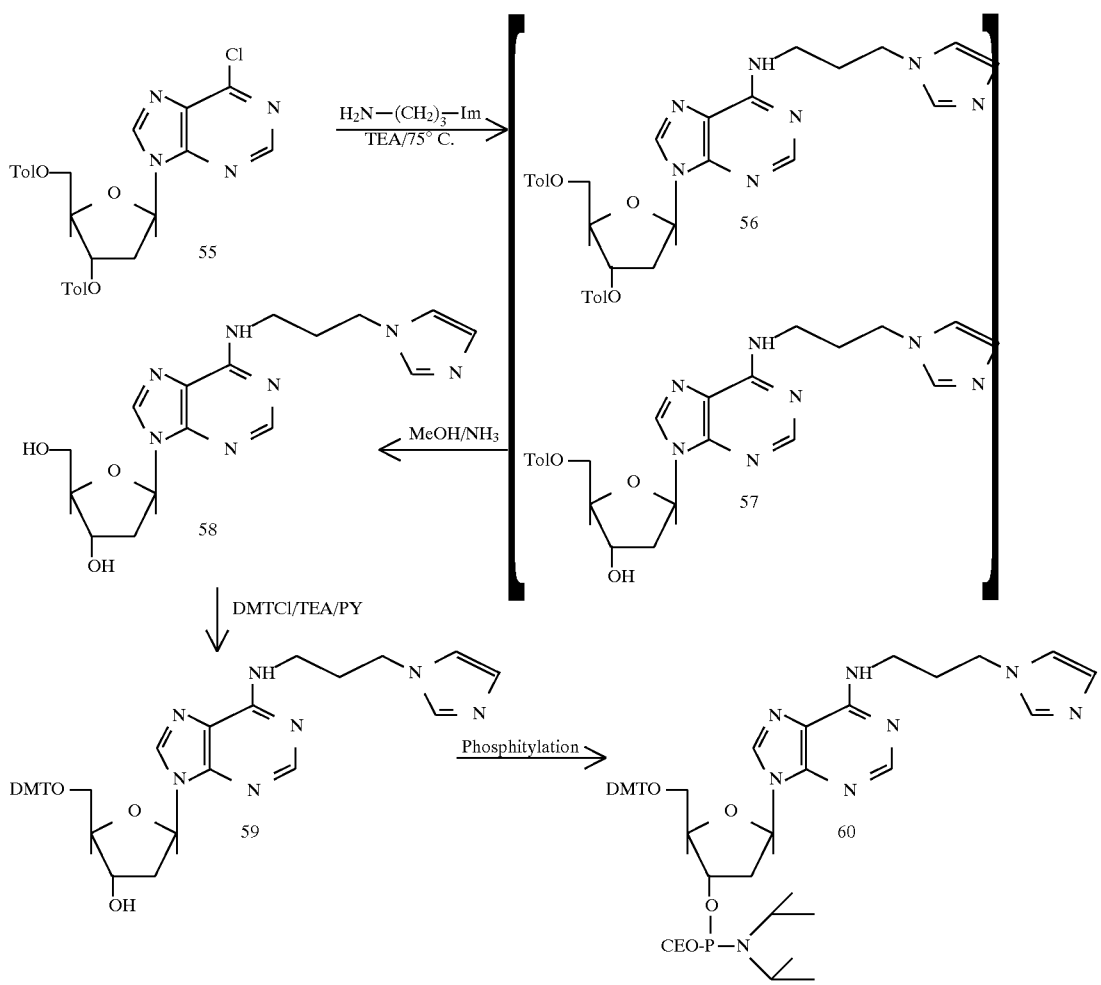

EXAMPLE 57

N$_6$-[Imidazol-4-yl(ethyl)]-9-(2-deoxy-3,5-di-O-p-toluoyl-β-D-erythro-pentofuranosyl)adenosine. (61)

6-Chloro-9-(2-deoxy-3,5-di-O-p-toluoyl-β-D-erythropentofuranosyl)purine (54, 11.5 g, 22.68 mmol), histamine (3.03 g, 27.22 mmol), triethylamine (3.80 mL, 27.22 mmol) and 2-methoxyethanol (100 mL) were placed in a steel bomb and heated at 75° C. overnight. The steel bomb was cooled to 0° C., opened carefully and the solvent removed under vacuum. The crude product was dissolved in methanol (75 mL), mixed with silica gel (60–100 mesh, 14 g) and evaporated to dryness. The dried material was placed on top of a silica column (15×38 cm) packed in methylene chloride. The column was eluted with CH$_2$Cl$_2$→CH$_3$OH. The pure fractions were combined and concentrated to give 12.75 g (97%) of 61 as clear foam. $^1$H NMR (Me$_2$SO-d$_6$) δ2.38 (2 s, 6H, 2×CH$_3$), 2.72 (m, 1H, C$_2$·H), 3.30 (m, 1H, C$_2$·H), 2.90 (m, 2H, CH$_2$), 3.70 (m, 2H, CH$_2$), 3.82 (m, 2H, C$_5$·CH$_2$), 4.62 (m, 1H, C$_4$·H), 5.80 (m, 1H, C$_3$·H), 6.35 (t, 1H, J$_{1',2'}$=6.20 Hz, C$_1$·H ), 6.90 (s, 1H, Im-H ), 7.25 (dd, 4H, phenyl-H), 7.78 (s, 1H, Im-H ), 7.90 (dd, 4H, phenyl-H), 8.20 (s, 1H, C$_8$H), 8.35 (s, 1H, C$_2$H). Anal. Calcd for C$_{31}$H$_{31}$N$_7$O$_5$·2×CH$_3$OH. H$_2$O (662.71): C, 59.80; H, 6.24; N, 14.79. Found: C, 59.71; H, 6.52; N, 14.70.

EXAMPLE 58

N$_6$-[Imidazol-4-yl(ethyl)]-9-(2-deoxy-β-D-erythro-pentofuranosyl)adenosine. (62)

A solution of 61 (4.07 g, 7.00 mmol) in CH$_3$OH/NH$_3$(250 mL) was stirred at room temperature in a steel bomb for 12 h. The steel bomb was cooled to 0° C., opened carefully and evaporated to dryness. The residue was dissolved in methanol (30 mL), adsorbed on silica gel (10 g), and evaporated to dryness. The dried silica gel was placed on top of silica column (250–400 mesh, 10×33 cm) packed in CH$_2$Cl$_2$. The column was eluted with CH$_2$Cl$_2$→CH$_3$OH. The fractions having the products was pooled together and evaporated to dryness to afford 1.40 g (60%) of 62 as a colorless foam. $^1$H NMR (DMSO-d$_6$): δ2.25 (m, 1H, C$_2$·H), 2.65 (m, 1H, C$_2$·H), 2.80 (t, 2H, CH$_2$), 3.53 (m, 2H, CH$_2$), 3.85 (m, 3H, C$_4$·H & C$_5$·CH$_2$), 4.39 (m, 1H, C$_3$·H), 6.37 (t, 1H, C$_1$·H), 6.86 (s, 1H, Im-H), 7.66 (s, 1H, Im-H), 7.86 (bs, 1H, NH), 8.22 (s, 1H, C$_8$H), 8.34 (s, 1H, C$_2$H). Anal. Calcd. for C$_{15}$H$_{19}$N$_7$O$_3$·3 H$_2$O (399.32): C, 45.14; H, 6.31; N, 24.55. Found: C, 45.24; H, 6.43; N, 24.28.

EXAMPLE 59

3',5'-O-(Tetraisopropyldisiloxane-1,3-diyl)-N$_6$-[Imidazol-4-yl(ethyl)]-9-(2-deoxy-β-D-erythro-pentofuranosyl)adenosine. (63)

The compound 62 (1.38 g, 3.99 mmol) was dissolved in dry DMF (50 mL) dry pyridine (50 mL), and evaporated to dryness. This was repeated for three times to remove all the water. The dried substrate was dissolved in dry pyridine (75 mL) and allowed to stir at room temperature under an atmosphere of argon. To this stirred solution was added dry triethylamine (1.20 mL, 8.0 mmol) and 1,3-dichloro-1,1,3,3-tetraisopropyldisiloxane (TipSiCl, 2.54 mL, 8.0 mmol) during 15 min period. After the addition of TipSiCl, the reaction mixture was allowed to stir at room temperature overnight. The solvent was evaporated under reduced pressure to dryness. The cake obtained was dissolved in methylene chloride (150 mL) and washed with 5% $NaHCO_3$ solution (50 mL), water (35 mL) and brine (30 mL). The extract was dried over anhydrous $Na_2SO_4$ and evaporated to dryness. The residue was purified by flash chromatography over silica gel using $CH_2Cl_2$/MeOH as the eluent. The pure fractions were pooled and evaporated to dryness to give 1.48 g (63%) of 63 as amorphous powder: $^1$H NMR (Me$_2$SO-d$_6$) δ1.04 (m, 28H), 2.54 (m, 1H, C$_2$,H), 2.82 (mi, 3H, C$_2$H & CH$_2$), 3.72 (m, 3H, C$_5$,CH$_2$ & C$_4$,H), 3.88 (m, 2H, CH$_2$), 5.2 (m, 1H, C$_3$,H), 6.28 (m, 1H, C$_1$,H), 6.82 (s, 1H, Im-H), 7.54 (s, 1H, Im-H), 7.85 (bs, 1H, NH), 8.15 (s, 1H, C$_8$H), 8.20 (s, 1H, C$_2$H). Anal. Calcd for $C_{27}H_{45}N_7O_4Si_2 \cdot CH_3OH$ (619.89): C, 54.25; H, 7.97; N, 15.82. Found: C, 54.54; H, 7.72; N, 15.86.

EXAMPLE 60

3',5'O-(Tetraisopropyldisiloxane-1,3-diyl)-N$_6$-[(N$_1$-diphenylcarbamo-yl)imidazol-4-yl(ethyl)]-9-(2-deoxy-β-D-erythro-pentofuranosyl)adenosine. (64)

To a well stirred solution of the substrate 63 (2.57 g, 4.37 mmol) in dry pyridine (50 mL) was added N,N-diisopropylethylamine (1.52 mL, 8.74 mmol) followed by diphenylcarbamoyl chloride (2.03 g, 8.74 mmol) at room temperature. The reaction mixture was stirred at room temperature overnight and evaporated to dryness. The residue was dissolved in CH$_2$Cl$_2$ (400 mL), washed with water (100 mL), and brine (50 mL), dried over MgSO$_4$ and evaporated to dryness. The residue on purification by flash chromatography using methylene chloride/acetone (8:2) gave the titled compound in 58% (1.97 g) yield: $^1$H NMR (Me$_2$SO-d$_6$) δ1.04 (m, 28H), 2.52 (m, 1H, C$_2$,H), 2.70 (m, 1H, CH$_2$), 2.82 (m, 1H, C$_2$,H), 3.72 (m, 3H, C$_5$,CH$_2$ & C$_4$,H), 3.88 (m, 2H, CH$_2$), 5.22 (m, 1H, C$_3$,H), 6.32 (dd, 1H, C$_1$,H), 6.95 (s, 1H, Im-H), 7.35 (m, 10H, phenyl-H), 7.72 (s, 1H, Im-H), 7.78 (bs, 1H, NH), 8.15 (s, 1H, C$_8$H), 8.22 (s, 1H, C$_2$H).

EXAMPLE 61

N$_6$-[(N$_1$-Diphenylcarbamoyl)imidazol-4-yl(ethyl)]-9-(2-deoxy-β-D-erythro-pentofuranosyl)adenosine. (65)

To a stirred solution of the protected derivative 64 (1.45 g, 1.85 mmol) in pyridine (30 mL) was added a 0.5M solution (5 mL, 2.5 mmol) of tetrabutylammonium fluoride [prepared in a mixture of tetrahydrofuran-pyridine-water (8:1:1; v/v/v; 20 mL)] at room temperature. The reaction mixture was stirred for 10 min and quenched with H$^+$ resin (pyridinium form) to pH 6-7. The resin was filtered off, washed with pyridine (25 mL) and methanol (30 mL). The combined filtrate was evaporated to dryness under vacuum and the residue on purification by flash chromatography using CH$_2$Cl$_2$/MeOH (95:5) gave 0.7 g (77%) of 65 as a foam: $^1$H NMR (Me$_2$SO-d$_6$) δ2.25 (m, 1H, C$_2$,H), 2.70 (m, 3H, CH$_2$ & C$_2$,H), 3.62 (m, 4H, C$_5$,CH$_2$ & ImCH$_2$), 3.84 (m, 1H, C$_4$,H), 4.42 (m, 1H, C$_3$,H), 5.22 (t, 1H, C$_5$,OH), 5.30 (bs, 1H, C$_3$,OH), 6.35 (t, 1H, C$_1$,H), 6.95 (s, 1H, Im-H), 7.35 (m, 10H, phenyl-H), 7.62 (s, 1H, Im-H), 7.77 (bs, 1H, NH), 8.18 (s, 1H, C$_8$H), 8.32 (s, 1H, C$_2$H). Anal. Calcd for $C_{28}H_{28}N_8O_4 \cdot \frac{1}{4} H_2O$ (545.07): C, 61.69; H, 5.27; N, 20.55. Found: C, 61.92; H, 5.44; N, 20.01.

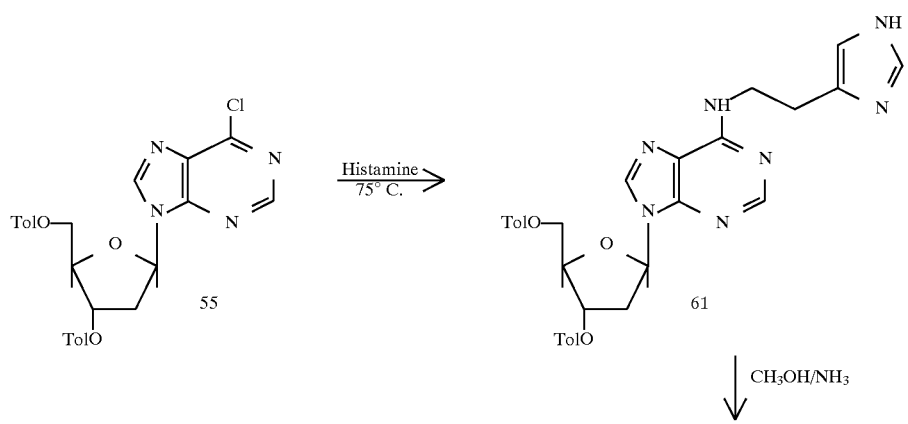

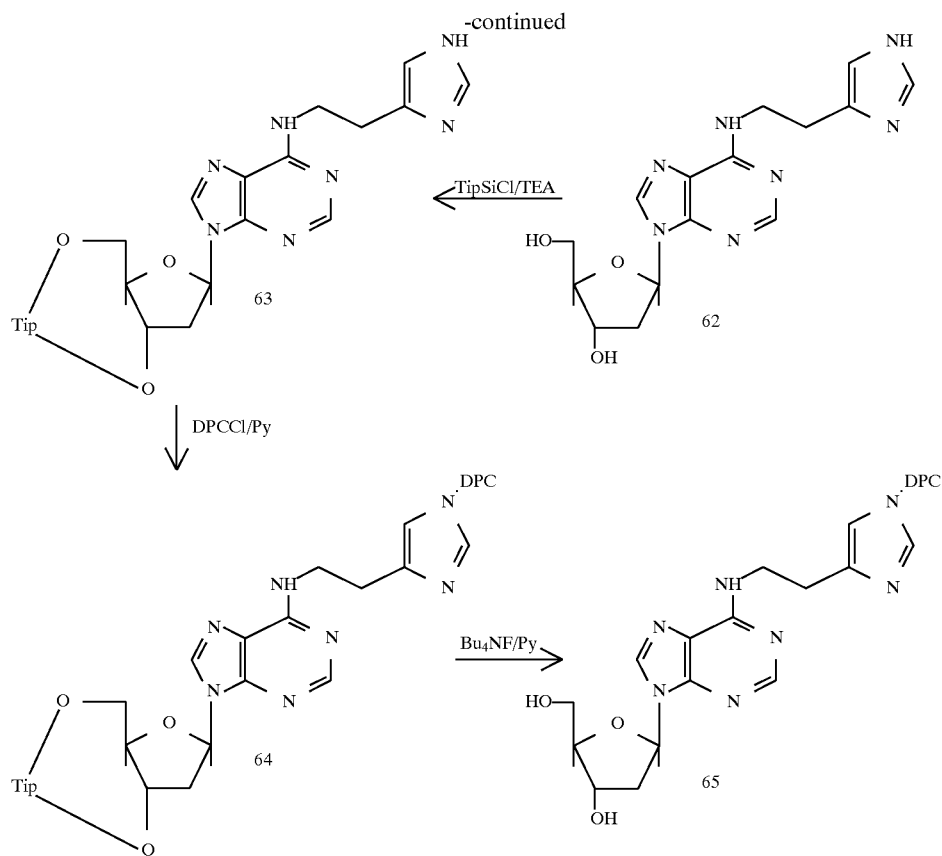

EXAMPLE 62

5'-O-(4,4'-Dimethoxytrityl)-N$_6$-[(N$_1$-diphenylcarbamoyl)imidazol-4-yl-(ethyl)]-9-(2-deoxy-β-D-erythro-pentofuranosyl)adenosine. (66)

To a dried solution of 65 (0.45 g, 0.57 mmol) in dry pyridine (35 mL) was added triethylamine (0.18 mL, 1.25 mmol) followed by 4,4'-dimethoxytrityl chloride (0.43 g, 1.25 mmol). The reaction mixture was stirred at room temperature under an atmosphere of argon for 15 hours. The reaction was quenched with methanol (10 mL) and the solvent removed under reduced pressure. The residue was dissolved in methylene chloride (100 mL) and washed with 5% NaHCO$_3$ solution (20 mL), water (20 mL) and brine (20 mL). The organic extract was dried over anhydrous Na$_2$SO$_4$ and the solvent removed to give an oil. The crude oil was purified using flash column chromatography over silica gel with CH$_2$Cl$_2$→CH$_3$OH as eluent. The pure product 66 (0.62 g, 88%) was obtained as a clear foam: $^1$H NMR (DMSO-d$_6$): δ2.45 (m, 1H, C$_2$H), 2.70 (t, 2H, CH$_2$), 2.90 (m, 1H, C$_2$H), 3.22 (m, 2H, ImCH$_2$), 3.62 (m, 2H, C$_5$·CH$_2$), 3.72 (s, 6H, 2×OCH$_3$), 4.04 (m, 1H, C$_4$·H), 4.50 (bs, 1H, C$_3$·H), 5.48 (bs, 1H, C$_3$·OH), 6.40 (t, 1H, C$_1$·H), 6.80 (m, 4H, phenyl-H), 6.95 (s, 1H, Im-H), 7.30 (m, 19H, phenyl-H), 7.65 (s, 1H, Im-H), 7.80 (bs, 1H, NH), 8.18 (s, 1H, C$_8$H), 8.26 (s, 1H, C$_2$H). Anal. Calcd for C$_{49}$H$_{46}$N$_8$O$_6$ (842.92): C, 69.82; H, 5.50; N, 13.29. Found: C, 69.65; H, 6.00; N, 13.11.

EXAMPLE 63

3'-O-[(N,N-diisopropylamino) (β-cyanoethoxy) phosphanyl]-5'-O-(4,4'-dimethoxytrityl)-N$_6$-[(N$_1$-diphenylcarbamoyl)imidazol-4-yl(ethyl)]-9-(2-deoxy-β-D-erythro-pentofuranosyl)adenosine. (67)

The dried (dried over solid NaOH under vacuum overnight) substrate 66 (2.47 g, 3.70 mmol) was dissolved in dry methylene chloride (60 mL) and cooled to 0° C. under argon atmosphere. To this cold stirred solution was added N,N-diisopropylethylamine (1.29 mL, 7.40 mmol) followed by (β-cyano-ethoxy)-chloro(N,N-diisopropylamino) phosphane (1.66 mL, 7.40 mmol) dropwise over a, period of 15 min. The reaction mixture was stirred at 0° C. for 1 hour and at room temperature for 2 hours and diluted with dichloromethane (100 mL). The methylene chloride extract was washed with sat NaHCO$_3$ (50 mL) and brine (50 mL). The organic extract was dried over anhydrous Na$_2$SO$_4$ and the solvent was removed under reduced pressure. The residue was purified by flash chromatography over silica gel using methylene chloride/acetone containing 1% triethylamine as the eluent. The main fractions were collected and evaporated to dryness to give a foam. This foam was dissolved in dry CH$_2$Cl$_2$ (10 mL) and dropped into a stirring solution of dry hexane under argon over a period of 1 h. The precipitated solid was filtered, washed with hexane and dried over NaOH pellets at vacuum for 10 hours. Yield 2.5 g (85%).

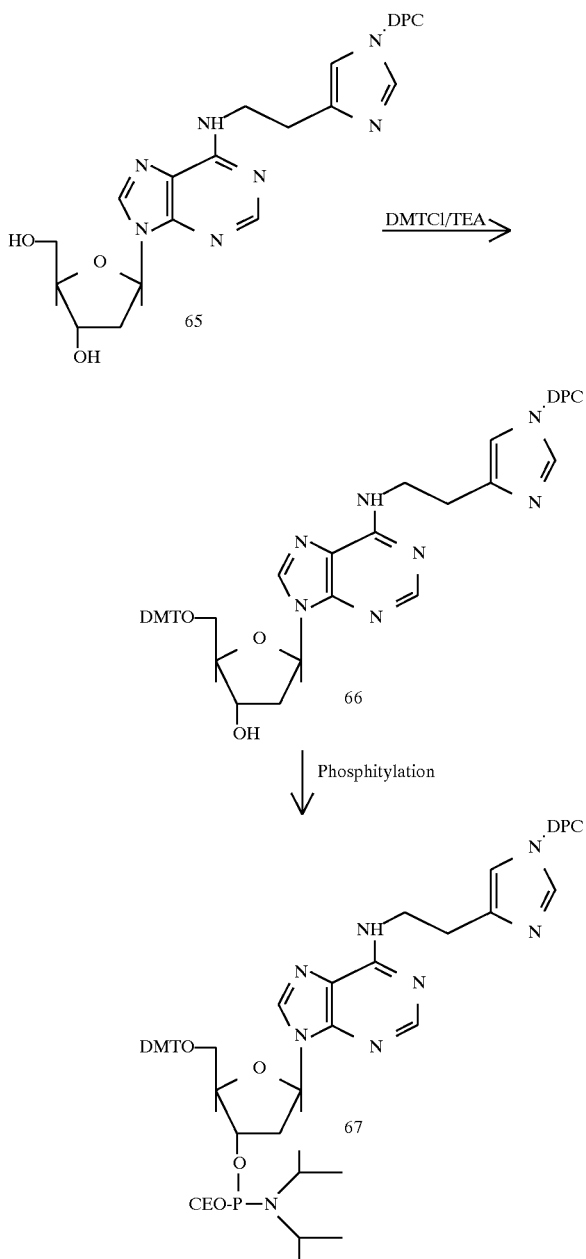

$C_5H_2, C_4H$), 4.74 (m, 1H, $C_3H$), 6.14 (t, 1H, $J_{1',2'}$=6.20 Hz, $C_1H$), 6.72 (bs, 1H, NH), 7.78 (s, 1H, $C_8H$). Anal. Calcd for $C_{25}H_{46}N_6O_5Si_2$. C, 52.97; H, 8.18; N, 14.83. Found: C, 52.59; H, 8.04; N, 14.56.

EXAMPLE 65

3',5'-O-(Tetraisopropyldisiloxane-1,3-diyl)-$N_2$-(3-trifluoroacetamido-propyl)-9-(2'-deoxy-β-D-erythro-pentofuranosyl)guanosine. (69)

To a well stirred solution of the substrate 68 (9.6 g, 16.9 mmol) in dry pyridine was added triethylamine (5.05 g, 50 mmol) followed by trifluoroacetic anhydride (7.14 g, 34 mmol) slowly at 0° C. After the addition of TFAA, the reaction mixture was stirred at room temperature for 6 h. The reaction was evaporated to dryness and the residue was dissolved in $CH_2Cl_2$ (150 mL). The organic extract was washed with 5% $NaHCO_3$ solution (50 mL), water (50 mL) and brine (50 mL). The extract was dried over anhydrous $MgSO_4$ and the solvent was removed under reduced pressure. The residue was purified by flash chromatography over silica gel using $CH_2Cl_2$→acetone as the eluent. The pure fractions were collected and evaporated to give a solid: mp 205°–208° C.; yield 5.7 g (44%); $^1$H NMR ($Me_2SO$-$d_6$) δ1.00 (m, 28H), 1.75 (t, 2H, $CH_2$), 2.42 (m, 1H, $C_2H$), 2.80 (m, 1H, $C_2H$), 3.22 (m, 4H, $2CH_2$), 3.40 (m, 3H, $C_5H_2, C_4H$), 4.72 (m, 1H, $C_3H$), 6.14 (t, 1H, $J_{1',2'}$=6.20 Hz, $C_1H$), 6.52 (t, 1H, NH), 7.80 (s, 1H, $C_8H$), 9.46 (t, 1H, NH), 10.62 (b s, 1H, NH). Anal. Calcd for $C_{27}H_{45}F_3N_6O_6Si_2$. C, 48.92; H, 6.84; N, 12.68. Found: C, 49.02; H, 6.80; N, 12.70.

EXAMPLE 66

3',5'-O-(Tetraisopropyldisiloxane-1,3-diyl)-6-O-diphenylcarbamoyl-$N_2$-(3-trifluoroacetamidopropyl)-9-(2'-deoxy-β-D-erythro-pentofuranosyl)-guanosine. (70)

To a well dried solution of the substrate 69 (5.7 g, 7.5 mmol) in dry pyridine (100 mL) and dry dimethylformamide (50 mL) was added N,N-diisopropylethylamine (2.58 g, 20 mmol) and cooled to 0° C. under argon atmosphere. To this cold stirred solution was added diphenylcarbamoyl chloride (3.46 g, 15 mmol) at once. After the addition of DPCCl, the reaction mixture was stirred at room temperature for 4 h and evaporated to dryness. The residue was dissolved in $CH_2Cl_2$ (150 mL) and washed with 5% $NaHCO_3$ solution (50 mL), water (50 mL) and brine (50 mL). The $CH_2Cl_2$ extract was dried-over anhydrous $MgSO_4$ and evaporated to dryness. The residue was purified by flash chromatography over silica gel using $CH_2Cl_2$/EtOac as the eluent. The pure fractions were collected and evaporated to give 5.7 g (44%) of 70 as a foam: $^1$H NMR ($Me_2SO$-$d_6$) δ1.00 (m, 28H), 1.75 (m, 2H, $CH_2$), 2.50 (m, 1H, $C_2H$), 2.92 (m, 1H, $C_2H$), 3.28 (m, 4H, $2CH_2$), 3.82 (m, 3H, $C_5H_2, C_4H$), 4.76 (m, 1H, $C_3H$), 6.22 (m, 1H, $C_1H$), 7.30 (m, 1H, NH), 7.42 (m, 10H, ArH), 8.18 (s, 1H, $C_8H$), 9.42 (t, 1H, NH). Anal. Calcd for $C_{40}H_{54}F_3N_7O_7Si_2$. C, 55.98; H, 6.34; N, 11.43. Found: C, 55.87; H, 6.42; N, 11.62.

EXAMPLE 67

6-O-Diphenylcarbamoyl-$N_2$-(3-trifluoroacetamidopropyl)-9-(2-deoxy-β-D-erythro-pentofuranosyl)guanosine. (71)

The substrate 70 (8.32 g, 10.0 mmol) was dissolved in dry pyridine (75 mL) and allowed to stir at room temperature. To

EXAMPLE 64

3',5'-O-(Tetraisopropyldisiloxane-1,3-diyl)-$N_2$-(3-aminopropyl)-9-(2'-deoxy-β-D-erythro-pentofuranosyl)guanosine. (68)

1,3-Diaminopropane (2.96 g, 40 mmol) in 2-methoxyethanol (50 ml) was heated to 100° C. To this hot stirred solution was added the 2-chloro-nucleoside 36 (5.29 g, 10 mmol) in 2-methoxyethanol (70 ml) dropwise during 6 h period at 100° C. The reaction mixture was stirred at 100° C. temperature for 12 h and evaporated to dryness. The residue was dissolved in methanol (150 mL) and cooled to 0° C. The precipitated solid was filtered and dried. The dried material was recrystallized from ethanol to give crystalline material: mp 250°–253° C.; yield 4.7 g (83%); $^1$H NMR ($Me_2SO$-$d_6$) δ1.00 (m, 28H), 1.55 (t, 2H, $CH_2$), 2.62 (m, 1H, $C_2H$), 2.80 (m, 1H, $C_2H$), 3.22–4.00 (m, 9H, $2CH_2$, $NH_2$, this cold stirred solution was added 0.5M tetrabutylammonium fluoride (80 mL, 40 mmol, prepared in py:THF:H$_2$O; 5:4:1) at once. The reaction mixture was stirred at room temperature for 15 min, the pH was adjusted to 7 with H+resin. The reaction was filtered, washed with methanol (50 mL) and the filtrate evaporated to dryness. The residue was dissolved in CH$_2$Cl$_2$ (150 mL), washed with water (50 mL) and brine (50 mL). The organic extract was dried over anhydrous MgSO$_4$ and evaporated to dryness. The residue was purified by flash chromatography over silica gel using CH$_2$Cl$_2$→MeOH as the eluent. The pure fractions having the pure product was collected and evaporated to give 4.7 g (80%) as foam: $^1$H NMR (Me$_2$SO-d$_6$) δ1.76 (t, 2H, CH$_2$), 2.25 (m, 1H, C$_2$H), 2.72 (m, 1H, C$_2$H), 3.28 (m, 4H, 2CH$_2$), 3.55 (m, 2H, C$_5$CH$_2$), 3.84(m, 1H, C$_4$H), 4.40 (m, 1H, C$_3$H), 4.92 (t, 1H, C$_5$OH), 5.34 (d, 1H, C$_3$OH), 6.28 (t, 1H, J$_{1',2'}$=6.20 Hz, C$_1$H), 7.30 (m, 1H, NH), 7.42 (m, 10H, ArH), 8.28 (s, 1H, C$_8$H), 9.42 (t, 1H, NH). Anal. Calcd for C$_{28}$H$_{28}$F$_3$N$_7$O$_6$Si. C, 54.63; H, 4.59; N, 15.93. Found: C, 54.55; H, 4.61; N, 15.99.

EXAMPLE 68

5'-O-(4,4'-Dimethoxytrityl)-6-O-diphenylcarbamoyl-N$_2$-(3-trifluoro-acetamidopropyl)-9-(2-deoxy-β-D-erythro-pentofuranosyl)guanosine. (72)

The substrate 71 (3.5 g, 5.90 mmol) was dissolved in dry pyridine (30 mL) and evaporated to dryness. The dried 71 was dissolved in dry pyridine (100 mL) and treated with triethylamine (1.01 g, 10 mmol) under argon atmosphere. To this stirred solution was added 4,4'-dimethoxytrityl chloride (2.59 g, 7.67 mmol) and the stirring was continued at room temperature for 6 h. The reaction mixture was quenched with methanol (20 mL), stirred for 10 min and evaporated to dryness. The residue was dissolved in dichloromethane (150 mL), washed with 5% NaHCO$_3$ solution (40 mL), water (40 mL) and brine (50 mL). The organic extract was dried over anhydrous MgSO$_4$ and the solvent was removed under reduced pressure. The residue was purified by flash chromatography over silica gel using CH$_2$Cl$_2$→acetone as the eluent. The main fractions were collected and evaporated to dryness to give 4.5 g (85%) of the titled compound. $^1$H NMR (CDCl$_3$) δ1.66 (m, 2H, CH$_2$), 2.32 (m, 1H, C$_2$H), 2.75 (m, 1H, C$_2$H), 3.28 (m, 7H, C$_5$CH$_2$, 2 CH$_2$), 3.72 (m, 6H, 2 OCH$_3$), 3.92 (m, 1H, C$_4$H), 4.42 (m, 1H, C$_3$H), 5.34 (d, 1H, C$_3$OH), 6.30 (t, 1H, J$_{1',2'}$=6.20 Hz, C$_1$H), 6.74 (d, 4H, ArH), 7.30 (m, 24H, ArH, NH), 8.18 (s, 1H, C$_8$H), 9.40 (t, 1H, NH).

EXAMPLE 69

3'-O-[(N,N-diisopropylamino) (β-cyanoethoxy) phosphanyl]-5'-O-(4,4'-dimethoxytrityl)-6-O-diphenylcarbamoyl-N$_2$-(3-trifluoroacetamidopropyl)-9-(2-deoxy-β-D-erythro-pentofuranosyl) guanosine. (73)

The substrate 72 (4.3 g, 4.70 mmol) was dissolved in dry pyridine (30 mL) and evaporated to dryness. This was repeated three times to remove last traces of water and dried over solid sodium hydroxide overnight. The dried 72 was dissolved in dry dichloromethane (100 mL) and cooled to 0° C. under argon atmosphere. To this cold stirred solution was added N,N-diisopropylethylamine (1.29 g, 10 mmol) followed by (β-cyanoethoxy)chloro(N,N-diisopropylamino) phosphane (2.36 g, 10 mmol) dropwise over a period of 15 min. The reaction mixture was stirred at 0° C. for 1 h and at room temperature for 2 h. The reaction mixture was diluted with dichloromethane (100 mL), washed with 5% NaHCO$_3$ solution (50 mL), water (50 mL) and brine (50 mL). The organic extract was dried over anhydrous MgSO$_4$ and the solvent was removed under reduced pressure. The residue was purified by flash chromatography over silica gel using CH$_2$Cl$_2$→EtOAc containing 1% triethylamine as the eluent. The main fractions were collected and evaporated to dryness. The residue was dissolved in dry dichloromethane (20 mL) and added dropwise into a stirred solution of hexane (1500 mL), during 90 min. After the addition, the stirring was continued for additional 1 h at room temperature under argon. The precipitated solid was filtered, washed with hexane and dried over solid NaOH under vacuum overnight to give 4.0 g (76%) of the titled compound as colorless powder.

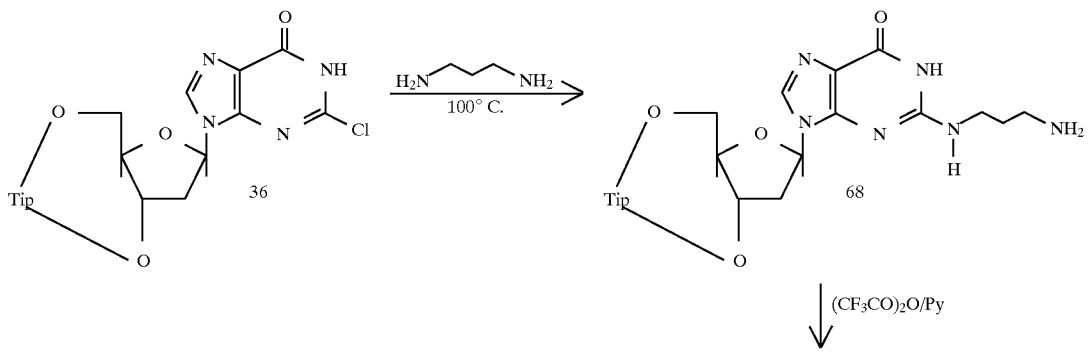

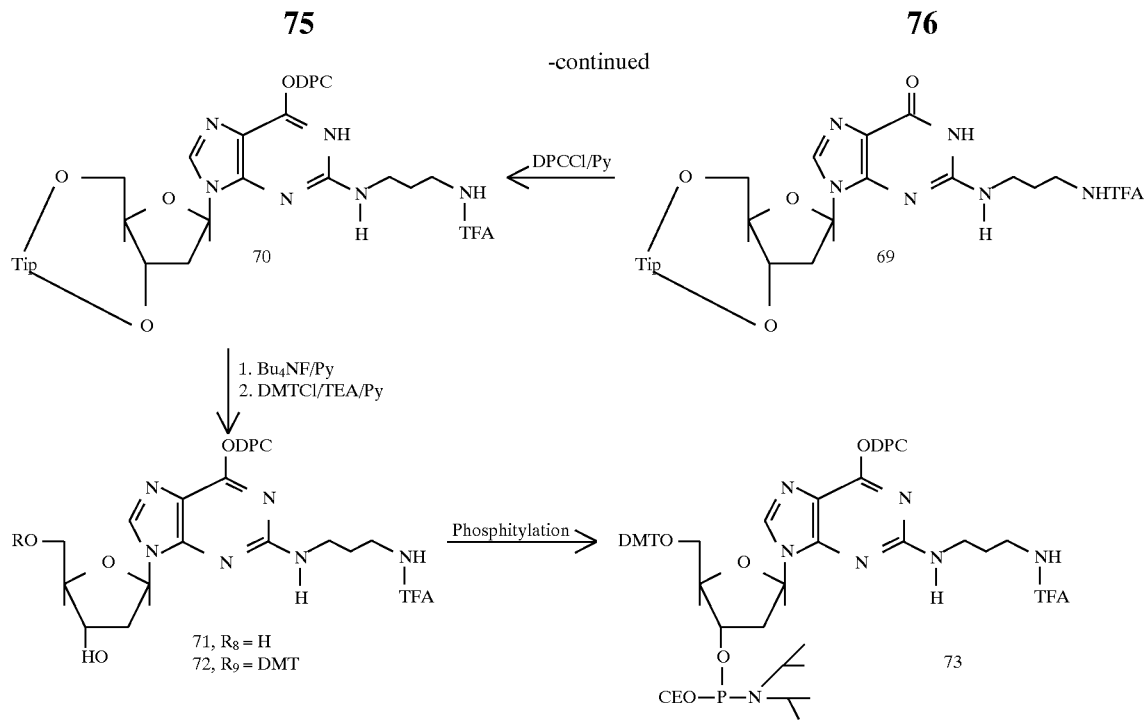

EXAMPLE 70

3',5'-O-(Tetraisopropyldisiloxane-1,3-diyl)-N$_2$-(6-trifluoroacetamido-hexyl)-9-(2'-deoxy-β-D-erythro-pentofuranosyl)guanosine. (74)

To a stirred solution of 1,6-hexanediamine (3.30 g, 28.50 mmol) in 2-methoxyethanol (30 mL) at 90° C. was added a solution of 3',5'-O-tetraisopropyldisiloxane-1,3-diyl-2-choloro-9-(2'-deoxy-β-D-erythro-pentofuranosyl)inosine (5.00 g, 9.45 mmol) (36) in 2-methoxyethanol (40 mL) over 4 h period. The reaction mixture was stirred at 90° C. for 12 h. The reaction was evaporated to dryness and the residue was coevaporated with dry pyridine (3×150 mL).

The resulting brown foam was dissolved in dry MeOH (30 mL) and allowed to stir at room temperature. To this stirred solution was added triethylamine (6.07 g, 60 mmol) followed by ethyltrifluoroacetate (13.51 g, 95 mmol) under argon atmosphere. The reaction mixture was stirred at room temperature overnight. The solvent was removed to an oil and purified by flash chromatography over silica gel using CH$_2$Cl$_2$→acetone as the eluent. The pure fractions were collected and evaporated to give a brownish yellow solid: mp; yield 3.04 g (47%); $^1$H NMR (CDCl$_3$) δ1.00 (m, 28H), 1.32 (m, 4H, 2CH$_2$), 1.54 (m, 4H, 2CH$_2$), 2.62 (m, 2H, C$_2$,H), 3.32 (m, 4H, 2CH$_2$), 3.84 (m, 3H, C$_5$,CH$_2$ C$_4$,H), 4.72 (q, 1H, C$_3$,H), 6.18 (t, 1H, J$_{1',2'}$=6.20 Hz, C$_1$,H), 7.12 (bs, 1H, NH), 7.72 (s, 1H, C$_8$H). Anal. Calcd for C$_{30}$H$_{51}$F$_3$N$_6$O$_6$Si$_2$: C, 51.11; H, 7.29; N, 11.92. Found: C, 51.02; H, 6.99; N, 11.70.

EXAMPLE 71

3',5'-O-(Tetraisopropyldisiloxane-1,3-diyl)-6-O-diphenylcarbamoyl-N$_2$-(6-trifluoroacetamidohexyl)-9-(2-deoxy-β-D-erythro-pentofuranosyl)-guanosine. (75)

To a well dried solution of the substrate 74 (5.65 g, 8.30 mmol) in dry pyridine (200 mL) was added N,N-diisopropylethylamine (2.15 g, 16.60 mmol) followed by diphenylcarbamoyl chloride (3.85 g, 16.6 mmol) at once. After the addition of DPCCl, the reaction mixture was stirred at room temperature for 2 h and evaporated to dryness. The residue was dissolved in CH$_2$Cl$_2$ (150 mL) and washed with 5% NaHCO$_3$ solution (50 mL), water (50 mL) and brine (50 mL). The CH$_2$Cl$_2$ extract was dried over anhydrous MgSO$_4$ and evaporated to dryness. The residue was purified by flash chromatography over silica gel using CH$_2$Cl$_2$→→acetone as the eluent. The pure fractions were collected and evaporated to give 6.04 g (81%) as brownish foam: $^1$H NMR (CDCl$_3$) δ1.00 (m, 28H), 1.32 (m, 4H, 2CH$_2$), 1.54 (m, 4H, 2CH$_2$), 2.62 (m, 2H, C$_2$,H), 3.25 (m, 2H, CH$_2$), 3.42 (m, 2H, CH$_2$), 3.92 (m, 3H, C$_5$,CH$_2$ C$_4$,H), 4.74 (q, 1H, C$_3$,H), 6.20 (t, 1H, J$_{1',2'}$=6.20 Hz, C$_1$,H), 6.50 (bs, 1H, NH), 7.35 (m, 10H, ArH), 7.85 (s, 1H, C$_8$H). Anal. Calcd for C$_{43}$H$_{60}$F$_3$N$_7$O$_7$Si$_2$: C, 57.37; H, 6.72; N, 10.89. Found: C, 57.17; H, 6.42; N, 10.77.

EXAMPLE 72

6-O-Diphenylcarbamoyl-N$_2$-(6-trifluoroacetamidohexyl)-9-(2-deoxy-β-D-erythro-pentofuranosyl)guanosine. (76)

The substrate 75 (6.00 g, 6.67 mmol) was dissolved in dry pyridine (50 mL) and allowed to stir at room temperature. To this stirred solution was added 0.5M tetrabutylammonium fluoride (70 mL, 35 mmol, prepared in py:THF:H$_2$O; 5:4:1) at once. The reaction mixture was stirred at room temperature for 15 min, the pH was adjusted to 7 with H$^+$ resin. The reaction was filtered, washed with methanol (50 mL) and the filtrate evaporated to dryness. The residue was dissolved in CH$_2$Cl$_2$ (150 mL), washed with water (50 mL) and brine (50 mL). The organic extract was dried over anhydrous MgSO$_4$ and evaporated to dryness. The residue was purified by flash chromatography over silica gel using CH$_2$Cl$_2$→MeOH as the eluent. The pure fractions having the pure product was collected and evaporated to give 3.77 g (86%) as foam: $^1$H NMR (CDCl$_3$) δ1.32 (m, 4H, 2CH$_2$), 1.54 (m, 4H, 2CH$_2$), 2.22 (m, 1H, C$_2$,H), 2.92 (m, 1H, C$_2$,H), 3.25 (q, 2H, CH$_2$), 3.40 (q, 2H, CH$_2$), 3.82 (m, 3H, C$_5$·CH$_2$, C$_4$·H), 4.12 (s, 1H, C$_3$·H), 4.62 (s, 1H, C$_3$·OH), 5.22 (t, 1H, C$_5$·OH), 6.20 (t, 1H, J$_{1',2'}$=6.20 Hz, C$_1$·H), 6.80 (bs, 1H, NH), 7.35 (m, 10H, ArH), 7.74 (s, 1H, C$_8$H). Anal. Calcd for C$_{31}$H$_{34}$F$_3$N$_7$O$_6$Si: C, 56.61; H, 5.21; N, 14.91. Found: C, 56.55; H, 5.31; N, 15.09.

EXAMPLE 73

5'-O-(4,4'-Dimethoxytrityl)-6-O-diphenylcarbamoyl-N$_2$-(6-trifluoro-acetamidohexyl)-9-(2-deoxy-β-D-erythro-pentofuranosyl)guanosine. (77)

The substrate 76 (3.77 g, 5.73 mmol) was dissolved in dry pyridine (30 mL) and evaporated to dryness. The dried 76 was dissolved in dry pyridine (100 mL) and treated with triethylamine (1.19 g, 11.84 mmol) followed by 4,4'-dimethoxytrityl chloride (4.02 g, 11.84 mmol) under argon atmosphere. The reaction mixture stirred at room temperature overnight and was quenched with methanol (20 mL). The stirring was continued for 10 min and evaporated to dryness. The residue was dissolved in dichloromethane (150 mL), washed with 5% NaHCO$_3$ solution (40 mL), water (40 mL) and brine (50 mL). The organic extract was dried over anhydrous MgSO$_4$ and the solvent was removed under reduced pressure. The residue was purified by flash chromatography over silica gel using CH$_2$Cl$_2$→acetone as the eluent. The main fractions were collected and evaporated to dryness to give 6.0 g (72%) of the titled compound. $^1$H NMR (CDCl$_3$) δ1.32 (m, 4H, 2CH$_2$), 1.54 (m, 4H, 2CH$_2$), 2.22 (m, 1H, C$_2$·H), 2.72 (m, 1H, C$_2$·H), 3.30 (m, 4H, 2CH$_2$), 3.73 (s, 6H, 2 OCH$_3$), 4.02 (m, 3H, C$_5$·CH$_2$, C$_4$·H), 4.62 (m, 1H, C$_3$·H), 5.02 (m, 1H, C$_3$·OH), 6.30 (t, 1H, J$_{1',2'}$=6.20 Hz, C$_1$·H), 6.60 (bs, 1H, NH), 6.80 (d, 4H, ArH), 7.30 (m, 19H, ArH), 7.78 (s, 1H, C$_8$H).

EXAMPLE 74

3'-O-[(N,N-diisopropylamino) (β-cyanoethoxy) phosphanyl]-5'-O-(4,4'-dimethoxytrityl)-6-O-diphenylcarbamoyl-N$_2$-(6-trifluoroacetamidohexyl)-9-(2-deoxy-β-D-erythro-pentofuranosyl) guanosine. (78)

The substrate 77 (1.56 g, 1.62 mmol) was dissolved in dry pyridine (30 mL) and evaporated to dryness. This was repeated three times to remove last traces of water and dried over solid sodium hydroxide overnight. The dried 77 was dissolved in dry dichloromethane (50 mL) and cooled to 0° C. under argon atmosphere. To this cold stirred solution was added N,N-diisopropylethylamine (0.42 g, 3.24 mmol) followed by (β-cyanoethoxy)chloro(N,N-diisopropylamino) phosphane (0.76 g, 3.24 mmol) dropwise over a period of 10 min. The reaction mixture was stirred at 0° C. for 1 h and at room temperature for 2 h. The reaction mixture was diluted with dichloromethane (100 mL), washed with 5% NaHCO$_3$ solution (50 mL), water (50 mL) and brine (50 mL). The organic extract was dried over anhydrous MgSO$_4$ and the solvent was removed under reduced pressure. The residue was purified by flash chromatography over silica gel using CH$_2$Cl$_2$→EtOAc containing 1% triethylamine as the eluent. The main fractions were collected and evaporated to dryness. The residue was dissolved in dry dichloromethane (10 mL) and added dropwise into a stirred solution of hexane (1000 mL), during 30 min. After the addition, the stirring was continued for additional 1 h at room temperature under argon. The precipitated solid was filtered, washed with hexane and dried over solid NaOH under vacuum overnight to give 1.35 g (73%) of the titled compound as colorless powder.

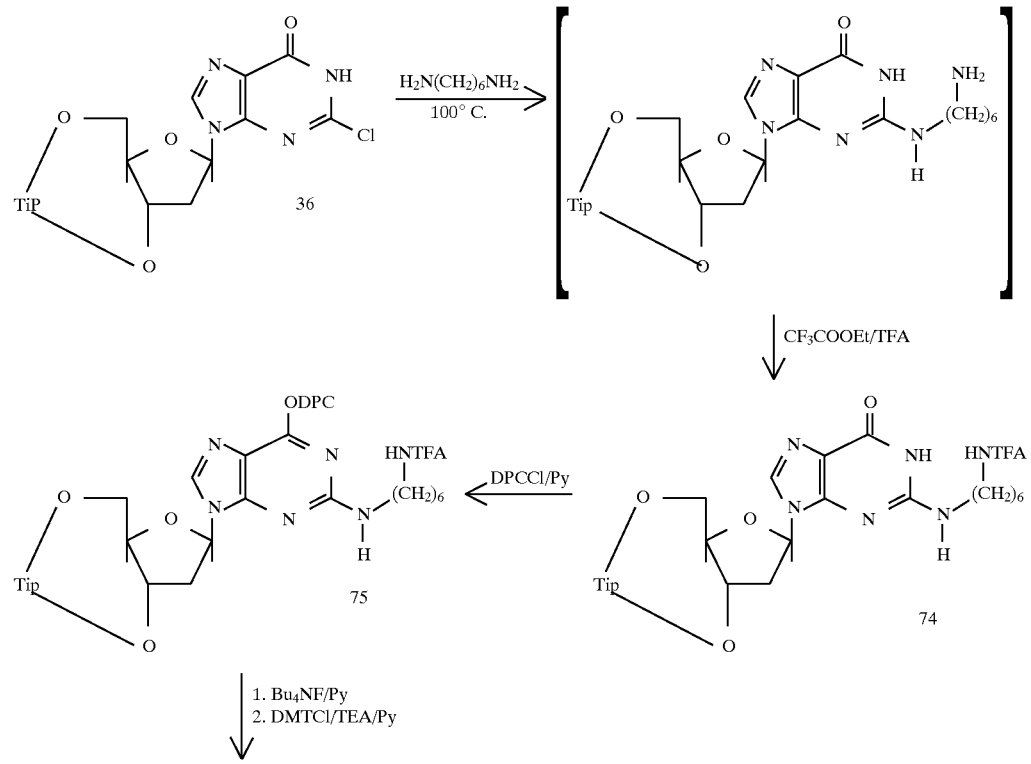

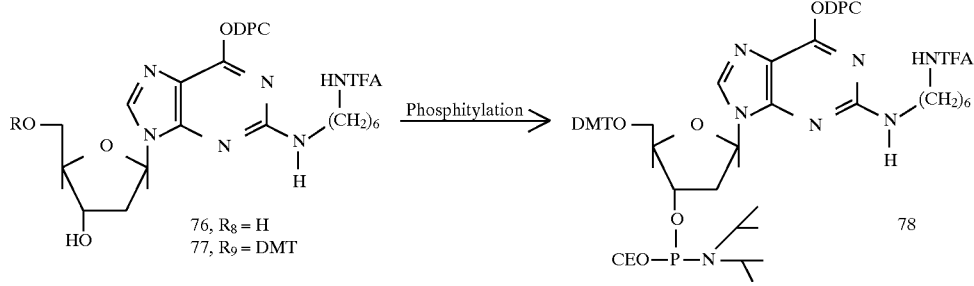

EXAMPLE 75
Standard Oligonucleotide Synthesis

Oligonucleotide syntheses were performed on an Applied Biosystems 380 B or 394 DNA synthesizer following standard phosphoramidite protocols and cycles using reagents supplied by the manufacturer. When modified phosphoramidites are used, a longer coupling time (10–15 min) was employed. The oligonucleotides were normally synthesized in either a 10 μmol scale or a 3×1 μmol scale in the "Trityl-On" mode. Standard deprotection conditions (30% $NH_4OH$, 55° C., 16 hr) were employed. HPLC was performed on a Waters 600E instrument equipped with a model 991 detector. For analytical chromatography, the following reverse phase HPLC conditions were employed: Waters C-18 column (25×3.5 cm); solvent A: 50 mm TEAA, pH 7.0; solvent B: 100% $CH_3CN$; flow rate: 1.5 ml/min; gradient: 5% B for the first 5 minutes, linear (1%) increase in B every minute thereafter. For preparative purposes, the following reverse phase HPLC conditions were employed: Waters Delta-Pak $C_4$ 15 μm, 300A, 25×100 mm column equipped with a guard column of the same material; column flow rate: 5 ml/min; gradient: 5% B for the first 10 minutes, linear 1% increase for every minute thereafter. Following HPLC purification, oligonucleotides are detritylated and further purified by size exclusion using a Sephadex G-25 column. All oligonucleotide sequences are listed in a standard 5' to 3' order from left to right.

Enzymatic degradation and subsequent HPLC analysis indicated the expected ratios of the nucleoside components. Oligonucleotides were digested with a mixture of spleen phosphodiesterase, snake venom phosphodiesterase, and bacterial alkaline phosphatase to provide individual nucleosides which were analyzed by HPLC.

EXAMPLE 76
Purine Oligonucleotides with $N_2$-Propyl Amine Tethers

The phosphoramidite compound, 5'-dimethoxytrityl-$N_2$-(-N-trifluoroacetylpropylamino)-2'-deoxyguonosine-3'-O-(2-cyanoethyl-N,N-diisopropyl)phosphoramidite, was utilized in the DNA synthesizer as a 0.2M solution in anhydrous $CH_3CN$. Oligonucleotide synthesis was carried out in either an ABI 380B or an ABI 394 synthesizer employing the standard synthesis cycles with an extended coupling time of 10 to 15 minutes during coupling of the modified amidite into the oligonucleotide sequence. Coupling efficiency of greater than 90% was observed.

A. Phosphodiester Oligonucleotides with $N_2$-Propyl Amine Tethers

The following oligonucleotides having phosphodiester inter-nucleotide linkages were synthesized:

oligomer 1: (SEQ ID NO:1):
  5' GAG*CT3';
Oligomer 2: (SEQ ID NO:2):
  5' TG*G GAG CCA TAG CGA GGC 3' (ICAM-1; P=O);
Oligomer 3: (SEQ ID NO:2):
  5' TG*G GAG CCA TAG* CGA GGC 3' (ICAM-1; P=O);

wherein G* represents a nucleotide functionalized to incorporate a $N_2$-propylamino functionality. Oligomers 2 and 3 are antisense compounds targeted against the human ICAM-1 (Inter Cellular Adhesion Molecule-1). The oligonucleotides were synthesized in either a 10 mmol scale or a 3×1 mmol scale in the "Trityl-On" mode. Standard deprotection conditions (30% $NH_4OH$, 55° C., 24 hours) were employed. The oligonucleotides were purified by reverse phase HPLC (Waters Delta-Pak $C_4$ 15 m, 300A, 25×100 mm column equipped with a guard column of the same material). They were detritylated and further purified by size exclusion using a Sephadex G-25 column. NMR analyses by both proton and phosphorus NMR confirmed the expected structure for Oligomer 1.

B. $N_2$-propylamine Linking Group Containing Phosphorothioate Oligonucleotide The following oligonucleotide having phosphorothioate inter-nucleotide linkages was synthesized:

Oligomer 4: (SEQ ID NO:3):
  5' TsG*sGs GsAsGs CsCsAs TsAsGs CsGsAs GsGsC 3' (ICAM-1; P=S);

Where G* represents a nucleotide functionalized to incorporate a $N_2$-propylamine functionality and the subscript "s" represents a phosphorothioate internucleotide backbone linkage. Oligomer 4 is an antisense compound to ICAM and it has the same sequence as Oligomer 4 in PCT Application WO 93/07883 except for the purine modification. These oligonucleotides were synthesized as per the method of Example 76(a) except during the synthesis, for oxidation of the phosphite moieties, the Beaucage reagent (i.e., 3H-1,2-benzodithioate-3-one 1,1-dioxide, see, Iyer,R. P., et al., *J. Am. Chem. Soc.* 1990, 112, 1253) was used as a 0.24M solution in anhydrous $CH_3CN$ solvent. The oligonucleotides were synthesized in the "Trityl-On" mode and purified by reverse phase HPLC utilizing the purification procedure of Example 75.

C. 2'-O-Methyl Derivatized, $N_2$-propylamine Linking Group Containing RNA Oligonucleotides The following oligonucleotides having 2'-O-methyl groups on each nucleotide not functionalized with a $N_2$-propylamine functionalization were synthesized:

Oligomer 5: (SEQ ID NO:4):
   GGAGAUCUGAG*C;
Oligomer 6: (SEQ ID NO:5):
   G*CUCUCUC;
Oligomer 7: (SEQ ID NO:6):
   CGAGAUCUGAG*C;

wherein G* represents a nucleotide functionalized to incorporate a $N_2$-propylamine functionality and where the remaining nucleotides are each 2'-O-methyl derivatized nucleotides. Both Oligomers 6 and 7 are sequences in the HIV-1 TAR region. The oligonucleotides were synthesized as per the method of Example 76(A) and appropriate 2'-O-methyl phosphoramidite nucleotides from Chemgenes Inc. (Needham, Mass.) were used for the remaining RNA nucleotides. The oligonucleotides were deprotected and purified as per the method of Example 76(A).

TABLE I

HPLC retention times of $N_2$-propylamine oligonucleotides

| Oligo-nucleo-tide | Type | Prep. retn. time | Anal. retn. time |
|---|---|---|---|
| 1 | P=O | 40.50 | 21.98 |
| 2 | P=O | 34.44 | 23.32 |
| 3 | P=O | 32.43 | 23.09 |
| 4 | P=S | 39.68 | 30.82 |
| 5 | P=O, 2'-OMe | 46.86 | 25.26 |
| 6 | P=O, 2'-OMe | 47.28 | 27.76 |
| 7 | P=O, 2'-OMe | 48.27 | 28.30 |

HPLC experimental conditions are as follows:
Waters 600E with 991 detector; Waters C-18 (25×3.5 cm); Solvent A: 50 mM TEAA, pH 7.0; B: 100% Acetonitrile; 1.5 ml/min. flow rate; Gradient: 5% B for first 5 minutes, linear increase in B to 40% during next 55 minutes.

EXAMPLE 77

Functionalizationo of Oligonucleotides At the $N_2$-Position

A. Functionalization with Biotin Reagent Preparation

D-Biotin-aminocaproyl-N-hydroxysuccinimide ester (7.5 mg, 21.6 mmols) (Sigma, St. Louis, Mo.) was dissolved in 300 microliters of anhydrous DMF by vortexing in a microfuge tube.

1. Single Site Modification

About 10 O.D. units ($A_{260}$) of Oligomer 2 (see, Example 76) (approximately 60 nmols based on the calculated extinction coefficient of $1.6756 \times 10^5$) was dried in a microfuge tube. The oligonucleotide was dissolved in 200 μl of 0.2M $NaHCO_3$ buffer and the above solution of D-biotin-aminocaproyl-N-hydroxysuccinimide ester (2.5 mg, 7.3 μmols in 100 μl) (Sigma, St. Louis, Mo.) was added. The solution was let stand overnight. The solution was applied to a Sephadex G-25 column (0.7×15 cm) and the oligonucleotide fractions were combined. Analytical HPLC showed nearly 85% conversion to the product. The product was purified by HPLC and further desalted on Sephadex G-25 to give the oligonucleotide:

Oligomer 8: (SEQ ID NO:2):
   5' TG*G GAG CCA TAG CGA GGC 3';

wherein G* represents a nucleotide functionalized to incorporate a biotin functionality linked via a $N_2$-propylamino linking group to the $N_2$-position of the designated nucleotide. HPLC retention times are shown in Table II below.

2. Multiple Site Modification

About 10 O.D. units ($A_{260}$) of Oligomer 3 (see, Example 76, approximately 60 nmols) was treated utilizing the method of Example 8(A)(1) in PCT Application WO 93/07883 with the above solution of D-biotin-aminocaproyl-N-hydroxysuccinimide ester (5 mg in 200 μl DMF) in 300 μl of 0.2M $NaHCO_3$ buffer. Analytical HPLC showed 60% of double labeled oligonucleotide product and 30% of single labeled products (from the two available reactive sites). HPLC and Sephadex G-25 purification gave the oligonucleotide:

Oligomer 9: (SEQ ID NO:2):
   5' TG*G GAG CCA TAG* CGA GGC 3';

wherein G* represents a nucleotide functionalized to incorporate a biotin functionality linked via a $N_2$-propylamino linking group to the $N_2$-position of the designated nucleotide. HPLC retention times for this product (and its accompanying singly labeled products) are shown in Table II below.

B. Functionalization with Fluorescein Reagent Preparation

A 6 mg portion of fluorescein-isothiocyanate in 300 μl DMF was added to give a 0.05M solution. (6.0 mg, 15 μmols) (Sigma, St. Louis, Mo.) was dissolved in 300 microliters of anhydrous DMF by vortexing in a microfuge tube.

1. Single Site Modification

A 1M $Na_2CO_3$/1M $NaHCO_3$ buffer (pH 9.0) was prepared by adding 1M $NaHCO_3$ to 1M $Na_2CO_3$. A 200 μl portion of this buffer was added to 10 O.D. units of Oligomer 2 (see, Example 76) in a microfuge tube. A 100 μl portion of the fluorescein solution was added to the oligonucleotide solution in the microfuge tube. The tube was covered with aluminum foil and let stand overnight. The reaction mixture was applied to a Sephadex G-25 column (0.7×20 cm) that had been equilibrated with 25% (v/v) ethyl alcohol in water. The column was eluted with the same solvent. Product migration could be seen as a yellow band well separated from dark yellow band of the excess fluorescein reagent. The fractions showing absorption at both 260 nm and 485 nm were combined and purified by HPLC as per the purification procedure of Example 77(A)(1). Analytical HPLC indicated nearly 85% of the desired doubly functionalized oligonucleotide. The product was lyophilized and desalted on Sephadex to give the oligonucleotide:

Oligomer 10: (SEQ ID NO:2):
   5' TG*G GAG CCA TAG CGA GGC 3';

wherein G* represents a nucleotide functionalized to incorporate a fluorescein functionality linked via a $N_2$-propylamino linking group to the $N_2$-position of the designated nucleotide. HPLC retention times are shown in Table II below.

2. Multiple Site Modification

A 10 O.D. unit ($A_{260}$) portion of Oligomer 3 (from Example 76) was dissolved in 300 μl of the 1M $Na_2HCO_3$/1M $Na_2CO_3$ buffer of Example 77(B)(1) and 200 μl of the fluoresceinisothiocyanate stock solution of Example 77(B)(1) was added. The resulting solution was treated as per Example 77(B)(1). Analytical HPLC indicated 62% of doubly labeled product and 30% of singly labeled products. Work up of the reaction gave the oligonucleotide:

Oligomer 11: (SEQ ID NO:2):
   5' TG*G GAG CCA TAG* CGA GGC 3';

wherein G* represents nucleotides functionalized to incorporate a fluorescein functionality linked via a $N_2$-propylamino linking group to the $N_2$-position of the designated nucleotide. HPLC retention times are shown in Table II below.

C. Functionalization with Rhodamine
Reagent Preparation

A 6 mg portion of rhodamine isothiocyanate in 300 µl DMF was added to give a 0.04M solution. (6.0 mg, 10 µmols) (Molecular Probes, Eugene, Oreg.) was dissolved in 300 microliters of anhydrous DMF by vortexing in a microfuge tube.

1. Single Site Modification

A 1M $Na_2CO_3$/1M $NaHCO_3$ buffer (pH 9.0) was prepared by adding 1M $NaHCO_3$ to 1M $Na_2CO_3$. A 200 µl portion of this buffer was added to 10 O.D. units of Oligomer 2 (see, Example 76) in a microfuge tube. A 100 µl portion of the rhodamine solution was added to the oligonucleotide solution in the microfuge tube. The tube was covered with aluminum foil and let stand overnight. The reaction mixture was applied to a Sephadex G-25 column (0.7×20 cm) that had been equilibrated with 25% (v/v) ethyl alcohol in water. The column was eluted with the same solvent. Product migration could be seen as a yellow band well separated from dark yellow band of the excess Rhodamine reagent. The fractions showing absorption at both 260 nm and 565 nm were combined and purified by HPLC as per the purification procedure of Example 77(A)(1). Analytical HPLC indicated nearly 90% of the desired doubly functionalized oligonucleotide. The product was lyophilized and desalted on Sephadex to give the oligonucleotide:

Oligomer 12: (SEQ ID NO:2):
5' TG*G GAG CCA TAG CGA GGC 3';
wherein G* represents a nucleotide functionalized to incorporate a rhodamine functionality linked via a $N_2$-propylamino linking group to the $N_2$-position of the designated nucleotide. HPLC retention times are shown in Table II below.

2. Multiple Site Modification

A 10 O.D. unit ($A_{260}$) portion of Oligomer 3 (see, Example 76) was dissolved in 300 µl of the 1M $NaHCO_3$/1M $Na_2CO_3$ buffer of Example 77(B)(1) and 200 µl of the rhodamine-isothiocyanate stock solution of Example 77(C) was added. The resulting solution was treated as per Example 77(B)(1). Analytical HPLC indicated 70% of doubly labeled product and 25% of singly labeled products. Work up of the reaction gave the oligonucleotide:

Oligomer 13: (SEQ ID NO:2)
5' TG*G GAG CCA TAG* CGA GGC 3';
wherein G* represents a nucleotide functionalized to incorporate a rhodamine functionality linked via a $N_2$-propylamino linking group to the $N_2$-position of the designated nucleotide. HPLC retention times are shown in Table II below.

D. Functionalization with Cholic Acid Reagent Preparation

Cholic acid-N-hydroxysuccinimide ester, (prepared as per the disclosure for Compound 1 in PCT Application WO 93/07883, 15 mg, 29.7 µmols) was dissolved in 300 microliters of anhydrous DMF by vortexing in a microfuge tube.

1. Single Site Modification

A 10 O.D. unit ($A_{260}$) portion of Oligomer 2 (see, Example 76) dissolved in 200 µl of 0.2M $NaHCO_3$ buffer was treated with 5 mg cholic acid-NHS ester 100 µl DMF. The reaction mixture was heated for 16 hours at 37° C. The product was isolated as per the method of Example 77(A)(1). Analytical HPLC indicated greater than 90% product formation. Work up of the reaction gave the oligonucleotide:

Oligomer 14: (SEQ ID NO:2):
5' TG*G GAG CCA TAG CGA GGC 3';
wherein G* represents a nucleotide functionalized to incorporate a cholic acid functionality linked via a $N_2$-propylamino linking group to the $N_2$-position of the designated nucleotide. HPLC retention times are shown in Table II below.

2. Multiple Site Modification

A 10 O.D. unit ($A_{260}$) portion of Oligomer 3 (see, Example 76) dissolved in 300 µl of 0.2M $NaHCO_3$ buffer was treated with cholic acid-NHS ester (prepared as per the disclosure for Compound 1 in PCT Application WO 93/07883, 10 mg, 19.8 µmols)in 200 µl DMF. The reaction mixture was heated for 16 hours at 37° C. The product was isolated as per the method of Example 77(A)(1). Analytical HPLC revealed 68% doubly labeled product, 17% of a first singly labeled product and 24% of a second singly labeled product. Work up as per Example 77(A)(1) gave the oligonucleotide:

oligomer 15: (SEQ ID NO:2):
5' TG*G GAG CCA TAG* CGA GGC 3';
wherein G* represents nucleotides functionalized to incorporate a cholic acid functionality linked via a $N_2$-propylamino linking group to the $N_2$-position of the designated nucleotide. HPLC retention times are shown in Table II below.

E. Functionalization with Cholesterol hemisuccinate Reagent Preparation

Cholesterol-hemisuccinate N-hydroxysuccinimide ester, (prepared as per the disclosure for Compound 1 in PCT Application WO 93/07883, 15 mg, 30 µmols) was dissolved in 300 microliters of anhydrous DMF by vortexing in a microfuge tube.

1. Single Site Modification

A 10 O.D. unit ($A_{260}$) portion of Oligomer 2 (see, Example 76) in 200 µl of 0.1M borate pH 8.3 buffer is treated with cholesterol-hemisuccinate N-hydroxy succinimide ester 5 mg in 100 µl DMF. The reaction mixture is let stand overnight at 37° C. The product is isolated as per the method of Example 77(A)(1). Work up of the reaction gave the oligonucleotide:

Oligomer 16: (SEQ ID NO:2):
5' TG*G GAG CCA TAG CGA GGC 3';
wherein G* represents a nucleotide functionalized to incorporate a cholesterol functionality linked via a $N_2$-propylamino linking group to the $N_2$-position of the designated nucleotide.

2. Multiple Site Modification

A 10 O.D. units ($A_{260}$) portion of Oligomer 3 (see, Example 76) in 300 µl of 1.0M borate pH 8.3 buffer was treated with cholesterol-hemisuccinate N-hydroxy succinimide ester 10 mg in 200 µl DMF. The reaction mixture is let stand overnight at 37° C. The product is isolated as per the method of Example 77(A)(1). Work up as per Example 77(A)(1) gave the oligonucleotide:

Oligomer 17: (SEQ ID NO:2):
5' TG*G GAG CCA TAG* CGA GGC 3';
wherein G* represents nucleotides functionalized to incorporate a cholesterol functionality linked via a $N_2$-propylamino linking group to the $N_2$-position of the designated nucleotide. HPLC retention times are shown in Table II below.

F. Functionalization with Pyrene Reagent Preparation

Pyrene-1-butyric acid-N-hydroxysuccinimide ester (15 mg, 50 µmols) (Molecular Probes, Eugene, Oreg.) was dissolved in 300 microliters of anhydrous DMF by vortexing in a microfuge tube.

1. Single Site Modification

About 10 O.D. units ($A_{260}$) of Oligomer 2 (see, Example 76) (approximately 60 nmols based on the calculated extinction coefficient of $1.6756 \times 10^5$) was dried in a microfuge tube. The oligonucleotide was dissolved in 200 µl of 0.2M NaHCO$_3$ buffer and the above solution of pyrene-1-butyric acid-N-hydroxysuccinimide ester (2.5 mg, 7.3 µmols in 100 mL) was added. The solution was let stand overnight. The solution was applied to a Sephadex G-25 column (0.7×15 cm) and the oligonucleotide fractions were combined. Analytical HPLC showed nearly 95% conversion to the product. The product was purified by HPLC and further desalted on Sephadex G-25 to give the oligonucleotide:

Oligomer 18: (SEQ ID NO:2):
5' TG*G GAG CCA TAG CGA GGC 3';

wherein G* represents a nucleotide functionalized to incorporate a pyrene functionality linked via a N$_2$-propylamino linking group to the N$_2$-position of the designated nucleotide. HPLC retention times are shown in Table II below.

2. Multiple Site Modification

About 10 O.D. units ($A_{260}$) of Oligomer 3 (see, Example 76, approximately 60 nmols) was treated utilizing the method of Example 8(A)(1) in PCT Application WO 93/07883, with the above solution of pyrene-1-butyric acid-N-hydroxysuccinimide ester (5 mg in 200 µl DMF) in 300 µl of 0.2M NaHCO$_3$ buffer. Analytical HPLC showed 80% of double labeled oligonucleotide product and 15% of single labeled products (from the two available reactive sites). HPLC and Sephadex G-25 purification gave the oligonucleotide:

Oligomer 19: (SEQ ID NO:2):
5' TG*G GAG CCA TAG* CGA GGC 3';

wherein G* represents nucleotides functionalized to incorporate a pyrene functionality linked via a N$_2$-propylamino linking group to the N$_2$-position of the designated nucleotide. HPLC retention times for this product (and its accompanying singly labeled products) are shown in Table II below.

G. Functionalization with Aromatic azide Reagent Preparation (4-azido-6-nitro-1-aminocaproyl)-phenyl-N-hydroxysuccinimide ester (7.5 mg, 75 µmols) (Sigma, St. Louis, Mo.) was dissolved in 300 microliters of anhydrous DMF by vortexing in a microfuge tube.

1. Single Site Modification

About 10 O.D. units ($A_{260}$) of Oligomer 2 (see, Example 76) (approximately 60 nmols based on the calculated extinction coefficient of $1.6756 \times 10^5$) was dried in a microfuge tube. The oligonucleotide was dissolved in 200 µl of 0.2M NaHCO$_3$ buffer and the above solution of (4-azido-6-nitro-1-aminocaproyl)-phenyl-N-hydroxysuccinimide ester (2.5 mg, 25 µmols in 100 mL) (Sigma, St. Louis, Mo.) was added. The solution was let stand overnight. The solution was applied to a Sephadex G-25 column (0.7×15 cm) and the oligonucleotide fractions were combined. Analytical HPLC showed nearly 90% conversion to the product. The product was purified by HPLC and further desalted on Sephadex G-25 to give the oligonucleotide:

Oligomer 20: (SEQ ID NO:2):
5' TG*G GAG CCA TAG CGA GGC 3';

wherein G* represents a nucleotide functionalized to incorporate an aromatic azide functionality linked via a N$_2$-propylamino linking group to the N$_2$-position of the designated nucleotide. HPLC retention times are shown in Table II below.

2. Multiple Site Modification

About 10 O.D. units ($A_{260}$) of Oligomer 3 (see, Example 76, approximately 60 nmols) was treated utilizing the method of Example 8(A)(1) in PCT Application WO 93/07883 with the above solution of (4-azido-6-nitro-1-aminocaproyl)-phenyl-N-hydroxysuccinimide ester (5 mg in 200 µl DMF) in 300 µl of 0.2M NaHCO$_3$ buffer. Analytical HPLC showed 70% of double labeled oligonucleotide product and 20% of single labeled products (from the two available reactive sites). HPLC and Sephadex G-25 purification gave the oligonucleotide:

Oligomer 21: (SEQ ID NO:2):
5' TG*G GAG CCA TAG* CGA GGC 3';

wherein G* represents nucleotides functionalized to incorporate a aromatic azide functionality linked via a N$_2$-propylamino linking group to the N$_2$-position of the designated nucleotide. HPLC retention times for this product (and its accompanying singly labeled products) are shown in Table II below.

H. Functionalization with Bromoacetyl alkylator Reagent Preparation

Bromoacetic acid N-hydroxysuccinimide ester (15 mg, 75 µmols) was dissolved in 300 microliters of anhydrous DMF by vortexing in a microfuge tube.

1. Single Site Modification

About 10 O.D. units ($A_{260}$) of Oligomer 2 (see, Example 76) (approximately 60 nmols based on the calculated extinction coefficient of $1.6756 \times 10^5$) was dried in a microfuge tube. The oligonucleotide was dissolved in 200 µl of 0.2M NaHCO$_3$ buffer and the above solution of bromoacetic acid N-hydroxysuccinimide ester (5.0 mg, 25 µmols in 100 µL) was added. The solution was let stand overnight. The solution was applied to a Sephadex G-25 column (0.7×15 cm) and the oligonucleotide fractions were combined. Analytical HPLC showed nearly 88% conversion to the product. The product was purified by HPLC and further desalted on Sephadex G-25 to give the oligonucleotide:

Oligomer 22: (SEQ ID NO:2):
5' TG*G GAG CCA TAG CGA GGC 3';

wherein G* represents a nucleotide functionalized to incorporate a bromoacetyl alkylator functionality linked via a N$_2$-propylamino linking group to the N$_2$-position of the designated nucleotide. HPLC retention times are shown in Table II below.

2. Multiple Site Modification

About 10 O.D. units ($A_{260}$) of Oligomer 3 (see, Example 76, approximately 60 nmols) was treated with the above solution of bromoacetic acid N-hydroxysuccinimide ester (10 mg in 200 µl DMF) in 300 µl of 0.2M NaHCO$_3$ buffer. Analytical HPLC showed 75% of double labeled oligonucleotide product and 20% of single labeled products (from the two available reactive sites). HPLC and Sephadex G-25 purification gave the oligonucleotide:

Oligomer 23: (SEQ ID NO:2):
5' TG*G GAG CCA TAG* CGA GGC 3';

wherein G* represents nucleotides functionalized to incorporate a bromoacetyl alkylator functionality linked via a $N_2$-propylamino linking group to the $N_2$-position of the designated nucleotide. HPLC retention times for this product (and its accompanying singly labeled products) are shown in Table II below.

TABLE II

HPLC Retention times of Oligos 2 (SEQ ID NO:2) and (SEQ ID NO: 2) with various Functionalities[a]
Retention Time (min.)
(Multiple Substitution) III

| Oligomer | Single substitution | Mono conjugated (Minor product) | Di conjugated (Major Product) |
|---|---|---|---|
| Oligomer 2[1] | 23.32 | | |
| Oligomer 3[1] | | 23.09 | |
| Oligomer 8[2] | 28.22 | | |
| Oligomer 9[2] | | 28.56[a] | 29.01[b] |
| Oligomer 10[4] | 29.97 | | |
| Oligomer 11[4] | | 26.12[a] | 29.73 27.60[a] |
| Oligomer 12[5] | 32.06 | | |
| Oligomer 13[5] | | 32.19 | 33.78[b] |
| Oligomer 14[3] | 39.08 | | |
| Oligomer 15[3] | | 35.90 | 42.89[b] 38.99[a] |
| Oligomer 18[6] | 35.46 | | |
| Oligomer 19[6] | | 36.00[a] | 38.13[b] |
| Oligomer 20[6] | 33.41 | | |
| Oligomer 21[6] | | 33.37[a] | 35.23[b] |
| Oligomer 22[7] | 25.19 | | |
| Oligomer 23[7] | | 25.24 | 26.16[b] |

Conditions: Waters 600E with 991 detector; Waters C-18 (25 × 3.5 cm); Solvent A: 50 mM TEAA, pH 7.0; B: 100% acetonitrile; 1.5 ml/min. flow rate; Gradient: 5% B for first 5 minutes, linear increase in B to 40% during next 55 minutes.
[a]Mono conjugated minor product;
[b]Doubly conjugated major product;
[1]Unsubstituted oligonucleotide, no $N_2$—functionalization;
[2]$N_2$—Biotin functionalization;
[3]$N_2$—Fluorescein functionalization;
[3]$N_2$—Rhodamine functionalization;
[4]$N_2$—Cholic Acid functionalization; and
[5]$N_2$—Aromatic azide functionalization;
[7]$N_2$—Bromoacetyl alkylator functionalization;

EXAMPLE 78

Purine oligonucleotides with $N_2$ Protected Hexylamine Tethers

The phosphoramidite compound, 5'-dimethoxytrityl-$N_2$-($\Omega$-N-trifluoroacetylhexylamino-2'-deoxyguanosine-3'-O-[2-cyanoethyl-N,N-diisopropyl]phosphoramidite, is utilized in the DNA synthesizer as a 0.2M solution in anhydrous $CH_3CN$. Oligonucleotide synthesis is carried out in either an ABI 380B or an ABI 394 synthesizer employing the standard synthesis cycles with an extended coupling time of 10 minutes during coupling of the modified amidite into the oligonucleotide sequence. Coupling efficiency of greater than 90% is observed.

A. Phosphodiester oligonucleotides With An $N_2$ Alkyl Amine Linking Group

The following oligonucleotides having phosphodiester inter-nucleotide linkages are synthesized:

Oligomer 24: (SEQ ID NO:7):
   5' TG*G GAG CCA TAG CGA GGC 3' (ICAM-1; P=O);
Oligomer 25: (SEQ ID NO:8):
   5' TG*G GAG CCA TAG* CGA GGC 3' (ICAM-1; P=O);

wherein G* represents a nucleotide functionalized to incorporate a $N_2$-hexylaminofunctionality. Oligomers 24 and 25 are antisense compounds targeted against the human ICAM-1 (Inter Cellular Adhesion Molecule-1). The oligonucleotides are synthesized in either a 10 mmol scale or a 3×1 mmol scale in the "Trityl-On" mode. Standard deprotection conditions (30% $NH_4OH$, 55° C., 24 hours) are employed. The oligonucleotides are purified by reverse phase HPLC (Waters Delta-Pak $C_4$ 15 m, 300A, 25×100 mm column equipped with a guard column of the same material). They are detritylated and further purified by size exclusion using a Sephadex G-25 column.

B. Phosphorothioate Oligonucleotide With $N_2$-Hexylamine Linking Group

The following oligonucleotide having phosphorothioate inter-nucleotide linkages are synthesized:

Oligomer 26: (SEQ ID NO:9):
5' TsG*sGs GsAsGs CsCsAs TsAsGs CsGsAs GsGsC 3' (ICAM-1; P=S); wherein G* represents a nucleotide functionalized to incorporate a $N_2$-hexylamine functionality and the subscript "s" represents a phosphorothioate internucleotide backbone linkage. Oligomer 4 is an antisense compound to ICAM and it has the same sequence as oligomer 4 in PCT Application WO 93/07883 except for the purine modification. These oligonucleotides are synthesized as per the method of Example 75 except during the synthesis, for oxidation of the phosphite moieties, the Beaucage reagent (i.e., 3H-1,2-benzodithioate-3-one 1,1-dioxide, see, Iyer, R. P., et al., J. Am. Chem. Soc. 1990, 112, 1253) is used as a 0.24M solution in anhydrous $CH_3CN$ solvent. The oligonucleotides are synthesized in the "Trityl-On" mode and purified by reverse phase HPLC utilizing the purification of procedure of Example 76.

D. 2'-O-Methyl Derivatized RNA Oligonucleotides Containing $N_2$-hexylamine Linking Group The following oligonucleotides having 2'-O-methyl groups on each nucleotide not functionalized with a $N_2$-hexylamine functionalization are synthesized:

Oligomer 27: (SEQ ID NO:6):
   G*CUCUCUC;
Oligomer 28: (SEQ ID NO:7):
   CGAGAUCUGAG*C wherein G* represents a nucleotide functionalized to incorporate a $N_2$-hexylamine functionality and where the remaining nucleotides are each 2'-O-methyl derivatized nucleotides. Both Oligomers 27 and 28 are sequences in the HIV-1 TAR region. The oligonucleotides are synthesized as per the method of Example 75 and 76 using modified (G*) phosphoramidites and appropriate 2-O-methyl phosphoramidite nucleotides from Chemgenes Inc. (Needham, Mass.) for the remaining RNA nucleotides. The oligonucleotides are deprotected and purified as per the method of Example 76(A).

EXAMPLE 79

Conjugation Reactions of the $N_2$-hexylamine Tether

To illustrate the conjugation potential of the $N_2$-hexylamine tether, oligonucleotides 24 and 25 are treated with different classes of compounds each having either an N-hydroxysuccinimide ester or a isothiocyanate group and the desired functionality at the other end. The following compounds are employed: a) biotin-aminocaproyl-NHS-ester, b) cholic acid-NHS-ester, c) cholesterol hemisuccinate NHS ester, d) pyrene butyrate-NHS-ester, e) aromatic azide-NHS-ester, f) bromoacetic acid-NHS-ester, g) fluorescein-NCS, and h) rhodamine-NCS.

The conjugations are carried out in either 0.2M bicarbonate buffer (pH 8.1) or 1.0M borate buffer for N-hydroxysuccinimide esters and 1M bicarbonate/carbonate buffer (pH 9.0) for isothiocyanate reactions. The conjugates are easily purified by size exclusion and reverse phase HPLC and characterized by their UV-VIS spectra (where applicable). The retention times of different oligonucleotides and their conjugates are measured. The reaction conditions, purification, characterization and yields are similar to those in Example 77.

EXAMPLE 80
Attachment of aminolinker at 8 position of purines

A. Preparation of 5'-Dimethoxytrityl-8-(N-Fmoc-aminocaproyl-aminomethyl)-2'-deoxyadenosine-6-benzoyl-3'-O-[2-cyanoethyl-N,N-diisopropyl] phosphoramidite 8-bromo-2'-deoxyadenosine is reacted with sodium cyanide in DMF. Resulting 8-position modified nucleoside is then reduced with Pd-hydrogen to give 8-aminomethyl-2'-deoxyadenosine. This compound is then condensed with N-Fmoc-aminocaproic acid-pentafluorophenyl ester. This introduces a —$CH_2$— NH—CO—$(CH_2)_5$—NH-Fmoc functionality at the 8-position of adenosine. Further treatment with $(CH_3)_3SiCl$, Ph—C(O)—Cl and $NH_4OH$ yielded $N_6$-benzoyl protected 8-position functionalized adenosine. Treatment with dimethoxytrityl chloride and pyridine added a DMT blocking group at the 5'-position. Finally phosphitylation gave the desired phosphoramidite compound which is incorporated into oligonucleotides.

B. Preparation of 5'-Dimethoxytrityl-8-(N-Fmoc-aminocaproyl-aminomethyl)-$N_2$-isobutyryl-2'-deoxyguanosine-3'-O-(2-cyanoethyl-N,N-diisopropyl)phosphoramidite 8-bromo-2'-deoxyguanosine is reacted with sodium cyanide in DMF. The resulting 8-position modified nucleoside is then reduced with Pd-hydrogen to give 8-aminomethyl-2'-deoxyguanosine. This compound is then condensed with N-Fmoc-aminocaproic acid-pentafluorophenyl ester. This introduces a —$CH_2$—NH—CO—$(CH_2)_5$—NH-Fmoc functionality at the 8-position of guanosine. Further treatment with $(CH_3)_3SiCl$, isobutyric anhydride and $NH_4OH$ yielded $N_2$-isobutyryl protected 8-position functionalized guanosine. Treatment with dimethoxytrityl chloride and pyridine added a DMT blocking group at the 5'-position. Finally phosphitylation gave the desired phosphoramidite compound which is incorporated into oligonucleotides.

EXAMPLE 81
Purine Oligonucleotides with an 8-Amino tether

A. 8-(Ω-aminocaproyl-aminomethyl)-2'-deoxyadenosine containing Oligonucleotides

The phosphoramidite compound, 5'-Dimethoxytrityl-8-(N-Fmoc-aminocaproyl-aminomethyl)-2'-deoxyadenosine-6-benzoyl-3'-O-(2-cyanoethyl-N,N-diisopropyl) phosphoramidite, is utilized in the DNA synthesizer as a 0.2M solution in anhydrous $CH_3CN$. Oligonucleotide synthesis is carried out in either an ABI 380B or an ABI 394 synthesizer employing the standard synthesis cycles with an extended coupling time of 10 minutes during coupling of the modified amidite into the oligonucleotide sequence. Coupling efficiency of greater than 90% is observed.

B. 8-(Ω-aminocaproyl-aminomethyl)-2'-deoxyguanonosine containing Oligonucleotides The phosphoramidite compound, 5'-Dimethoxytrityl-8-(N-Fmoc-aminocaproyl-aminomethyl)-$N_2$-isobutyryl-2'-deoxyguanosine-3'-O-[2-cyanoethyl-N,N-diisopropyl] phosphoramidite, is utilized in the DNA synthesizer as a 0.2M solution in anhydrous $CH_3CN$. oligonucleotide synthesis is carried out in either an ABI 380B or an ABI 394 synthesizer employing the standard synthesis cycles with an extended coupling time of 10 minutes during coupling of the modified amidite into the oligonucleotide sequence. Coupling efficiency of greater than 90% is observed.

C. 8-(Ω-aminocaproyl-aminomethyl)guanosine Group Containing Phosphodiester Oligonucleotides The following oligonucleotides having phosphodiester inter-nucleotide linkages are synthesized:

Oligomer 29: (SEQ ID NO:2):
5' TG*G GAG CCA TAG CGA GGC 3' (ICAM-1; P=O);

Oligomer 30: (SEQ ID NO:2):
5' TG*G GAG CCA TAG* CGA GGC 3' (ICAM-1; P=O);

wherein G* represents a nucleotide functionalized to incorporate an 8-(Ω-aminocaproyl-aminomethyl)guanosine functionality. Oligomers 24 and 25 are antisense compounds targeted against the human ICAM-1 (Inter Cellular Adhesion Molecule-1). The oligonucleotides are synthesized in either a 10 mmol scale or a 3×1 mmol scale in the "Trityl-On" mode. Standard deprotection conditions (30% $NH_4OH$, 55° C., 24 hours) are employed. The oligonucleotides are purified by reverse phase HPLC (Waters Delta-Pak $C_4$ 15 m, 300A, 25×100 mm column equipped with a guard column of the same material). They are detritylated and further purified by size exclusion using a Sephadex G-25 column.

D. 8-(Ω-aminocaproyl-aminomethyl)adenosine Group Containing Phosphodiester Oligonucleotides The following oligonucleotides having phosphodiester inter-nucleotide linkages were synthesized:

Oligomer 31
CTG TCT CCA* TCC TCT TCA CT;

Oligomer 32:
CTG TCT CCA* TCC TCT TCA* CT;

wherein A* represents a nucleotide functionalized to incorporate 8-(Ω-aminocaproyl-aminomethyl)adenosine functionality. Oligomers 12 and 13 are antisense compounds to the E2 region of the bovine papilloma virus-1 (BPV-1). Oligomers 31 and 32 have the same sequence as Oligomer 3 in PCT Application WO 93/07883, except for the 8-position modification. The oligonucleotides were synthesized in either a 10 µmol scale or a 3×1 µmol scale in the "Trityl-On" mode. Standard deprotection conditions (30% $NH_4OH$, 55° C., 24 hours) were employed. The oligonucleotides were purified by reverse phase HPLC (Waters Delta-Pak $C_4$ 15 µm, 300A, 25×100 mm column equipped with a guard column of the same material). They were detritylated and further purified by size exclusion using a Sephadex G-25 column.

EXAMPLE 82
Conjugation Reactions of the 8-(Ω-aminocaproyl-aminomethyl)guanosine Group Containing Phosphodiester oligonucleotides and 8-(Ω-aminocaproyl-aminomethyl) adenosine Group containing Phosphodiester oligonucleotides To illustrate the conjugation potential of the $C_8$ alkylamine tether, the oligonucleotides 29, 30, 31, and 32 are treated separately with different classes of compounds each having either an N-hydroxysuccinimide ester or a isothiocyanate group and the desired functionality at the other end. The following compounds are employed: a) biotin-aminocaproyl-NHS-ester, b) cholic acid-NHS-ester, c) cholesterol hemisuccinate-NHS-ester, d) pyrene butyrate-NHS-ester, e) aromatic azide-NHS-ester, f) bromoacetic acid-NHS-ester, g) fluorescein-NCS, and h) rhodamine-NCS. The conjugations are carried out in either 0.2M bicarbonate buffer (pH 8.1) or 1.0M borate buffer for N-hydroxysuccinimide esters and 1M bicarbonate/carbonate buffer (pH 9.0) for isothiocyanate reactions. The conjugates are easily purified by size exclusion and reverse phase HPLC and characterized by their UV-VIS spectra (where applicable). The retention times of different oligonucleotides and their conjugates are measured. The reaction conditions, purification, characterization and yields are similar to those in Example 76.

EXAMPLE 83
Introduction of a suitable crosslinker to the 2 position of a purine nucleotide
Attachment of thiol lnker at 2 position of purines Portions of S-trityl-6-mercaptohexylbromide, are independently treated with sodium cyanide followed by hydrolysis to give the corresponding acid, S-trityl-6-mercaptohexanoic acid, or with lithium azide followed by triphenylphosphine reduction to give the corresponding amine, S-trityl-6-mercapto hexylamine or with sodium hydrogen sulfide to give the corresponding thiol, (1-S-trityl-thio-hexylmercaptan).

2-fluoro-2'-deoxyinosine is reacted with S-trityl-6-mercapto hexylamine following the conditions of Harris, C. M. et al., *J. Am. Chem. Soc.* 113, 4328, 1991. The resulting nucleoside having the thiol linker at the 2 position of its purine ring as per the above example is further derivatized and incorporated into oligonucleotides.

EXAMPLE 84
Introduction of a suitable crosslinker to the 8 position of purine nucleotides
Attachment of thiol linker at the 8 position of purines 8-bromoadenosine is reacted with the sodium salt of 1-S-trityl-thio-hexylmercaptan. The resulting 8 position modified nucleoside is then further modified and incorporated into oligonucleotides as per the above example.

EXAMPLE 85
Introduction of a suitable aldehyde crosslinker to the 6 position of purine nucleotides A. 6-O-Pentafluorophenyladenosine is prepared according to Gao et al., *J. Org. Chem.*, 1992, 57, 6954–6959. 3-bromopropionaldehyde is converted to the corresponding bis(o-nitrobenzyl)acetal by treating with o-nitrobenzylalcohol in the presence of p-toluene sulfonic acid. The bromoacetal is reacted with lithium azide in DMF to give 3-azidopropionaldehyde bis(o-nitrobenzyl)acetal that is then reduced with triphenylphosphine/pyridine to give 3-aminopropionaldehyde bis(o-nitrobenzyl)acetal. 6-O-pentafluorophenyladenosine is treated with 3-aminopropionaldehyde bis(o-nitrobenzyl)acetal. Further treatment with $(CH_3)_3SiCl$, Ph—C(O)—Cl and $NH_4OH$ yielded $N_6$-benzoyl protected 6-position functionalized adenosine. Treatment with dimethoxytrityl chloride and pyridine added a DMT blocking group at the 5'-position. Finally phosphitylation gave the desired phosphoramidite compound which is incorporated into oligonucleotides carrying a masked aldehyde at the 6-position of adenosine.

B. Similarly, 6-O-pentafluorophenyl-2'-deoxyguonosine is prepared and converted to the corresponding $N_6$-[3-aminopropionaldehyde bis(o-nitrobenzyl)acetal]. Further treatment with $(CH_3)_3SiCl$, Ph—C(O)—Cl and $NH_4OH$ yielded $N_6$-benzoyl protected 6-position functionalized guonosine. Treatment with dimethoxytrityl chloride and pyridine added a DMT blocking group at the 5'-position. Finally, phosphitylation gave the desired phosphoramidite compound which is incorporated into oligonucleotides carrying a masked aldehyde at the 6-position of guonosine.

EXAMPLE 86
Attachment of amine and Aldehyde linker at 5 position of pyrimidines A. 3',5'-di-toluyl-5-iododeoxyuridine is condensed with N-trifluoroacetyl-propargylamine in the presence of bis-(triphenylphosphine) palladium chloride and cuprous iodine (Haralambidis, J.; Chais, M.; Treagear, G. W. *Nucleic Acids Res.* 15, 4857, 1987). This nucleoside is then deprotected to give the free amine at the 5 position which is condensed with HOOC-$(CH_2)$6-NH-Fmoc.

B. Preparation of 2'-deoxyuridine-5-(propionic acid methyl ester) is carried out according to the published procedure of Telser et al., (Telser, J.; Cruickshank, K. A.; Morrison, L. E.; and Netzel, T. L. *J. Am. Chem. Soc.* 111, 6966 (1989). Briefly, 5-chloro-mercury-2'-deoxyuridine is reacted with methyl acrylate under the conditions described by Dreyer and Dervan (Dreyer, G. B.; Dervan, P. B.; *Proc. Natl. Acad. Sci. USA* 82, 968 (1985). The resultant 2'-deoxyuridine-5-(propenoic acid methyl ester) is reduced with hydrogen/palladium on carbon to yield 2'-deoxyuridine-5-(propionic acid methyl ester).

This compound is converted to the 5'-dimethoxytrityl derivative and then reacted with 1,6-hexanediamine by an ester-amide exchange reaction as described by Dreyer and Dervan, ibid for other amines.

C. 2'-Deoxyuridine-5-propionic acid methyl ester is reduced to 2'-deoxyuridine-5-propanaldehyde using DIBAL (diisobutylaluminum hydride). This aldehyde is converted into the corresponding acetal using 0-nitrobenzyl alcohol. The nucleoside is then 5'-dimethoxytritylated and 3'-phosphitylated to give an aldehyde precursor phosphoramidite.

EXAMPLE 87
Functionalization of N-3 position of pyrimidines for crosslinking Preparation of 5'-O-Dimethoxytrityl-$N_3$-[propionaldehyde bis(o-nitrobenzyl)acetal]-2'-deoxyuridine-3'-O-(2-cyanoethyl-N,N-diisopropyl) phosphoramidite 2'-Deoxyuridine is alkylated with NaH and 3-bromopropion-aldehyde bis(o-nitrobenzyl)acetal. The mixture is stirred at room temperature for 16 hrs. under argon. The reaction mixture is evaporated, co-evaporated once with toluene and the product is mainly $N_3$ alkylated product. This product is dried under vacuum and re-evaporated twice with pyridine. It is dissolved in anhydrous pyridine and treated with dimethyoxytrityl chloride and small amount of dimethylaminopyridine (DMAP). The product is then phosphitylated to give the desired amidite.

EXAMPLE 88
Incorporation of crosslinking linkers into oligonucleotides

5'-Dimethoxytrityl-$N_2$-($\Omega$-N-trifluoroacetylpropylamino-2'-deoxyguanosine-3'-O-(2-cyanoethyl-N,N-diisopropyl) phosphoramidite, 5'-dimethoxytrityl-$N_2$($\Omega$-N-trifluoroacetylhexylamino)-2'-deoxyguanosine-3'-O-(2- cyanoethyl-N,N-diisopropyl)phosphoramidite, 5'-dimethoxytrityl-8-(N-Fmoc-aminocaproyl-aminomethyl)-2'-deoxyadenosine-6-benzoyl-3'-O-(2-cyanoethyl-N,N-diisopropyl)phosphoramidite, 5'-dimethoxytrityl-8-(N-Fmoc-aminocaproyl-aminomethyl)-$N_2$-isobutyryl-2'-deoxyguanosine-3'-O-(2-cyanoethyl-N,N-diisopropyl)phosphoramidite, 5'-dimethoxytrityl-$N_2$-($\Omega$-S-tritylhexylmercapto)-2'-deoxyguanosine-3'-O-(2-cyanoethyl-N,N-diisopropyl)phosphoramidite, and 5'-dimethoxytrityl-$N_2$($\Omega$-S-tritylhexylmercapto)-6-benzoyl-2'-deoxyadenosine-3'-O-(2-cyanoethyl-N,N-diisopropyl)phosphoramidite are used to incorporate the crosslinking linkers into oligomers using the protocols described in Example 76.

EXAMPLE 89

Incorporation of crosslinking linkers into oligonucleotides (complementary strand)

5'-O-Dimethoxytrityl-$N_3$-[propionaldehyde bis(o-nitrobenzyl)acetal]2'-deoxyuridine-3'-O-(2-cyanoethyl-N,N-diisopropyl)phosphoramidite, 5'-O-(dimethoxytrityl)-$N_6$-[aminopropionaldehyde-bis(o-nitrobenzyl)acetal]-$N_2$-isobutyryl-2'-deoxyguonosine-3'-O-[2-cyanoethyl-N,N-diisopropyl]phosphoramidite, and 5'-O-Dimethoxytrityl-$N_6$-[aminopropionaldehyde-bis(o-nitrobenzyl)acetal]-2'-deoxyadenosine-3'-O-(2-cyanoethyl-N,N-diisopropyl)phosphoramidite are used to incorporate the crosslinking linkers into oligomers using the protocols described in Example 76.

EXAMPLE 90

Crosslinking reactions and structures using HIV TAR $N_2$ to $N_2$ via formaldehyde The following oligonucleotides having 2'-O-methyl groups on each nucleotide not functionalized with a $N_2$-hexylamine functionalization are synthesized:

Oligomer 27: (SEQ ID NO:6):
G*CUCUCUC;

Oligomer 28: (SEQ ID NO:7):
CGAGAUCUGAG*C;

wherein G* represents a nucleotide functionalized to incorporate a $N_2$-hexylamine functionality and where the remaining nucleotides are each 2'-O-methyl derivatized nucleotides. Both oligomers 6 and 7 are sequences in the HIV-1 TAR region. An equimolar mixture of these oligomers are mixed with formaldehyde (1.0 equivalent) and sodium cyanoborohydride at pH 5.0. The resultant TAR crosslink is purified by HPLC as described below.

EXAMPLE 91

Crosslinking reactions and structures using HIV TAR $N_2$ to $N_2$ via glutaraldehyde The following oligonucleotides having 2'-O-methyl groups on each nucleotide not functionalized with a $N_2$-propylamine functionalization are synthesized:

Oligomer 29: (SEQ ID NO:6):
G*CUCUCUC;

Oligomer 30: (SEQ ID NO:7):
CGAGAUCUGAG*C;

wherein G* represents a nucleotide functionalized to incorporate a $N_2$-propylamine functionality and where the remaining nucleotides are each 2'-O-methyl derivatized nucleotides. Both Oligomers are sequences in the HIV-1 TAR region. An equimolar mixture of these oligomers are mixed with glutaraldehyde (1.0 equivalent) and sodium cyanoborohydride at pH 5.0. The resultant TAR crosslink is purified by HPLC as described below.

EXAMPLE 92

Crosslinking reactions and structures using $N_2$-Guanosine to abasic site

Preparation Of Oligonucleotides Having Abasic Sites Located Thereon

A. Preparation of An Abasic site Containing Oligonucleotide Via Enzymatic Reaction i. Oligonucleotide Containing Single Uridine site An oligonucleotide of the sequence:
Oligomer 31: CGC AGU* CAG CC;

wherein U* represents a 2'-deoxyuridine nucleotide prepared utilizing the procedure of Example 76. The deoxyuridine nucleotide in the middle of the sequence is added during the synthesis utilizing deoxyuridine phosphoramidite (Glen Research, Sterling, Va.). The oligonucleotide is prepared utilizing standard synthesis cycles. It is deprotected by normal deprotection utilizing ammonium hydroxide, 30%, for 16 hours. The solvent is evaporated, and the residue is purified by HPLC and detritylated. Final purification is effected on Sephadex G-25.

ii. Enzyme Stock Solution Preparation

Uracil-DNA glycosylase is isolated from *E. coli* M5219 cells transformed with the expression plasmid pBD396 containing the ung gene. The enzyme is purified to electrophoretic homogeneity as described by Lindahl, et al., *J. Biol. Chem.*, 1977, 252, 3286, and stored in 30 Mm HEPES-NaOH, pH 7.4, containing 5% glycerol, 2 mM DTT and 1 mM EDTA.

iii. Oligonucleotide Containing single Abasic Site

An abasic oligonucleotide of the sequence:
Oligomer 32: CGC AGD* CAG CC;

wherein D* represents an abasic site, is prepared by treating 237 O.D. units of Oligomer 31 of Example 92(A)(i) in 0.5 ml water with 200 μl of the stock solution of Example 92(A)(ii) (200 micrograms of uracil DNA-glycosylase) and incubating at room temperature overnight. HPLC analysis showed quantitative removal of uracil as indicated by a 1:10 ratio between uracil and the abasic dodecamer oligonucleotide. The uracil retention time is 2.43 mins and the abasic oligonucleotide is 21.68 mins. The solution is lyophilized and stored in the freezer until further use.

B. Preparation of An Abasic Site Containing oligonucleotide Via Abasic Sugar Precursor i. 5-O-(4,4'-Dimethoxytrityl)-1,2-Dideoxy-D-Ribofuranose-3-O-(2-Cyanoethyl-N,N'-Diisopropyl) Phosphoramidite 5-O-(4,4'-Dimethoxytrityl)-1,2-dideoxy-D-ribofuranose-3-O-(2-cyanoethyl-N,N'-diisopropyl)phosphoramidite is prepared as per the procedure of Lyer, et al., *Nucleic Acids Research,* 1990, 18, 2855, or as per the procedure of Didier Peoch et al., *Tetrahedron Letters,* 1991, 32, 207.

ii. Oligonucleotide Containing Abasic Site

Oligomer 32 of Example 92(A) (iii), i.e. the oligonucleotide of the sequence:
Oligomer 32 CGC AGD* CAG CC
wherein D* represents an abasic site, can also be prepared utilizing the synthetic procedures of the papers identified in Example 92(B)(i). Utilizing those procedures, an o-Nitrobenzyldeoxyfuranose containing oligonucleotide is synthesized using the oligonucleotide synthetic methods of these papers. Photolysis, utilizing a high intensity Hg lamp (300 nm), generates the corresponding abasic site containing oligonucleotide. Such abasic oligonucleotides are also described by Horn, et al., *Nucleosides & Nucleotides*, 1991, 10, 299.

EXAMPLE 93

Preparation of Oligonucleotides Incorporating an $N_2$-Amine Functionalized Space-spanning Group An oligonucleotide of the sequence:

Oligomer 33 GGC TGG* CTG CG wherein G* indicates a $N_2$-hexylaminoguanosine nucleotide is prepared as per the procedure of Example 76 utilizing an extended coupling time of 10 minutes during the coupling step of the modified nucleotide unit. 5'-dimethoxytrityl-$N_2$ ($\Omega$-N-trifluoroacetylhexylamino- 2'-deoxyguanosine-3'-O-(2-cyanoethyl-N,N-diisopropyl)phosphoramidite (from Example 77) is utilized in the DNA synthesizer as a 0.15M solution in anhydrous $CH_3CN$. Oligonucleotide synthesis is carried out in either an ABI 390B or 394 synthesizer employing the standard synthesis cycles with an extended coupling time of 10 minutes during coupling of the modified phosphoramidite into the oligonucleotide sequence. Coupling efficiency of >95% is observed for the modified phosphoramidite coupling. Removal of the N-trifluoroacetyl amine protecting group is effected simultaneously with $NH_4OH$ deprotection of the benzoyl and isobutyryl nucleotide base blocking groups.

EXAMPLE 94

Crosslinking of Oligonucleotide Strand Having An Abasic Site To An oligonucleotide Having $N_2$-guanosine Amine Functionalized Space-spanning Group Two stranded, duplexed, cross-linked oligonucleotides of the structure:

| Cross-linked Duplex I | | | |
|---|---|---|---|
| GGC | AGD* | CAG | CC |
| GGC | TGG* | CTG | CG | wherein the crosslink is formed between the asterisks by an NH—$(CH_2)_6$—NH—$CH_2$— cross-linkage between the oligonucleotide strands. The crosslinked oligonucleotides are prepared by reacting 2.8 O.D. units of Oligomer 33, i.e. the GGC TGG* CTG CG oligonucleotide of Example 93, in 100 $\mu$l of 0.2M NaOAc buffer (pH 5.02) with 2.37 O.D. units of Oligomer 32, i.e. the abasic oligonucleotide CGC AGD* CAG CC of Example 92, dissolved in 10 $\mu$l of water. The combined solution is let stand for 2 hours. 10 mg of $NaCNBH_3$ is dissolved in 400 $\mu$l of 250 mM NaOAc (pH 5.02) and 25 $\mu$l of this solution is added to the reaction solution. After this addition, the final concentration of the cyanoborohydride in the solution is nearly 80 mM. The reaction is followed at 1 hr intervals by HPLC. The amine linked oligonucleotide had a retention time around 21 mins and the abasic oligonucleotide 22 mins. A product peak is observed at a later elution time. A slow increase in the product peak is observed. After 12 hrs the product is separated from the reaction mixture by HPLC yielding the pure product. A small aliquot of the product is re-injected into the HPLC column and observed as a single peak.

B. Gel Analysis

A gel analysis is carried out on the above cross-linked 11 mer oligonucleotides, i.e. cross-linked duplex I. The cross linked material moved slower than either of its component 11 mer oligonucleotides, i.e. Oligomers 32 or 33. Indeed it has the same electrophoretic mobility similar to that of a 21 mer oligonucleotide (11+11 −1 for the loss of a base).

C. Ion Exchange Chromatography

Cross-linking of the cross-linked duplex I is further confirmed by using ion exchange chromatography. The 21 mer cross-linked strands, since they have the greatest amount of charge, are eluted at 0.25M salt concentration whereas the 11 mer components oligonucleotides are eluted at 0.15M salt concentration.

D. Cross-Linking Affirmation

Cross-linking as opposed to hybridization duplex formation is confirmed independently by gel analysis and by re-injection of the cross-linked strands into HPLC. Gel analysis of a mixture the two component oligonucleotides mixed together without cross-linking does not yield the 21 mer mobility product. Re-injection of the cross-linked product into HPLC does not produce an equilibrium mixture of the two single oligonucleotide strands but comes out as a single peak.

EXAMPLE 95

Multiple Crosslinks From Oligonucleotide Containing Multiple Uridine Sites

A. Multiple Nucleophilic Sites

In the manner of Example 92(A) (i) the following oligonucleotide is prepared:

oligomer 34: GAC AGA GGU* AGG AGA AGU* GA;

wherein U* represents a 2'-deoxyuridine nucleotide. The oligonucleotide when treated as per the procedure of Example 92(A)(iii) will give an oligonucleotide of the sequence:

Oligomer 35: GAC AGA GGD* AGG AGA AGD* GA;

wherein D* represents an abasic site within the oligonucleotide.

B. Multiple Nucleophilic Sites

An oligonucleotide of the sequence:

Oligomer 36: CTG TCT CCG* TCC TCT TCG* CT;

wherein G* represents a nucleotide modified to incorporate a $N_2$-hexylamino functionality is prepared as per the procedures of Example 93. This oligonucleotide is an antisense compound to the E2 region of the bovine papilloma virus-1 (BPV-1).

C. Cross-Linking Via Dual Abasic Sites

Two stranded duplexed, multi-site cross-linked oligonucleotides of the structure:

| Cross-linked Strand II | | | | | |
|---|---|---|---|---|---|
| CTG TCT | CCG* | TCC | TCT | TC | G*CT |
| GAC AGA | GGD* | AGG | AGA | AGD* | GA | wherein the crosslink is formed between the asterisks. The crosslinkage is formed from Oligomer 35 from Step A and oligomer 36 from Step B utilizing the cross-linking procedure of Example 92. The resulting cross-linked strands are held together not only by hybridization of the duplex structures but also by the dual cross-linkages extending between the individual oligonucleotide strands.

EXAMPLE 96

Crosslinking with the TAR structure

A. Preparation of 5-O-(4,4'-Dimethoxytrityl)-2-O-Methyl-1,2-Dideoxy-1-(o-nitrobenzyl)-D-Ribofuranose-3-O-(2-Cyanoethyl-N,N'-Diisopropyl)Phosphoramidite.

1-O-acetyl-2,3,5-tri-O-benzoyl-D-ribofuranose is condensed with O-nitrobenzyl alcohol under Vorbruggen conditions. The resultant 1-O-(ortho-nitrobenzyl)-2,3,5-tri-O-benzoyl (a,α)-D-ribofuranose is deprotected with ammonia and subsequently treated with TIPS-Cl$_2$. The resultant 3,5-silyl protected 1-O-(ortho-nitro benzyl) D-ribofuranose is reacted with diazomethane or CH$_3$I/Ag$_2$O to give the required 2-O-methyl compound. Subsequent 3,5-deprotection, 5-dimethoxy tritylation and 3-phosphitylation gives the named phosphoramidite. The phosphoramidite is incorporated into an oligonucleotide via standard phosphoramidite procedures.

B. Preparation of oligonucleotide Having Multiple Space-spanning Groups That Include The Same or Different Functionalities Thereon Aldehyde and Amine Functionality Containing Oligonucleotide A oligonucleotide of the structure:

Oligomer 37: AGC CAG* AUC UGA GCC UGG GAG CD**C UCU GGC U wherein G* represents an guanosine nucleotide having an N$_2$-hexylamino group thereon and D represents a 2'-OMe, deoxyribose nucleotide having an 1,2-dideoxy-1-(o-nitrobenzyl)-D-ribofuranose group thereon will be prepared as per the procedure of Example 92 utilizing the nucleotides of Examples 76 and Step A above respectively, for the functionalized space-spanning group containing nucleotides.

C. Coupling of Two Sites on Single Strand

A single strand duplexed, cross-linked, hairpin loop oligonucleotide of the structure:

Cross-linked Strand III

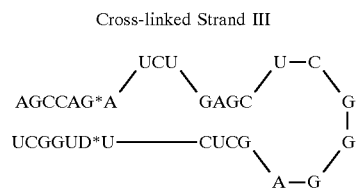

wherein the crosslink is formed between the asterisks. The crosslinker represents a covalent bond formed via an oxime linkage between the regions of the strand which is prepared from Oligomer 37 from Example 96(B). Oligomer 37 is taken up in 0.1M NaCl solution to effect hybridization and then subjected to photolysis with 300 nm UV light to remove aldehydic protecting groups. Sodium acetate buffer (pH 5.0) is then added to effect the formation of a Schiff's base linkage between the amine and aldehyde groups. NaCNBH$_3$ is added to reduce the oxime linkage to an amine linkage whereby the resulting cross-linked strand will be held together not only by hybridization of the duplex stem portion of the hairpin loop structure but also by the covalent cross-linkage extending across the stem nucleotides.

EXAMPLE 97

Crosslinking reactions and structures using HIV TAR N$_6$ to C$_5$

A TAR oligonucleotide comprising the nucleosides from position 16 to 46 is synthesized incorporating modified phosphoramidites with linker arms at positions 20 and 42 and RNA phosphoramidites for the rest of the positions. The nucleophilic arm is synthesized from C$_5$ of uridine (example 86) at position 42 and the electrophilic arm from N$_6$ of adenosine (example 85) at position 20 of the TAR structure via a Schiff base formation followed by reduction to give the crosslink.

EXAMPLE 98

Crosslinking reactions and structures using HIV TAR: N$_6$ of Purines to N$_3$ of Pyrimidines A TAR oligonucleotide comprising the nucleosides from position 16 to 46 is synthesized incorporating modified phosphoramidites with linker arms at positions 20 and 42 and RNA phosphoramidites for the rest of the positions. The nucleophilic arm was synthesized from N$_3$ of uridine, (example 87), at position 42 and the electrophilic arm from N$_6$ of adenosine, (example 85), at position 20 via a Schiff base formation followed by reduction to give the crosslink.

EXAMPLE 99

Crosslinking reactions and structures using HIV TAR: C$_8$ to C$_5$

A TAR oligonucleotide comprising the nucleosides from position 16 to 46 is synthesized incorporating modified phosphoramidites with linker arms at positions 20 and 42 and RNA phosphoramidites for the rest of the positions. The nucleophilic arm is synthesized from C$_8$ of adenosine, (example 81), at position 20 and the electrophilic arm from C$_5$ of uridine, (example 86(C)), at position 42 via a Schiff base formation followed by reduction to give the crosslink.

EXAMPLE 100

Crosslinking reactions and structures using HIV TAR: C$_8$ to N$_3$

The nucleophilic arm is synthesized from C$_8$ of adenosine, (example 81), at position 20 and the electrophilic arm from N$_3$ of uridine, (example 87), at position 42 via a Schiff base formation followed by reduction to give the crosslink.

What is claimed is:

1. A compound having the formula:

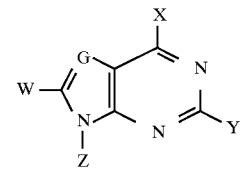

wherein:

G is CR$_1$;

R$_1$ is a hydrocarbyl group having from 1 to 6 carbon atoms;

X is halogen, NH$_2$, OH, NHR$_2$Q$_1$ or OR$_2$Q$_1$, wherein said R$_2$ is a hydrocarbyl group having from 1 to about 20 carbon atoms, and Q$_1$ comprises a reactive or non-reactive functionality;

Y is halogen, NH$_2$, H, R$_3$Q$_2$, or NHR$_3$Q$_2$, wherein said R$_3$ is a hydrocarbyl group having from 1 to about 20 carbon atoms, and Q$_2$ comprises a reactive or non-reactive functionality;

W is H, R$_4$Q$_3$, or NHR$_4$Q$_3$, wherein said R$_4$ is a hydrocarbyl group having from 1 to about 20 carbon atoms, and Q$_3$ comprises a reactive or non-reactive functionality;

Z is a ribose sugar analog or a deoxyribose sugar analog which bears at least one substituent at the 3' or 5' position of said deoxyribose sugar analog, or at the 2', 3', or 5' position of said ribose sugar analog; said substituent being selected from the group consisting of O, H, lower alkyl, substituted lower alkyl, aralkyl, heteroaralkyl, heterocycloalkyl, amino-alkylamino, heterocycloalkyl, polyalkylamino, substituted silyl, F, Cl, Br, CN, $CF_3$, $OCF_3$, OCN, O-alkyl, S-alkyl, SOMe, $SO_2Me$, $ONO_2$, $NO_2$, $N_3$, $NH_2$, NH-alkyl, $OCH_2CH=CH_2$, $OCH=CH_2$, $OCH_2CCH$, OCCH, OCCHO, and an RNA cleaving moiety;

said reactive functionality is selected from the group consisting of halogens, heterocycles, heterocycloalkyls, heterocycloalkylamines, polyalkylamines, aminoalkylamines, ethers, esters, aldehydes, ketones, aryl groups, hydrazines, hydroxylamines, semicarbazides, thiosemicarbazides, hydrazones, hydrazides, alcohols, and thiols; and said unreactive functionality is selected from the group consisting of alkyl groups, polyamides, intercalators, and ethylene glycols.

2. The compound of claim 1 wherein said Z bears a substituent selected from the group consisting of F, $CF_3$, $OCF_3$, OCN, O-alkyl, S-alkyl, SOMe, $SO_2Me$, $OCH_2CH=CH_2$, $OCH=CH_2$, $OCH_2CCH$, OCCH, OCCHO, and an RNA cleaving moiety.

3. The compound of claim 2 wherein X is $NHR_2Q_1$, said $Q_1$ is a nitrogen-containing heterocycle having a plurality of ring atoms, one to four of said ring atoms being nitrogen atoms and the remainder being carbon atoms.

4. The compound of claim 2 wherein X is $NHR_2Q_1$, said $Q_1$ is a substituted or unsubstituted imidazole.

5. The compound of claim 2 wherein X is $OR_2Q_1$, said $Q_1$ is a nitrogen-containing heterocycle having a plurality of ring atoms, one to four of said ring atoms being nitrogen atoms and the remainder being carbon atoms.

6. The compound of claim 2 wherein X is $OR_2Q_1$, said $Q_1$ is a substituted or unsubstituted imidazole.

7. The compound of claim 2 wherein W is $R_4Q_3$, said $Q_3$ is a nitrogen-containing heterocycle having a plurality of ring atoms, one to four of said ring atoms being nitrogen atoms and the remainder being carbon atoms.

8. The compound of claim 2 wherein W is $R_4Q_3$, said $Q_3$ is a substituted or unsubstituted imidazole.

9. The compound of claim 2 wherein X is $NHR_2Q_1$, said $Q_1$ is an amine.

10. The compound of claim 2 wherein X is $OR_2Q_1$, said $Q_1$ is an amine.

11. The compound of claim 2 wherein W is $R_4Q_3$, said $Q_3$ is an amine.

12. A compound having the formula:

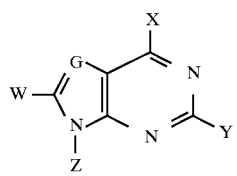

wherein:

G is N;

X is $NHR_2Q_1$ or $OR_2Q_1$, wherein said $R_2$ is a hydrocarbyl group having from 1 to about 20 carbon atoms, and $Q_1$ comprises a reactive or non-reactive functionality;

Y is halogen, $NH_2$, H, $R_3Q_2$, or $NHR_3Q_2$, wherein said $R_3$ is a hydrocarbyl group having from 1 to about 20 carbon atoms, and $Q_2$ comprises a reactive or non-reactive functionality;

W is $R_4Q_3$, or $NHR_4Q_3$, wherein said $R_4$ is a hydrocarbyl group having from 1 to about 20 carbon atoms, and $Q_3$ comprises a reactive or non-reactive functionality;

Z is a ribose sugar analog or a deoxyribose sugar analog which bears at least one substituent at the 3' or 5' position of said deoxyribose sugar analog, or at the 2', 3', or 5' position of said ribose sugar analog; said substituent being selected from the group consisting of O, H, lower alkyl, substituted lower alkyl, aralkyl, heteroaralkyl, heterocycloalkyl, amino-alkylamino, heterocycloalkyl, polyalkylamino, substituted silyl, F, Cl, Br, CN, $CF_3$, $OCF_3$, OCN, O-alkyl, S-alkyl, SOMe, $SO_2Me$, $ONO_2$, $NO_2$, $N_3$, $NH_2$, NH-alkyl, $OCH_2CH=CH_2$, $OCH=CH_2$, $OCH_2CCH$, OCCH, OCCHO, and an RNA cleaving moiety;

said reactive functionality is selected from the group consisting of halogens, heterocycles, heterocycloalkyls, heterocycloalkylamines, polyalkylamines, aminoalkylamines, ethers, esters, aldehydes, ketones, aryl groups, hydrazines, hydroxylamines, semicarbazides, thiosemicarbazides, hydrazones, hydrazides, alcohols, and thiols; and said unreactive functionality is selected from the group consisting of alkyl groups, polyamides, intercalators, and ethylene glycols.

13. The compound of claim 12 wherein said Z bears a substituent selected from the group consisting of F, $CF_3$, $OCF_3$, OCN, O-alkyl, S-alkyl, NH-alkyl, SOMe, $SO_2Me$, $OCH_2CH=CH_2$, $OCH=CH_2$, $OCH_2CCH$, OCCH, OCCHO, and an RNA cleaving moiety.

14. The compound of claim 12 further having a phosphate group at the 3' position of the sugar analog, wherein said phosphate group may be a native phosphate or a modified phosphate.

15. The compound of claim 14 wherein said Z bears a substituent selected from the group consisting of F, $CF_3$, $OCF_3$, OCN, O-alkyl, S-alkyl, NH-alkyl, SOMe, $SO_2Me$, $OCH_2CH=CH_2$, $OCH=CH_2$, $OCH_2CCH$, OCCH, OCHO and an RNA cleaving moiety; and said modified phosphate is a methylphosphonate, phosphorothioate, phosphorodithioate, phosphoramidite, or phosphorotriester.

16. A compound having the formula:

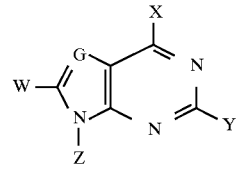

wherein:

G is N;

X is halogen, $NH_2$, OH, $NHR_2Q_1$ or $OR_2Q_1$, wherein said $R_2$ is a hydrocarbyl group having from 1 to about 20 carbon atoms, and $Q_1$ comprises a reactive or non-reactive functionality;

Y is $R_3Q_2$, or $NHR_3Q_2$, wherein said $R_3$ is a hydrocarbyl group having from 1 to about 20 carbon atoms, and $Q_2$ comprises a reactive or non-reactive functionality;

W is $R_4Q_3$, or $NHR_4Q_3$, wherein said $R_4$ is a hydrocarbyl group having from 1 to about 20 carbon atoms, and $Q_3$ comprises a reactive or non-reactive functionality;

Z is a ribose sugar analog or a deoxyribose sugar analog which bears at least one substituent at the 3' or 5' position of said deoxyribose sugar analog, or at the 2', 3', or 5' position of said ribose sugar analog; said substituent being selected from the group consisting of O, H, lower alkyl, substituted lower alkyl, aralkyl, heteroaralkyl, heterocycloalkyl, amino-alkylamino, heterocycloalkyl, polyalkylamino, substituted silyl, F, Cl, Br, CN, CF$_3$, OCF$_3$, OCN, O-alkyl, S-alkyl, SOMe, SO$_2$Me, ONO$_2$, NO$_2$, N$_3$, NH$_2$, NH-alkyl, OCH$_2$CH=CH$_2$, OCH=CH$_2$, OCH$_2$CCH, OCCH, OCCHO, and an RNA cleaving moiety;

said reactive functionality is selected from the group consisting of halogens, heterocycles, heterocycloalkyls, heterocycloalkylamines, polyalkylamines, aminoalkylamines, ethers, esters, aldehydes, ketones, aryl groups, hydrazines, hydroxylamines, semicarbazides, thiosemicarbazides, hydrazones, hydrazides, alcohols, and thiols; and said unreactive functionality is selected from the group consisting of alkyl groups, polyamides, intercalators, and ethylene glycols.

17. The compound of claim 16 wherein W is R$_4$Q$_3$, said Q$_3$ is a nitrogen-containing heterocycle having a plurality of ring atoms, one to four of said ring atoms being nitrogen atoms and the remainder being carbon atoms.

18. The compound of claim 16 wherein W is R$_4$Q$_3$ and said Q$_3$ is an imidazole.

19. The compound of claim 16 wherein W is R$_4$Q$_3$, said Q$_3$ is an amine.

20. The compound of claim 16 further having a phosphate group at the 3' position of the sugar analog, wherein said phosphate group may be a native phosphate or a modified phosphate.

21. The compound of claim 16 wherein said Z bears a substituent selected from the group consisting of F, CF$_3$, OCF$_3$, OCN, O-alkyl, S-alkyl, NH-alkyl, SOMe, SO$_2$Me, OCH$_2$CH=CH$_2$, OCH=CH$_2$, OCH$_2$CCH, OCCH, OCCHO and an RNA cleaving moiety.

22. The compound of claim 16 wherein said Z bears a substituent selected from the group consisting of F, CF$_3$, OCF$_3$, OCN, O-alkyl, S-alkyl, NH-alkyl, SOMe, SO$_2$Me, OCH$_2$CH=CH$_2$, OCH=CH$_2$, OCH$_2$CCH, OCCH, OCCHO and an RNA cleaving moiety; and said modified phosphate is a methylphosphonate, phosphorothioate, phosphorodithioate, phosphoramidite, or phosphorotriester.

23. The compound of claim 22 wherein G is N; and X is OR$_2$Q$_1$, wherein said R$_2$ is a lower alkane and Q$_1$ is phenyl.

24. The compound of claim 23 wherein said R$_2$ is an alkane having from about 2 to about 4 carbon atoms.

25. The compound of claim 22 wherein G is N; X is OR$_2$Q$_1$, wherein R$_2$ is lower alkane and Q$_1$ is phenyl.

26. The compound of claim 25 wherein said R$_2$ is methyl.

27. The compound of claim 25 wherein said R$_2$ is propyl.

28. The compound of claim 22 wherein G is N; X is OR$_2$Q$_1$, wherein R$_2$ is propyl and Q$_1$ is nitrophenyl.

29. The compound of claim 22 wherein said R$_2$ is propyl; Q$_1$ is nitrophenyl; Y is NHR$_3$Q$_2$; R$_3$ is propyl; and Q$_3$ is imidazole.

30. The compound of claim 22 wherein said R$_2$ is methyl; said Q$_1$ is phenyl; and Y is fluorine.

31. The compound of claim 1 further having a phosphate group at the 3' position of the sugar analog, wherein said phosphate group may be a native phosphate or a modified phosphate.

32. The compound of claim 31 wherein said modified phosphate is a methylphosphonate, phosphorothioate, phosphorodithioate, phosphoramidite, or phosphorotriester.

33. An oligonucleotide having at least one nucleotide of the formula:

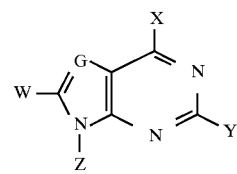

wherein:
G is CR$_1$ or N;
R$_1$ is H or a hydrocarbyl group having from 1 to 6 carbon atoms;
X is halogen, NH$_2$, OH, NHR$_2$Q$_1$ or OR$_2$Q$_1$, wherein said R$_2$ is a hydrocarbyl group having from 1 to about 20 carbon atoms, and Q$_1$ comprises a reactive or non-reactive functionality;
Y is halogen, NH$_2$, H, R$_3$Q$_2$, or NHR$_3$Q$_2$, wherein said R$_3$ is a hydrocarbyl group having from 1 to about 20 carbon atoms, and Q$_2$ comprises a reactive or non-reactive functionality;
W is H, R$_4$Q$_3$, or NHR$_4$Q$_3$, wherein said R$_4$ is a hydrocarbyl group having from 1 to about 20 carbon atoms, and Q$_3$ comprises a reactive or non-reactive functionality;
Z is a ribose sugar analog or a deoxyribose sugar analog which bears at least one substituent at the 3' or 5' position of said deoxyribose sugar analog, or at the 2', 3', or 5' position of said ribose sugar analog; said substituent being selected from the group consisting of O, H, lower alkyl, substituted lower alkyl, aralkyl, heteroaralkyl, heterocycloalkyl, amino-alkylamino, heterocycloalkyl, polyalkylamino, substituted silyl, F, Cl, Br, CN, CF$_3$, OCF$_3$, OCN, O-alkyl, S-alkyl, SOMe, SO$_2$Me, ONO$_2$, NO$_2$, N$_3$, NH$_2$, NH-alkyl, OCH$_2$CH=CH$_2$, OCH=CH$_2$, OCH$_2$CCH, OCCH, OCCHO, and an RNA cleaving moiety;
said reactive functionality is selected from the group consisting of halogens, heterocycles, heterocycloalkyls, heterocycloalkylamines, polyalkylamines, aminoalkylamines, ethers, esters, aldehydes, ketones, aryl groups, hydrazines, hydroxylamines, semicarbazides, thiosemicarbazides, hydrazones, hydrazides, alcohols, and thiols;
said unreactive functionality is selected from the group consisting of alkyl groups, polyamides, intercalators, and ethylene glycols; and
wherein at least one of X, Y and W is selected such that X is NHR$_2$Q$_1$, or OR$_2$Q$_1$, Y is R$_3$Q$_2$ or NHR$_3$Q$_2$, or W is NHR$_4$Q$_3$.

34. The oligonucleotide of claim 33 wherein G is N.

35. The oligonucleotide of claim 33 having from 2 to 40 linked nucleotides.

36. The oligonucleotide of claim 33 having from 2 to 18 linked nucleotides.

37. The compound of claim 33 wherein said Z bears a substituent selected from the group consisting of F, CF$_3$, OCF$_3$, OCN, O-alkyl, S-alkyl, NH-alkyl, SOMe, SO$_2$Me, OCH$_2$CH=CH$_2$, OCH=CH$_2$, OCH$_2$CCH, OCCH, OCCHO and an RNA cleaving moiety.

38. An oligonucleotide for affecting RNase H cleavage of RNA comprising:
a first oligonucleotide region and a second oligonucleotide region;
together said first and said second region having a nucleotide sequence essentially complementary to at least a portion of said RNA;

said first region including at least one compound of the formula:

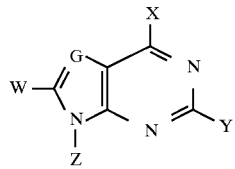

wherein:
G is $CR_1$ or N;
$R_1$ is H or a hydrocarbyl group having from 1 to 6 carbon atoms;
X is halogen, $NH_2$, OH, $NHR_2Q_1$ or $OR_2Q_1$, wherein said $R_2$ is a hydrocarbyl group having from 1 to about 20 carbon atoms, and $Q_1$ comprises a reactive or non-reactive functionality;
Y is halogen, $NH_2$, H, $R_3Q_2$, or $NHR_3Q_2$, wherein said $R_3$ is a hydrocarbyl group having from 1 to about 20 carbon atoms, and $Q_2$ comprises a reactive or non-reactive functionality;
W is H, $R_4Q_3$, or $NHR_4Q_3$, wherein said $R_4$ is a hydrocarbyl group having from 1 to about 20 carbon atoms, and $Q_3$ comprises a reactive or non-reactive functionality;
Z is a ribose sugar analog or a deoxyribose sugar analog which bears at least one substituent at the 3' or 5' position of said deoxyribose sugar analog, or at the 2', 3', or 5' position of said ribose sugar analog; said substituent being selected from the group consisting of O, H, lower alkyl, substituted lower alkyl, aralkyl, heteroaralkyl, heterocycloalkyl, amino-alkylamino, heterocycloalkyl, polyalkylamino, substituted silyl, F, Cl, Br, CN, $CF_3$, $OCF_3$, OCN, O-alkyl, S-alkyl, SOMe, $SO_2Me$, $ONO_2$, $NO_2$, $N_3$, $NH_2$, NH-alkyl, $OCH_2CH=CH_2$, $OCH=CH_2$, $OCH_2CCH$, OCCH, OCCHO, and an RNA cleaving moiety;
said reactive functionality is selected from the group consisting of halogens, heterocycles, heterocycloalkyls, heterocycloalkylamines, polyalkylamines, aminoalkylamines, ethers, esters, aldehydes, ketones, aryl groups, hydrazines, hydroxylamines, semicarbazides, thiosemicarbazides, hydrazones, hydrazides, alcohols, and thiols;
said unreactive functionality is selected from the group consisting of alkyl groups, polyamides, intercalators, and ethylene glycols;
wherein at least one of X, Y and W is selected such that X is $NHR_2Q_1$ or $OR_2Q_1$, Y is $R_3Q_2$ or $NHR_3Q_2$, or W is $NHR_4Q_3$; and
said second region including a plurality of consecutive phosphorothioate linked nucleotides having a 2'-deoxy-erythropentofuranosyl sugar moiety.

39. The oligonucleotide of claim 38 wherein G is N.
40. An oligonucleotide of claim 38 having from 2 to 40 linked nucleotides.
41. An oligonucleotide of claim 38 having from 2 to 18 linked nucleotides.
42. The oligonucleotide of claim 38 wherein said Z bears a substituent selected from the group consisting of F, $CF_3$, $OCF_3$, OCN, O-alkyl, S-alkyl, NH-alkyl, SOMe, $SO_2Me$, $OCH_2CH=CH_2$, $OCH=CH_2$, $OCH_2CCH$, OCCH, OCCHO and an RNA cleaving moiety.
43. An oligonucleotide of claim 35 further comprising:
a third region of said oligonucleotide, said third region including at least one compound of said formula; and wherein said second region is positioned in said oligonucleotide between said first and third regions.
44. The cross-linked nucleic acid of claim 38 wherein each of said first and said second oligonucleotide regions comprise a nucleotide of said formula; and
said covalent cross-linkage is between said nucleotides of said formula.
45. The cross-linked nucleic acid of claim 38 wherein said group J or K on said nucleotide of said formula in said first oligonucleotide region includes a first space-spanning group having a first active functional group; said group J or K on said second nucleotide includes a second space-spanning group having a second active functional group; and said covalent cross-linkage is between said first and second active functional groups.
46. The cross-linked nucleic acid of claim 44 wherein said group $R_7$ is from about 8 to about 13 atoms in length and said groups $Q_4$ and $Q_5$ are, independently, a thiol, an aldehyde, a protected aldehyde, an aldehyde precursor, an amine, hydrazine, hydroxylamine, semicarbazide, thiosemicarbazide, hydrazide, alcohol, or alkoxy.
47. The cross-linked nucleic acid of claim 38 wherein said X is NHJ, OJ, or SJ.
48. The cross-linked nucleic acid of claim 47 wherein said space-spanning group $R_7$ is from about 8 to about 13 atoms in length and said group $Q_4$ is, independently, a thiol, an aldehyde, a protected aldehyde, an aldehyde precursor, $NH_2$, polyalkylamine, aminoalkylamine, hydrazine (—NH—NH—), hydroxylamine (—NH—OH), semicarbazide (—NH—C(O)—NH—$NH_2$), thiosemicarbazide (—NH—C(S)—NH—$NH_2$), hydrazone (—N=NH), hydrazide (—C(O)—NH—$NH_2$), alcohol, or alkoxy.
49. The cross-linked nucleic acid of claim 44 wherein Y is J.
50. The cross-linked nucleic acid of claim 49 wherein said group $R_7$ is from about 8 to about 13 atoms in length and said group $Q_4$ is a thiol, an aldehyde, a protected aldehyde, an aldehyde precursor, an amine, hydrazine, hydroxylamine, semicarbazide, thiosemicarbazide, hydrazide, alcohol, or alkoxy.
51. The cross-linked nucleic acid of claim 44 wherein W is K.
52. The cross-linked nucleic acid of claim 51 wherein said group $R_7$ is from about 8 to about 13 atoms in length and said group $Q_5$ is a thiol, an aldehyde, a protected aldehyde, an aldehyde precursor, an amine, hydrazine, hydroxylamine, semicarbazide, thiosemicarbazide, hydrazide, alcohol, or alkoxy.
53. The cross-linked nucleic acid of claim 38 wherein said first oligonucleotide region and said second oligonucleotide region are on a single oligonucleotide strand.
54. The cross-linked oligonucleotide of claim 48 wherein said first sequence region and said second sequence region are on a single oligonucleotide strand.
55. The cross-linked oligonucleotide of claim 50 wherein said first sequence region and said second sequence region are on a single oligonucleotide strand.
56. The cross-linked oligonucleotide of claim 52 wherein said first sequence region and said second sequence region are on a single oligonucleotide strand.
57. The cross-linked nucleic acid of claim 38 wherein said first oligonucleotide region and said second oligonucleotide region are on different oligonucleotide strands.
58. The cross-linked oligonucleotide of claim 48 wherein said first sequence region and said second sequence region are on different oligonucleotide strands.

59. The cross-linked oligonucleotide of claim 50 wherein said first sequence region and said second sequence region are on different oligonucleotide strands.

60. The cross-linked oligonucleotide of claim 52 wherein said first sequence region and said second sequence region are on different oligonucleotide strands.

61. The cross-linked nucleic acid of claim 38 wherein said first oligonucleotide region and said second oligonucleotide region are complementary to and specifically hybridizable with one another.

62. The cross-linked oligonucleotide of claim 48 wherein said first sequence region and said second sequence region are complementary to and specifically hybridizable with one another.

63. The cross-linked oligonucleotide of claim 50 wherein said first sequence region and said second sequence region are complementary to and specifically hybridizable with one another.

64. The cross-linked oligonucleotide of claim 52 wherein said first sequence region and said second sequence region are complementary to and specifically hybridizable with one another.

65. The cross-linked nucleic acid of claim 38 wherein said first nucleotide of said formula is located in a first nucleotide sequence and said second nucleotide is located in a second nucleotide sequence; said second nucleotide sequence is complementary to and hybridizable with said first nucleotide sequence; and said first and said second nucleotide sequences are located on a single strand of said cross-linked nucleic acid with said second nucleotide sequence located on said cross-linked nucleic acid at a distance separated from said first nucleotide sequence sufficient to allow said cross-linked nucleic acid to assume a conformation wherein said first and second nucleotide sequences are mutually aligned with and specifically hybridized with one another.

66. The cross-linked nucleic acid of claim 38 wherein said first nucleotide of said formula is located in a first nucleotide sequence and said second nucleotide is located in a second nucleotide sequence; and said first and said second nucleotide sequences are located on a single strand of an oligonucleotide with said second nucleotide sequence located on said oligonucleotide at a non-hybridizable position with respect to said first nucleotide sequence and at a distance from said first nucleotide sequence sufficient to allow said oligonucleotide to assume a conformation wherein said first and second nucleotide sequences are located in spatial proximity with each other.

67. The cross-linked nucleic acid of claim 38 wherein said first nucleotide of said formula is located in a first nucleotide sequence and said second nucleotide is located in a second nucleotide sequence; said second nucleotide sequence is complementary to and specifically hybridizable with said first nucleotide sequence; and said first and said second nucleotide sequences are located on different oligonucleotide strands.

68. The compound of claim 2 wherein X is $NHR_2Q_1$ and said $Q_1$ is an imidazole.

69. The compound of claim 2 wherein X is $OR_2Q_1$ and said $Q_1$ is an imidazole.

70. The compound of claim 21 wherein W is $R_4Q_3$ and said $Q_3$ is an imidazole.

71. A compound having the formula:

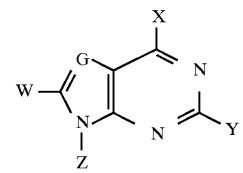

wherein:

G is N;

X is $OR_2Q_1$, wherein said $R_2$ is a hydrocarbyl group having from 1 to about 20 carbon atoms, and $Q_1$ comprises a reactive or non-reactive functionality;

Y is halogen, H, $R_3Q_2$, or $NHR_3Q_2$, wherein said $R_3$ is a hydrocarbyl group having from 1 to about 20 carbon atoms, and $Q_2$ comprises a reactive or non-reactive functionality;

W is H;

Z is H, a nitrogen protecting group, or Z is a ribose sugar analog or a deoxyribose sugar analog which bears at least one substituent at the 3' or 5' position of said deoxyribose sugar analog, or at the 2', 3', or 5' position of said ribose sugar analog; said substituent being selected from the group consisting of O, H, lower alkyl, substituted lower alkyl, aralkyl, heteroaralkyl, heterocycloalkyl, amino-alkylamino, heterocycloalkyl, polyalkylamino, substituted silyl, F, Cl, Br, CN, $CF_3$, $OCF_3$, OCN, O-alkyl, S-alkyl, $SOMe$, $SO_2Me$, $ONO_2$, $NO_2$, $N_3$, $NH_2$, NH-alkyl, $OCH_2CH=CH_2$, $OCH=CH_2$, $OCH_2CCH$, OCCH, OCCHO, and an RNA cleaving moiety; provided that where Y is $NHR_3Q_2$, said nucleoside sugar moiety is not a 2'-fluoro arabinofuranosyl sugar moiety;

said reactive functionality is selected from the group consisting of halogens, heterocycles, heterocycloalkyls, heterocycloalkylamines, polyalkylamines, aminoalkylamines, ethers, esters, aldehydes, ketones, aryl groups, hydrazines, hydroxylamines, semicarbazides, thiosemicarbazides, hydrazones, hydrazides, alcohols, and thiols; and said unreactive functionality is selected from the group consisting of alkyl groups, polyamides, intercalators, and ethylene glycols.

72. The compound of claim 71 further having a phosphate group at the 3' position of the sugar analog, wherein said phosphate group may be a native phosphate or a modified phosphate.

73. The compound of claim 71 wherein said Z bears a substituent selected from the group consisting of F, $CF_3$, $OCF_3$, OCN, O-alkyl, S-alkyl, NH-alkyl, $SOMe$, $SO_2Me$, $OCH_2CH=CH_2$, $OCH=CH_2$, $OCH_2CCH$, OCCH, OCCHO and an RNA cleaving moiety.

74. The compound of claim 74 wherein said Z bears a substituent selected from the group consisting of F, $CF_3$, $OCF_3$, OCN, O-alkyl, S-alkyl, NH-alkyl, $SOMe$, $SO_2Me$, $OCH_2CH=CH_2$, $OCH=CH_2$, $OCH_2CCH$, OCCH, OCCHO and an RNA cleaving moiety; and said modified phosphate is a methylphosphonate, phosphorothioate, phosphorodithioate, phosphoramidite, or phosphorotriester.

75. A compound having the formula:

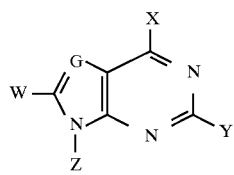

wherein:

G is N;

X is $NHR_2Q_1$ wherein said $R_2$ is a hydrocarbyl group having from 1 to about 20 carbon atoms, and $Q_1$ comprises a reactive or non-reactive functionality;

Y is $R_3Q_2$, or $NHR_3Q_2$, wherein said $R_3$ is a hydrocarbyl group having from 1 to about 20 carbon atoms, and $Q_2$ comprises a reactive or non-reactive functionality;

W is H;

Z is H, a nitrogen protecting group, or Z is a ribose sugar analog or a deoxyribose sugar analog which bears at least one substituent at the 3' or 5'3 position of said deoxyribose sugar analog, or at the 2', 3', or 5' position of said ribose sugar analog; said substituent being selected from the group consisting of O, H, lower alkyl, substituted lower alkyl, aralkyl, heteroaralkyl, heterocycloalkyl, amino-alkylamino, heterocycloalkyl, polyalkylamino, substituted silyl, F, Cl, Br, CN, $CF_3$, $OCF_3$, OCN, O-alkyl, S-alkyl, SOMe, $SO_2Me$, $ONO_2$, $NO_2$, $N_3$, $NH_2$, NH-alkyl, $OCH_2CH=CH_2$, $OCH=CH_2$, $OCH_2CCH$, OCCH, OCCHO, and an RNA cleaving moiety; provided that where X is $NHR_2Q_1$ and Y is $NHR_3Q_2$, said nucleoside sugar moiety is not a 2'-fluoro arabinofuranosyl sugar moiety;

said reactive functionality is selected from the group consisting of halogens, heterocycles, heterocycloalkyls, heterocycloalkylamines, polyalkylamines, aminoalkylamines, ethers, esters, aldehydes, ketones, hydrazines, hydroxylamines, semicarbazides, thiosemicarbazides, hydrazones, hydrazides, alcohols, and thiols; and said unreactive functionality is selected from the group consisting of alkyl groups, polyamides, intercalators, and ethylene glycols.

76. The compound of claim 75 further having a phosphate group at the 3' position of the sugar analog, wherein said phosphate group may be a native phosphate or a modified phosphate.

77. The compound of claim 75 wherein said Z bears a substituent selected from the group consisting of F, $CF_3$, $OCF_3$, OCN, O-alkyl, S-alkyl, NH-alkyl, SOMe, $SO_2Me$, $OCH_2CH=CH_2$, $OCH=CH_2$, $OCH_2CCH$, OCCH, OCCHO and an RNA cleaving moiety.

78. The compound of claim 75 wherein said Z bears a substituent selected from the group consisting of F, $CF_3$, $OCF_3$, OCN, O-alkyl, S-alkyl, NH-alkyl, SOMe, $SO_2Me$, $OCH_2CH=CH_2$, $OCH=CH_2$, $OCH_2CCH$, OCCH, OCCHO and an RNA cleaving moiety; and said modified phosphate is a methylphosphonate, phosphorothioate, phosphorodithioate, phosphoramidite, or phosphorotriester.

79. A cross-linked nucleic acid comprising:

a first oligonucleotide region and a second oligonucleotide region, wherein said first region includes at least one nucleotide of the formula:

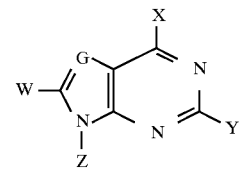

wherein:

G is $CR_5$ or N;

$R_5$ is H or a hydrocarbyl group having from 1 to 6 carbon atoms;

X is halogen $NH_2$, OH, $NHR_6Q_1$, $OR_6Q_1$, NHJ, OJ or SJ wherein said $R_6$ is H or a hydrocarbyl group having from 2 to about 20 carbon atoms;

$Q_1$ comprises at least one reactive or non-reactive functionality;

J comprises a space spanning group $R_7$ and an active functional group $Q_4$;

Y is halogen, $NH_2$, H, SH, OH, NHJ, OJ or SJ where J comprises a space spanning group $R_7$ and an active functional group $Q_4$;

W is H, NHK, OK or SK where K comprises a space spanning group $R_7$ and an active non-psoralen functional group $Q_5$;

Z is a ribose sugar analog or a deoxyribose sugar analog which bears at least one substituent at the 3' or 5' position of said deoxyribose sugar analog, or at the 2', 3', or 5' position of said ribose sugar analog; said substituent being selected from the group consisting of O, H, lower alkyl, substituted lower alkyl, aralkyl, heteroaralkyl, heterocycloalkyl, amino-alkylamino, heterocycloalkyl, polyalkylamino, substituted silyl, F, Cl, Br, CN, $CF_3$, $OCF_3$, OCN, O-alkyl, S-alkyl, SOMe, $SO_2Me$, $ONO_2$, $NO_2$, $N_3$, $NH_2$, NH-alkyl, $OCH_2CH=CH_2$, $OCH=CH_2$, $OCH_2CCH$, OCCH, OCCHO, and an RNA cleaving moiety;

said space spanning group $R_7$ is a hydrocarbyl group having from 2 to about 20 carbon atoms;

at least one of said X or Y groups is NHJ, OJ or SJ, or at least one of said W groups is NHK, OK or SK; and said second region includes a second nucleotide of said formula capable of covalently bonding with said J group or said W group of said nucleotide of said formula in said first oligonucleotide region thereby forming a covalent cross-linkage between said first and said second oligonucleotide regions.

80. The cross-linked nucleic acid of claim 79 wherein G is N.

81. The cross linked nucleic acid of claim 79 having from 2 to 40 linked nucleotides.

82. The cross linked nucleic acid of claim 79 having from 2 to 18 linked nucleotides.

83. The cross linked nucleic acid of claim 79 wherein said Z bears a substituent selected from the group consisting of F, $CF_3$, $OCF_3$, OCN, O-alkyl, S-alkyl, NH-alkyl, SOMe, $SO_2Me$, $OCH_2CH=CH_2$, $OCH=CH_2$, $OCH_2CCH$, OCCH, OCCHO and an RNA cleaving moiety.

* * * * *